US012570966B2

(12) United States Patent
Agrawal et al.

(10) Patent No.: US 12,570,966 B2
(45) Date of Patent: Mar. 10, 2026

(54) MUTATED PIGGYBAC® TRANSPOSASE

(71) Applicant: AMGEN INC., Thousand Oaks, CA (US)

(72) Inventors: Neeraj J. Agrawal, Natick, MA (US); Kristine M. Daris, Newbury Park, CA (US); Jennitte L. Stevens, Thousand Oaks, CA (US); Huong Thi Ngoc Le, Newbury Park, CA (US); Noelia Blanco Talavan, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 1317 days.

(21) Appl. No.: 17/299,000

(22) PCT Filed: Dec. 9, 2019

(86) PCT No.: PCT/US2019/065129
§ 371 (c)(1),
(2) Date: Jun. 2, 2021

(87) PCT Pub. No.: WO2020/123327
PCT Pub. Date: Jun. 18, 2020

(65) Prior Publication Data
US 2022/0064610 A1 Mar. 3, 2022

Related U.S. Application Data

(60) Provisional application No. 62/925,516, filed on Oct. 24, 2019, provisional application No. 62/777,325, filed on Dec. 10, 2018.

(51) Int. Cl.
| | |
|---|---|
| *C12N 9/12* | (2006.01) |
| *A61K 40/11* | (2025.01) |
| *A61K 40/32* | (2025.01) |
| *A61K 40/40* | (2025.01) |
| *C07K 14/725* | (2006.01) |
| *C12N 15/85* | (2006.01) |
| *C12N 15/90* | (2006.01) |

(52) U.S. Cl.
CPC ............ *C12N 9/1241* (2013.01); *A61K 40/11* (2025.01); *A61K 40/32* (2025.01); *A61K 40/40* (2025.01); *C07K 14/7051* (2013.01); *C12N 15/85* (2013.01); *C12N 15/90* (2013.01); *C12Y 207/07* (2013.01); *C12N 2800/90* (2013.01)

(58) Field of Classification Search
None
See application file for complete search history.

(56) References Cited

U.S. PATENT DOCUMENTS

| | | | |
|---|---|---|---|
| 6,218,185 B1 | 4/2001 | Shirk et al. | |
| 7,105,343 B1 | 9/2006 | Fraser, Jr. et al. | |
| 7,932,088 B1 | 4/2011 | Adams | |
| 8,399,643 B2 | 3/2013 | Ostertag et al. | |
| 8,741,340 B2 | 6/2014 | Kusk et al. | |
| 9,670,503 B2 | 6/2017 | Craig | |
| 9,783,790 B2 | 10/2017 | Craig | |
| 10,358,671 B2 | 7/2019 | Kawakami et al. | |
| 2006/0210977 A1 | 9/2006 | Kaminski | |
| 2007/0204356 A1 | 8/2007 | Fraser | |
| 2009/0042297 A1 | 2/2009 | George, Jr. et al. | |
| 2010/0311116 A1 | 12/2010 | Wurm et al. | |
| 2013/0131318 A1* | 5/2013 | Kremer ............... B01D 15/327 530/387.1 |
| 2015/0361451 A1 | 12/2015 | Le Fourn et al. | |
| 2016/0015749 A1* | 1/2016 | Gottschalk ............. C07K 16/30 435/325 |
| 2016/0208239 A1 | 7/2016 | Bradley et al. | |
| 2018/0265890 A1 | 9/2018 | Qian et al. | |
| 2019/0071484 A1 | 3/2019 | Uckert et al. | |

FOREIGN PATENT DOCUMENTS

| | | | |
|---|---|---|---|
| CN | 103360464 A | 10/2013 | |
| EP | 3129487 B1 | 7/2020 | |
| WO | 2010085699 A2 | 7/2010 | |
| WO | WO-2010099296 A1 * | 9/2010 | ......... A01K 67/0275 |
| WO | 2013019625 A1 | 2/2012 | |
| WO | 2013074974 A2 | 5/2013 | |
| WO | 2015157579 A2 | 10/2015 | |
| WO | 2016028649 A1 | 2/2016 | |
| WO | 2017062668 A2 | 4/2017 | |
| WO | 2017101749 A2 | 6/2017 | |
| WO | 2017147538 A1 | 8/2017 | |
| WO | 2019046815 A1 | 3/2019 | |
| WO | 2020123410 A1 | 6/2020 | |
| WO | 2012074758 A1 | 6/2021 | |

OTHER PUBLICATIONS

Dar et al., "siRNAmod: A database of experimentally validated chemically modified siRNAs," *Scientific Rpts.*, vol. 6 (1), pp. 1-8 (2016).
Hassler et al., "Comparison of partially and fully chemically-modified siRNA in conjugate-mediated delivery in vivo," *Nucleic Acids Res.*, vol. 46 (5), pp. 2185-2196 (2018).
Nair et al., "Multivalent N-Acetylgalactosamine-Conjugated siRNA Localizes in Hepatocytes and Elicits Robust RNAi-Mediated Gene Silencing," *J. Am. Chem. Soc.*, vol. 136 (49), pp. 16958-16961 (2014).
Petrova et al., "Structure—functions relations in small interfering RNAs," *Practical Applications in Biomedical Engineering*, Ch. 8, pp. 187-228 (2012).
Selvam et al., "Therapeutic potential of chemically modified siRNA: recent trends," *Chem. Biol. Drug Des.*, pp. 1-14 (2017).

(Continued)

*Primary Examiner* — Jennifer Dunston
*Assistant Examiner* — Tiffany Nicole Grooms
(74) *Attorney, Agent, or Firm* — Alla Brukman

(57) ABSTRACT

PIGGYBAC® transposases engineered to increase stability in a cell. The engineered PIGGYBAC® transposases are useful for stably transforming cells, cell line development, genome modification, and improving titer of recombinant proteins, among other uses.

26 Claims, 10 Drawing Sheets
Specification includes a Sequence Listing.

(56)    References Cited

OTHER PUBLICATIONS

Watts et al., "Chemically modified siRNA: tools and applications," *Drug Discovery Today*, vol. 13 (19/20), pp. 842-855 (2008).

Ahmadi, et al, PLOS One, *Monoclonal antibodies expression improvement in CHO cells by PiggyBac transposition regarding vectors ratios and design*, pp. 1-16, 2007.

Balasubramanian, et al, *Rapid recombinant protein production from piggyBac transposon-mediated stable CHO cell pools*, J Biotechnology, v200, pp. 61-19, 2015.

Balasubramanian, et al, *Multigene Expression in Stable CHO Cell Pools Generated with the piggyBac Transposon System*, Biotech, v32 #5, pp. 1308-1317, 2016.

Balasubramanian, et al, *Comparison of Three Transposons for the Generation of Highly Productive Recombinant CHO Cell Pools and Cell Lines*, Biotech & Bioengineering, v113, #6, pp. 1234-1243, 2016.

Cary, et al, *Transposon Mutagenesis of Baculoviruses: Analysis of Trichoplusia ni Transposon IFP2 Insertions within the FP-Locus of Nuclear Polyhedrosis Viruses*, Virology, v172, pp. 56-169, 1989.

Ding, et al, *Efficient Transposition of the piggyBac (PB) Transposon in Mammalian Cells and Mice*, Cell v122, pp. 473-483, 2005.

Fraser, et al, *Assay for Movement of Lepidopteran Transposon IFP2 in Insect Cells Using a Baculovirus Genome as a Target DNA*, Virology, v211, pp. 397-407, 1995.

Hacket, et al., *A Transposon and Transposase System for Human Application*, Am Soc of Gene & Cell Therapy, v18 34, pp. 674-693, 2010.

International Search Report for PCT Application No. PCT/US2019/065129, mailed on Mar. 27, 2020.

Li, et al, *The minimum internal and external sequence requirements for transposition of the eukaryotic transposition vector piggyBac*, Mol Genet Genomics, v266, pp. 190-198, 2001.

Matasci, *CO2 and Multigas Incubators for Precise Cell Culture Reproducibility*, PHC Corp of N America, 2011.

Rajendra, et al, *Generation of Stable Chinese Hamster Ovary Pools Yielding Antibody Titers of up to 7.6 g/L Using the piggyBac Transposon System*, Biotechnol v32 #5, pp. 1301-1307, 2016.

International Written Opinion for PCT Application No. PCT/US2019/065129.

Wu, et al, *piggyBac is a flexible and highly active transposonas compared to Sleeping Beauty, Tol2, and Mos1 in mammalian cells*, PNAS, v103 #41, pp. 15008-15013, 2006.

XP002798126, 2017.

XP013198532D2, *Predicted: piggyBac transposable element-derived protein 4-like [Amyelois transitella]*, 2015.

XP022823959D3, *piggyBac transposable element-derived protein 4-like [Spodoptera litura]*, 2017.

Yusa, et al, *A hyperactive piggyBac transposase for mammalian applications* PNAS, v108 #4, pp. 1531-1536, 2011.

Yusa, et al, *SI Materials and Methods*, PNAS, pp. 1-6, 2011.

\* cited by examiner

FIG. 1 mPBase
DSC mPBase
DSC mPBase
DSC mPBase
DSC mPBase
DSC mPBase
DSC mPBase
DSC

RT-PCR

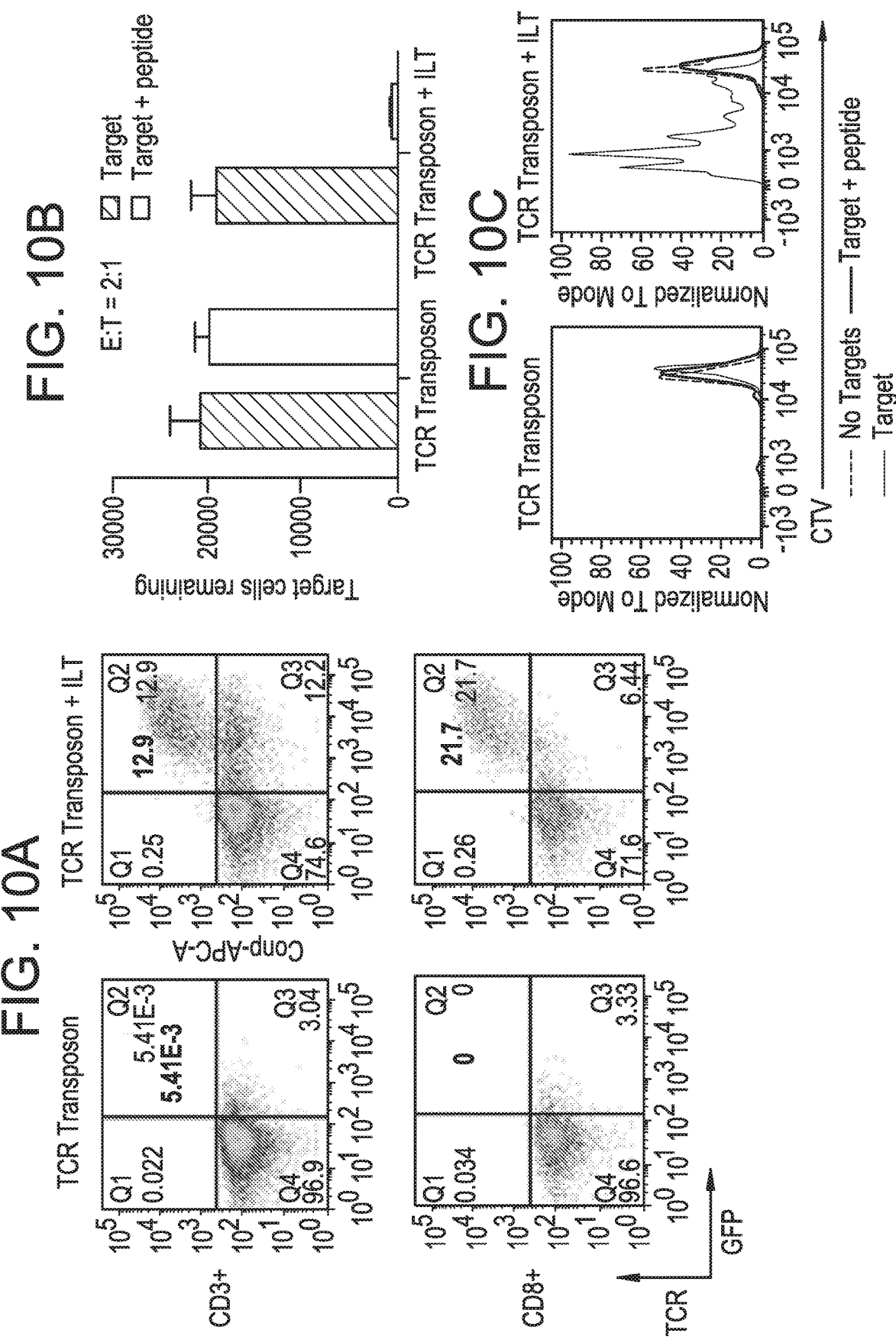

SEQUENCE LISTING

```
<160> NUMBER OF SEQ ID NOS: 18

<210> SEQ ID NO 1
<211> LENGTH: 1786
<212> TYPE: DNA
<213> ORGANISM: Trichoplusia ni

<400> SEQUENCE: 1
atgggctcta gcctggacga cgagcacatc ctgagcgccc tgctgcagag cgacgacgaa        60
ctggtgggcg aggacagcga cagcgagatc agcgaccacg tgtccgagga cgacgtgcag       120
tccgacaccg aggaagcctt catcgacgag gtgcacgaag tgcagcctac cagcagcggc       180
tccgagatcc tggacgagca gaacgtgatc gagcagcctg gcagctccct ggccagcaac       240
agaatcctga ccctgcccca gagaaccatc agaggcaaga caagcactg ctggtccacc        300 tccaagagca ccaggcggag cagagtgtcc gccctgaaca tcgtgcggag ccagaggggc       360
cccaccagaa tgtgcagaaa catctacgac cccctgctgt gcttcaagct gttcttcacc       420
gacgagatca tcagcgagat cgtgaagtgg accaacgccg agatcagcct gaagaggcgg       480
gagagcatga ccggcgccac cttcagagac accaacgagg acgagatcta cgccttcttc       540
ggcatcctgg tgatgaccgc cgtgagaaag gacaaccaca tgagcaccga cgacctgttc       600
gacagatccc tgagcatggt gtacgtgtcc gtgatgagca gagacagatt cgacttcctg       660
atcagatgcc tgagaatgga cgacaagagc atcagaccca ccctgcggga gaacgacgtg       720
ttcacccccg tgcggaagat ctgggacctg ttcatccacc agtgcatcca gaactacacc       780
cctggcgccc acctgaccat cgatgagcag ctgctgggct tcagaggcag atgccccttc       840
agaatgtaca tccccaacaa gcccagcaag tacggcatca agatcctgat gatgtgcgac       900
agcggcacca agtacatgat caacggcatg ccctacctgg gcagaggcac ccagacaaac       960
ggcgtgcccc tgggcgagta ctacgtgaaa gaactgagca agcctgtgca tggcagctgc      1020
```

-continued

```
aggaacatca cctgcgacaa ctggttcacc agcatccccc tggccaagaa cctgctgcag   1080
gaaccctaca agctgaccat cgtgggcacc gtgcggagca acaagcggga gatcccagag   1140
gtgctgaaga acagcagatc cagacctgtg ggaacaagca tgttctgctt cgacggcccc   1200
ctgaccctgg tgtcctacaa gcccaagccc gccaagatgg tgtacctgct gtccagctgc   1260
gacgaggacg ccagcatcaa cgagagcacc ggcaagcccc agatggtgat gtactacaac   1320
cagaccaagg gcggcgtgga caccctggac cagatgtgca gcgtgatgac ctgcagcaga   1380
aagaccaaca gatggcccat ggccctgctg tacggcatga tcaatatcgc ctgcatcaac   1440
agcttcatca tctacagcca caacgtgtcc agcaagggcg agaaggtgca gagccggaag   1500
aaattcatgc ggaacctgta catgagcctg acctccagct tcatgagaaa gagactggaa   1560
gcccccaccc tgaagagata cctgcgggac aacatcagca acatcctgcc caacgaagtg   1620
ccaggaacaa gcgacgacag caccgaggaa cccgtgatga agaagaggac ctactgcacc   1680
tactgtccca gcaagatcag aagaaaggcc aacgccagct gcaagaaatg caaaaaagtg   1740
atctgccggg agcacaacat cgacatgtgc cagagctgtt tctagc               1786
```

```
<210> SEQ ID NO 2
<211> LENGTH: 594
<212> TYPE: PRT
<213> ORGANISM: Trichoplusia ni

<400> SEQUENCE: 2

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
                20                  25                  30

His Val Ser Glu Asp Asp Val Gln Ser Asp Thr Glu Glu Ala Phe Ile
            35                  40                  45

Asp Glu Val His Glu Val Gln Pro Thr Ser Ser Gly Ser Glu Ile Leu
        50                  55                  60

Asp Glu Gln Asn Val Ile Glu Gln Pro Gly Ser Ser Leu Ala Ser Asn
65                  70                  75                  80

Arg Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn Ile Val Arg Ser Gln Arg Gly Pro Thr Arg Met Cys Arg Asn Ile
        115                 120                 125

Tyr Asp Pro Leu Leu Cys Phe Lys Leu Phe Phe Thr Asp Glu Ile Ile
    130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
    210                 215                 220

Arg Met Asp Asp Lys Ser Ile Arg Pro Thr Leu Arg Glu Asn Asp Val
225                 230                 235                 240
```

```
Phe Thr Pro Val Arg Lys Ile Trp Asp Leu Phe Ile His Gln Cys Ile
            245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
            275                 280                 285

Ser Lys Tyr Gly Ile Lys Ile Leu Met Met Cys Asp Ser Gly Thr Lys
            290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
            325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
            355                 360                 365

Gly Thr Val Arg Ser Asn Lys Arg Glu Ile Pro Glu Val Leu Lys Asn
            370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
            405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
            435                 440                 445

Leu Asp Gln Met Cys Ser Val Met Thr Cys Ser Arg Lys Thr Asn Arg
            450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
            485                 490                 495

Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
            515                 520                 525

Arg Asp Asn Ile Ser Asn Ile Leu Pro Asn Glu Val Pro Gly Thr Ser
            530                 535                 540

Asp Asp Ser Thr Glu Glu Pro Val Met Lys Lys Arg Thr Tyr Cys Thr
545                 550                 555                 560

Tyr Cys Pro Ser Lys Ile Arg Arg Lys Ala Asn Ala Ser Cys Lys Lys
            565                 570                 575

Cys Lys Lys Val Ile Cys Arg Glu His Asn Ile Asp Met Cys Gln Ser
            580                 585                 590

Cys Phe

<210> SEQ ID NO 3
<211> LENGTH: 1786
<212> TYPE: DNA
<213> ORGANISM: Trichoplusia ni

<400> SEQUENCE: 3
atgggctcta gcctggacga cgagcacatc ctgagcgccc tgctgcagag cgacgacgaa        60
ctggtgggcg aggacagcga cagcgagatc agcgaccacg tgtccgagga cgacgtgcag       120
```

```
tccgacaccg aggaagcctt catcgacgag gtgcacgaag tgcagcctac cagcagcggc      180
tccgagatcc tggacgagca gaacgtgatc gagcagcctg gcagctccct ggccagcaac      240
agaatcctga ccctgcccca gagaaccatc agaggcaaga acaagcactg ctggtccacc      300
tccaagagca ccaggcggag cagagtgtcc gccctgaaca tcgtgcggag ccagaggggc      360
cccaccagaa tgtgcagaaa catctacgac cccctgctgt gcttcaagct gttcttcacc      420
gacgagatca tcagcgagct ggtgaagtgg accaacgccg agatcagcct gaagaggcgg      480
gagagcatga ccggcgccac cttcagagac accaacgagg acgagatcta cgccttcttc      540
ggcatcctgg tgatgaccgc cgtgagaaag gacaaccaca tgagcaccga cgacctgttc      600
gacagatccc tgagcatggt gtacgtgtcc gtgatgagca gagacagatt cgacttcctg      660
atcagatgcc tgagaatgga cgacaagagc atcagaccca ccctgcggga gaacgacgtg      720 ttcaccccccg tgcggaagat ctgggacctg ttcatccacc agtgcatcca gaactacacc      780
cctggcgccc acctgaccat cgatgagcag ctgctgggct tcagaggcag atgccccttc      840
agaatgtaca tccccaacaa gcccagcaag tacggcatca agatcctgat gatgtgcgac      900
agcggcacca gtacatgat caacggcatg ccctacctgg gcagaggcac ccagacaaac      960
ggcgtgcccc tgggcgagta ctacgtgaaa gaactgagca gcctgtgca tggcagctgc     1020 aggaacatca cctgcgacaa cctggttcacc agcatccccc tggccaagaa cctgctgcag     1080
gaaccctaca gctgaccat cgtgggcacc gtgcggagca acaagcggga tcccagag     1140 gtgctgaaga acagcagatc cagacctgtg ggaacaagca tgttctgctt cgacggcccc     1200
ctgaccctgg tgtcctacaa gcccaagccc gccaagatgg tgtacctgct gtccagctgc     1260
gacgaggacg ccagcatcaa cgagagcacc ggcaagcccc agatggtgat gtactacaac     1320
cagaccaagg gcggcgtgga caccctggac cagatgtgca gcgtgatgac ctgcagcaga     1380
aagaccaaca gatggcccat ggccctgctg tacggcatga tcaatatcgc ctgcatcaac     1440
agcttcatca tctacagcca caacgtgtcc agcaagggcg agaaggtgca gagccggaag     1500
aaattcatgc ggaacctgta catgagcctg acctccagct tcatgagaaa gagactggaa     1560
gcccccaccc tgaagagata cctgcgggac aacatcagca catcctgcc caacgaagtg     1620 ccaggaacaa gcgacgacag caccgaggaa cccgtgatga agaagaggac ctactgcacc     1680
tactgtccca gcaagatcag aagaaaggcc aacgccagct gcaagaaatg caaaaaagtg     1740
atctgccggg agcacaacat cgacatgtgc cagagctgtt tctagc                    1786
```

```
<210> SEQ ID NO 4
<211> LENGTH: 594
<212> TYPE: PRT
<213> ORGANISM: Trichoplusia ni

<400> SEQUENCE: 4

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
                20                  25                  30

His Val Ser Glu Asp Asp Val Gln Ser Asp Thr Glu Glu Ala Phe Ile
            35                  40                  45

Asp Glu Val His Glu Val Gln Pro Thr Ser Ser Gly Ser Glu Ile Leu
        50                  55                  60

Asp Glu Gln Asn Val Ile Glu Gln Pro Gly Ser Ser Leu Ala Ser Asn
65                  70                  75                  80
```

```
Arg Ile Leu Thr Leu Pro Gln Arg Thr Ile Arg Gly Lys Asn Lys His
            85              90              95

Cys Trp Ser Thr Ser Lys Ser Thr Arg Arg Ser Arg Val Ser Ala Leu
            100             105             110

Asn Ile Val Arg Ser Gln Arg Gly Pro Thr Arg Met Cys Arg Asn Ile
            115             120             125

Tyr Asp Pro Leu Leu Cys Phe Lys Leu Phe Phe Thr Asp Glu Ile Ile
    130             135             140

Ser Glu Leu Val Lys Trp Thr Asn Ala Glu Ile Ser Leu Lys Arg Arg
145             150             155             160

Glu Ser Met Thr Gly Ala Thr Phe Arg Asp Thr Asn Glu Asp Glu Ile
            165             170             175

Tyr Ala Phe Phe Gly Ile Leu Val Met Thr Ala Val Arg Lys Asp Asn
            180             185             190

His Met Ser Thr Asp Asp Leu Phe Asp Arg Ser Leu Ser Met Val Tyr
            195             200             205

Val Ser Val Met Ser Arg Asp Arg Phe Asp Phe Leu Ile Arg Cys Leu
    210             215             220

Arg Met Asp Asp Lys Ser Ile Arg Pro Thr Leu Arg Glu Asn Asp Val
225             230             235             240

Phe Thr Pro Val Arg Lys Ile Trp Asp Leu Phe Ile His Gln Cys Ile
            245             250             255

Gln Asn Tyr Thr Pro Gly Ala His Leu Thr Ile Asp Glu Gln Leu Leu
            260             265             270

Gly Phe Arg Gly Arg Cys Pro Phe Arg Met Tyr Ile Pro Asn Lys Pro
            275             280             285

Ser Lys Tyr Gly Ile Lys Ile Leu Met Met Cys Asp Ser Gly Thr Lys
    290             295             300

Tyr Met Ile Asn Gly Met Pro Tyr Leu Gly Arg Gly Thr Gln Thr Asn
305             310             315             320

Gly Val Pro Leu Gly Glu Tyr Tyr Val Lys Glu Leu Ser Lys Pro Val
            325             330             335

His Gly Ser Cys Arg Asn Ile Thr Cys Asp Asn Trp Phe Thr Ser Ile
            340             345             350

Pro Leu Ala Lys Asn Leu Leu Gln Glu Pro Tyr Lys Leu Thr Ile Val
            355             360             365

Gly Thr Val Arg Ser Asn Lys Arg Glu Ile Pro Glu Val Leu Lys Asn
    370             375             380

Ser Arg Ser Arg Pro Val Gly Thr Ser Met Phe Cys Phe Asp Gly Pro
385             390             395             400

Leu Thr Leu Val Ser Tyr Lys Pro Lys Pro Ala Lys Met Val Tyr Leu
            405             410             415

Leu Ser Ser Cys Asp Glu Asp Ala Ser Ile Asn Glu Ser Thr Gly Lys
            420             425             430

Pro Gln Met Val Met Tyr Tyr Asn Gln Thr Lys Gly Gly Val Asp Thr
            435             440             445

Leu Asp Gln Met Cys Ser Val Met Thr Cys Ser Arg Lys Thr Asn Arg
    450             455             460

Trp Pro Met Ala Leu Leu Tyr Gly Met Ile Asn Ile Ala Cys Ile Asn
465             470             475             480

Ser Phe Ile Ile Tyr Ser His Asn Val Ser Ser Lys Gly Glu Lys Val
            485             490             495
```

-continued

```
Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
            515                 520                 525

Arg Asp Asn Ile Ser Asn Ile Leu Pro Asn Glu Val Pro Gly Thr Ser
            530                 535                 540

Asp Asp Ser Thr Glu Glu Pro Val Met Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
            580                 585                 590

Cys Phe
```

```
<210> SEQ ID NO 5
<211> LENGTH: 1786
<212> TYPE: DNA
<213> ORGANISM: Trichoplusia ni

<400> SEQUENCE: 5
atgggctcta gcctggacga cgagcacatc ctgagcgccc tgctgcagag cgacgacgaa        60
ctggtgggcg aggacagcga cagcgagatc agcgaccacg tgtccgagga cgacgtgcag       120
tccgacaccg aggaagcctt catcgacgag gtgcacgaag tgcagcctac cagcagcggc       180
tccgagatcc tggacgagca gaacgtgatc gagcagcctg gcagctccct ggccagcaac       240
agaatcctga ccctgcccca gagaaccatc agaggcaaga caagcactg ctggtccacc       300 tccaagagca ccaggcggag cagagtgtcc gccctgaaca tcgtgcggag ccagggggc       360 cccaccagaa tgtgcagaaa catctacgac cccctgctgt gcttcaagct gttcttcacc       420
gacgagatca tcagcgagat cgtgaagtgg accaacgccg agatcagcct gaagaggcgg       480
gagagcatga ccgcgccac cttcagagac accaacgagg acgagatcta cgccttcttc       540
ggcatcctgg tgatgaccgc cgtgagaaag gacaaccaca tgagcaccga cgacctgttc       600
gacagatccc tgagcatggt gtacgtgtcc gtgatgagca gagacagatt cgacttcctg       660
atcagatgcc tgagaatgga cgacaagagc atcagaccca ccctgcggga gaacgacgtg       720
ttcaccccgg tgcggaagct gtgggacctg ttcatccacc agtgcatcca gaactacacc       780
cctggcgccc acctgaccat cgatgagcag ctgctgggct tcagaggcag atgcccttc       840 agaatgtaca tccccaacaa gcccagcaag tacggcatca agatcctgat gatgtgcgac       900
agcggcacca agtacatgat caacggcatg ccctacctgg gcagaggcac ccagacaaac       960
ggcgtgcccc tgggcgagta ctacgtgaaa gaactgagca gcctgtgca tggcagctgc      1020 aggaacatca cctgcgacaa ctggttcacc agcatcccc tggccaagaa cctgctgcag      1080
gaaccctaca gctgaccat cgtgggcacc gtgcggagca acaagcggga gatcccagag      1140
gtgctgaaga acagcagatc cagacctgtg ggaacaagca tgttctgctt cgacggcccc      1200
ctgaccctgg tgtcctacaa gcccaagccc gccaagatgg tgtacctgct gtccagctgc      1260
gacgaggacg ccagcatcaa cgagagcacc ggcaagcccc agatggtgat gtactacaac      1320
cagaccaagg gcggcgtgga caccctggac cagatgtgca gcgtgatgac ctgcagcaga      1380
aagaccaaca gatggcccat ggccctgctg tacggcatga tcaatatcgc ctgcatcaac      1440
agcttcatca tctacagcca caacgtgtcc agcaagggcg agaaggtgca gagccggaag      1500
aaattcatgc ggaacctgta catgagcctg acctccagct tcatgagaaa gagactggaa      1560
```

```
gccccaccc tgaagagata cctgcgggac aacatcagca acatcctgcc caacgaagtg    1620
ccaggaacaa gcgacgacag caccgaggaa cccgtgatga agaagaggac ctactgcacc    1680
tactgtccca gcaagatcag aagaaaggcc aacgccagct gcaagaaatg caaaaaagtg    1740
atctgccggg agcacaacat cgacatgtgc cagagctgtt tctagc                   1786
```

<210> SEQ ID NO 6
<211> LENGTH: 594
<212> TYPE: PRT
<213> ORGANISM: Trichoplusia ni

<400> SEQUENCE: 6

```
Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
                20                  25                  30

His Val Ser Glu Asp Asp Val Gln Ser Asp Thr Glu Glu Ala Phe Ile
            35                  40                  45

Asp Glu Val His Glu Val Gln Pro Thr Ser Ser Gly Ser Glu Ile Leu
        50                  55                  60

Asp Glu Gln Asn Val Ile Glu Gln Pro Gly Ser Ser Leu Ala Ser Asn
65                  70                  75                  80

Arg Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn Ile Val Arg Ser Gln Arg Gly Pro Thr Arg Met Cys Arg Asn Ile
            115                 120                 125

Tyr Asp Pro Leu Leu Cys Phe Lys Leu Phe Phe Thr Asp Glu Ile Ile
        130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
            195                 200                 205

Val Ser Val Met Ser Arg Asp Arg Phe Asp Phe Leu Ile Arg Cys Leu
        210                 215                 220

Arg Met Asp Asp Lys Ser Ile Arg Pro Thr Leu Arg Glu Asn Asp Val
225                 230                 235                 240

Phe Thr Pro Val Arg Lys Leu Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
            275                 280                 285

Ser Lys Tyr Gly Ile Lys Ile Leu Met Met Cys Asp Ser Gly Thr Lys
        290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335
```

```
His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
            355                 360                 365

Gly Thr Val Arg Ser Asn Lys Arg Glu Ile Pro Glu Val Leu Lys Asn
    370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
            435                 440                 445

Leu Asp Gln Met Cys Ser Val Met Thr Cys Ser Arg Lys Thr Asn Arg
    450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
            515                 520                 525

Arg Asp Asn Ile Ser Asn Ile Leu Pro Asn Glu Val Pro Gly Thr Ser
    530                 535                 540

Asp Asp Ser Thr Glu Glu Pro Val Met Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
            580                 585                 590

Cys Phe
```

<210> SEQ ID NO 7
<211> LENGTH: 1786
<212> TYPE: DNA
<213> ORGANISM: Trichoplusia ni

<400> SEQUENCE: 7

```
atgggctcta gcctggacga cgagcacatc ctgagcgccc tgctgcagag cgacgacgaa      60
ctggtgggcg aggacagcga cagcgagatc agcgaccacg tgtccgagga cgacgtgcag     120
tccgacaccg aggaagcctt catcgacgag gtgcacgaag tgcagcctac cagcagcggc     180
tccgagatcc tggacgagca gaacgtgatc gagcagcctg gcagctccct ggccagcaac     240
agaatcctga ccctgcccca gagaaccatc agaggcaaga caagcactg ctggtccacc     300 tccaagagca ccaggcggag cagagtgtcc gccctgaaca tcgtgcggag ccagaggggc     360
cccaccagaa tgtgcagaaa catctacgac ccctgctgt gcttcaagct gttcttcacc     420
gacgagatca tcagcgagat cgtgaagtgg accaacgccg agatcagcct gaagaggcgg     480
gagagcatga ccggcgccac cttcagagac accaacgagg acgagatcta cgccttcttc     540
ggcatcctgg tgatgaccgc cgtgagaaag gacaaccaca tgagcaccga cgacctgttc     600
```

-continued

```
gacagatccc tgagcatggt gtacgtgtcc gtgatgagca gagacagatt cgacttcctg      660
atcagatgcc tgagaatgga cgacaagagc atcagaccca ccctgcggga gaacgacgtg      720
ttcacccccg tgcggaagat ctgggacctg ttcatccacc agtgcatcca gaactacacc      780
cctggcgccc acctgaccat cgatgagcag ctgctgggct tcagaggcag atgcccttc      840 agaatgtaca tccccaacaa gcccagcaag tacggcatca agatcctgat gatgtgcgac      900
agcggcacca agtacatgat caacggcatg ccctacctgg gcagaggcac ccagacaaac      960
ggcgtgcccc tgggcgagta ctacgtgaaa gaactgagca agcctgtgca tggcagctgc      1020
aggaacatca cctgcgacaa ctggttcacc agcatccccc tggccaagaa cctgctgcag      1080
gaaccctaca agctgaccat cgtgggcacc gtgcggagca caagcgggga tcccagag       1140 gtgctgaaga acagcagatc cagacctgtg ggaacaagca tgttctgctt cgacggcccc      1200
ctgaccctgg tgtcctacaa gcccaagccc gccaagatgg tgtacctgct gtccagctgc      1260
gacgaggacg ccagcatcaa cgagagcacc ggcaagcccc agatggtgat gtactacaac      1320
cagaccaagg gcggcgtgga caccctggac cagatgtgca gcgtgatgac ctgcagcaga      1380
aagaccaaca gatggcccat ggccctgctg tacggcatga tcaatatcgc ctgcatcaac      1440
agcttcatca tctacagcca caacgtgtcc agcaagggcg agaaggtgca gagccggaag      1500
aaattcatgc ggaacctgta catgagcctg acctccagct tcatgagaaa gagactggaa      1560 gccccaccc tgaagagata cctgcgggac aacatcacca acatcctgcc caacgaagtg      1620
ccaggaacaa gcgacgacag caccgaggaa cccgtgatga agaagaggac ctactgcacc      1680
tactgtccca gcaagatcag aagaaaggcc aacgccagct gcaagaaatg caaaaaagtg      1740
atctgccggg agcacaacat cgacatgtgc cagagctgtt tctagc                    1786
```

```
<210> SEQ ID NO 8
<211> LENGTH: 594
<212> TYPE: PRT
<213> ORGANISM: Trichoplusia ni

<400> SEQUENCE: 8

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
            20                  25                  30

His Val Ser Glu Asp Asp Val Gln Ser Asp Thr Glu Glu Ala Phe Ile
        35                  40                  45

Asp Glu Val His Glu Val Gln Pro Thr Ser Ser Gly Ser Glu Ile Leu
    50                  55                  60

Asp Glu Gln Asn Val Ile Glu Gln Pro Gly Ser Ser Leu Ala Ser Asn
65                  70                  75                  80

Arg Ile Leu Thr Leu Pro Gln Arg Thr Ile Arg Gly Lys Asn Lys His
            85                  90                  95

Cys Trp Ser Thr Ser Lys Ser Thr Arg Arg Ser Arg Val Ser Ala Leu
            100                 105                 110

Asn Ile Val Arg Ser Gln Arg Gly Pro Thr Arg Met Cys Arg Asn Ile
        115                 120                 125

Tyr Asp Pro Leu Leu Cys Phe Lys Leu Phe Phe Thr Asp Glu Ile Ile
    130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
```

-continued

```
                   165              170              175

Tyr Ala Phe Phe Gly Ile Leu Val Met Thr Ala Val Arg Lys Asp Asn
            180              185              190

His Met Ser Thr Asp Asp Leu Phe Asp Arg Ser Leu Ser Met Val Tyr
            195              200              205

Val Ser Val Met Ser Arg Asp Arg Phe Asp Phe Leu Ile Arg Cys Leu
    210              215              220

Arg Met Asp Asp Lys Ser Ile Arg Pro Thr Leu Arg Glu Asn Asp Val
225              230              235              240

Phe Thr Pro Val Arg Lys Ile Trp Asp Leu Phe Ile His Gln Cys Ile
            245              250              255

Gln Asn Tyr Thr Pro Gly Ala His Leu Thr Ile Asp Glu Gln Leu Leu
            260              265              270

Gly Phe Arg Gly Arg Cys Pro Phe Arg Met Tyr Ile Pro Asn Lys Pro
            275              280              285

Ser Lys Tyr Gly Ile Lys Ile Leu Met Met Cys Asp Ser Gly Thr Lys
            290              295              300

Tyr Met Ile Asn Gly Met Pro Tyr Leu Gly Arg Gly Thr Gln Thr Asn
305              310              315              320

Gly Val Pro Leu Gly Glu Tyr Tyr Val Lys Glu Leu Ser Lys Pro Val
            325              330              335

His Gly Ser Cys Arg Asn Ile Thr Cys Asp Asn Trp Phe Thr Ser Ile
            340              345              350

Pro Leu Ala Lys Asn Leu Leu Gln Glu Pro Tyr Lys Leu Thr Ile Val
            355              360              365

Gly Thr Val Arg Ser Asn Lys Arg Glu Ile Pro Glu Val Leu Lys Asn
            370              375              380

Ser Arg Ser Arg Pro Val Gly Thr Ser Met Phe Cys Phe Asp Gly Pro
385              390              395              400

Leu Thr Leu Val Ser Tyr Lys Pro Lys Pro Ala Lys Met Val Tyr Leu
            405              410              415

Leu Ser Ser Cys Asp Glu Asp Ala Ser Ile Asn Glu Ser Thr Gly Lys
            420              425              430

Pro Gln Met Val Met Tyr Tyr Asn Gln Thr Lys Gly Gly Val Asp Thr
            435              440              445

Leu Asp Gln Met Cys Ser Val Met Thr Cys Ser Arg Lys Thr Asn Arg
    450              455              460

Trp Pro Met Ala Leu Leu Tyr Gly Met Ile Asn Ile Ala Cys Ile Asn
465              470              475              480

Ser Phe Ile Ile Tyr Ser His Asn Val Ser Ser Lys Gly Glu Lys Val
            485              490              495

Gln Ser Arg Lys Lys Phe Met Arg Asn Leu Tyr Met Ser Leu Thr Ser
            500              505              510

Ser Phe Met Arg Lys Arg Leu Glu Ala Pro Thr Leu Lys Arg Tyr Leu
            515              520              525

Arg Asp Asn Ile Thr Asn Ile Leu Pro Asn Glu Val Pro Gly Thr Ser
    530              535              540

Asp Asp Ser Thr Glu Glu Pro Val Met Lys Lys Arg Thr Tyr Cys Thr
545              550              555              560

Tyr Cys Pro Ser Lys Ile Arg Arg Lys Ala Asn Ala Ser Cys Lys Lys
            565              570              575

Cys Lys Lys Val Ile Cys Arg Glu His Asn Ile Asp Met Cys Gln Ser
            580              585              590
```

-continued

Cys Phe

<210> SEQ ID NO 9
<211> LENGTH: 1786
<212> TYPE: DNA
<213> ORGANISM: Trichoplusia ni

<400> SEQUENCE: 9
atgggctcta gcctggacga cgagcacatc ctgagcgccc tgctgcagag cgacgacgaa      60
ctggtgggcg aggacagcga cagcgagatc agcgaccacg tgtccgagga cgacgtgcag     120
tccgacaccg aggaagcctt catcgacgag gtgcacgaag tgcagcctac cagcagcggc     180
tccgagatcc tggacgagca gaacgtgatc gagcagcctg gcagctccct ggccagcaac     240
agaatcctga ccctgcccca gagaaccatc agaggcaaga caagcactg ctggtccacc     300 tccaagagca ccaggcggag cagagtgtcc gccctgaaca tcgtgcggag ccagaggggc     360
cccaccagaa tgtgcagaaa catctacgac cccctgctgt gcttcaagct gttcttcacc     420
gacgagatca tcagcgagct ggtgaagtgg accaacgccg agatcagcct gaagaggcgg     480
gagagcatga ccggcgccac cttcagagac accaacgagg acgagatcta cgccttcttc     540
ggcatcctgg tgatgaccgc cgtgagaaag gacaaccaca tgagcaccga cgacctgttc     600
gacagatccc tgagcatggt gtacgtgtcc gtgatgagca gagacagatt cgacttcctg     660
atcagatgcc tgagaatgga cgacaagagc atcagaccca ccctgcggga gaacgacgtg     720
ttcacccccg tgcggaagct gtgggacctg ttcatccacc agtgcatcca gaactacacc     780
cctggcgccc acctgaccat cgatgagcag ctgctgggct tcagaggcag atgccccttc     840
agaatgtaca tccccaacaa gcccagcaag tacggcatca agatcctgat gatgtgcgac     900
agcggcacca agtacatgat caacggcatg ccctacctgg gcagaggcac ccagacaaac     960
ggcgtgcccc tgggcgagta ctacgtgaaa gaactgagca agcctgtgca tggcagctgc    1020
aggaacatca cctgcgacaa ctggttcacc agcatccccc tggccaagaa cctgctgcag    1080
gaaccctaca gctgaccat cgtgggcacc gtgcggagca caagcggga gatcccagag    1140 gtgctgaaga acagcagatc cagacctgtg ggaacaagca tgttctgctt cgacggcccc    1200
ctgaccctgg tgtcctacaa gcccaagccc gccaagatgg tgtacctgct gtccagctgc    1260
gacgaggacg ccagcatcaa cgagagcacc ggcaagcccc agatggtgat gtactacaac    1320
cagaccaagg cggcgtgga caccctggac cagatgtgca gcgtgatgac ctgcagcaga    1380
aagaccaaca gatggcccat ggccctgctg tacggcatga tcaatatcgc ctgcatcaac    1440
agcttcatca tctacagcca caacgtgtcc agcaagggcg agaaggtgca gagccggaag    1500
aaattcatgc ggaacctgta catgagcctg acctccagct tcatgagaaa gagactggaa    1560
gcccccaccc tgaagagata cctgcgggac aacatcacca acatcctgcc caacgaagtg    1620
ccaggaacaa gcgacgacag caccgaggaa cccgtgatga agaagaggac ctactgcacc    1680
tactgtccca gcaagatcag aagaaaggcc aacgccagct gcaagaaatg caaaaaagtg    1740
atctgccggg agcacaacat cgacatgtgc cagagctgtt ctagc                    1786

<210> SEQ ID NO 10
<211> LENGTH: 594
<212> TYPE: PRT
<213> ORGANISM: Trichoplusia ni

<400> SEQUENCE: 10

-continued

```
Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
            20                  25                  30

His Val Ser Glu Asp Asp Val Gln Ser Asp Thr Glu Glu Ala Phe Ile
            35                  40                  45

Asp Glu Val His Glu Val Gln Pro Thr Ser Ser Gly Ser Glu Ile Leu
    50                  55                  60

Asp Glu Gln Asn Val Ile Glu Gln Pro Gly Ser Ser Leu Ala Ser Asn
65                  70                  75                  80

Arg Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn Ile Val Arg Ser Gln Arg Gly Pro Thr Arg Met Cys Arg Asn Ile
            115                 120                 125

Tyr Asp Pro Leu Leu Cys Phe Lys Leu Phe Phe Thr Asp Glu Ile Ile
    130                 135                 140

Ser Glu Leu Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
            195                 200                 205

Val Ser Val Met Ser Arg Asp Arg Phe Asp Phe Leu Ile Arg Cys Leu
    210                 215                 220

Arg Met Asp Asp Lys Ser Ile Arg Pro Thr Leu Arg Glu Asn Asp Val
225                 230                 235                 240

Phe Thr Pro Val Arg Lys Leu Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
            275                 280                 285

Ser Lys Tyr Gly Ile Lys Ile Leu Met Met Cys Asp Ser Gly Thr Lys
    290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
            325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
            355                 360                 365

Gly Thr Val Arg Ser Asn Lys Arg Glu Ile Pro Glu Val Leu Lys Asn
    370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
            405                 410                 415

Leu Ser Ser Cys Asp Glu Asp Ala Ser Ile Asn Glu Ser Thr Gly Lys
```

-continued

```
                   420              425              430

Pro Gln Met Val Met Tyr Tyr Asn Gln Thr Lys Gly Gly Val Asp Thr
        435              440              445

Leu Asp Gln Met Cys Ser Val Met Thr Cys Ser Arg Lys Thr Asn Arg
        450              455              460

Trp Pro Met Ala Leu Leu Tyr Gly Met Ile Asn Ile Ala Cys Ile Asn
465              470              475              480

Ser Phe Ile Ile Tyr Ser His Asn Val Ser Ser Lys Gly Glu Lys Val
            485              490              495

Gln Ser Arg Lys Lys Phe Met Arg Asn Leu Tyr Met Ser Leu Thr Ser
        500              505              510

Ser Phe Met Arg Lys Arg Leu Glu Ala Pro Thr Leu Lys Arg Tyr Leu
        515              520              525

Arg Asp Asn Ile Thr Asn Ile Leu Pro Asn Glu Val Pro Gly Thr Ser
        530              535              540

Asp Asp Ser Thr Glu Glu Pro Val Met Lys Lys Arg Thr Tyr Cys Thr
545              550              555              560

Tyr Cys Pro Ser Lys Ile Arg Arg Lys Ala Asn Ala Ser Cys Lys Lys
            565              570              575

Cys Lys Lys Val Ile Cys Arg Glu His Asn Ile Asp Met Cys Gln Ser
        580              585              590

Cys Phe
```

```
<210> SEQ ID NO 11
<211> LENGTH: 1786
<212> TYPE: DNA
<213> ORGANISM: Trichoplusia ni

<400> SEQUENCE: 11
atgggctcta gcctggacga cgagcacatc ctgagcgccc tgctgcagag cgacgacgaa     60
ctggtgggcg aggacagcga cagcgagatc agcgaccacg tgtccgagga cgacgtgcag    120
tccgacaccg aggaagcctt catcgacgag gtgcacgaag tgcagcctac cagcagcggc    180
tccgagatcc tggacgagca gaacgtgatc gagcagcctg gcagctccct ggccagcaac    240
agaatcctga ccctgcccca gagaaccatc agaggcaaga acaagcactg ctggtccacc    300
tccaagagca ccaggcggag cagagtgtcc gccctgaaca tcgtgcggag ccagaggggc    360
cccaccagaa tgtgcagaaa catctacgac cccctgctgt gcttcaagct gttcttcacc    420
gacgagatca tcagcgagat cgtgaagtgg accaacgccg agatcagcct gaagaggcgg    480
gagagcatga ccggcgccac cttcagagac accaacgagg acgagatcta cgccttcttc    540
ggcatcctgg tgatgaccgc cgtgagaaag gacaaccaca tgagcaccga cgacctgttc    600
gacagatccc tgagcatggt gtacgtgtcc gtgatgagca gagacagatt cgacttcctg    660
atcagatgcc tgagaatgga cgacaagagc atcagaccca ccctgcggga gaacgacgtg    720
ttcacccccg tgcggaagct gtgggacctg ttcatccacc agtgcatcca gaactacacc    780
cctggcgccc acctgaccat cgatgagcag ctgctgggct tcagaggcag atgcccctc    840 agaatgtaca tccccaacaa gcccagcaag tacggcatca gatcctgat gatgtgcgac    900 agcggcacca gtacatgat caacggcatg ccctacctgg gcagaggcac ccagacaaac    960
ggcgtgcccc tgggcgagta ctacgtgaaa gaactgagca gcctgtgca tggcagctgc   1020 aggaacatca cctgcgacaa ctggttcacc agcatccccc tggccaagaa cctgctgcag   1080
gaaccctaca agctgaccat cgtgggcacc gtgcggagca acaagcggga gatcccagag   1140
```

-continued

```
gtgctgaaga acagcagatc cagacctgtg ggaacaagca tgttctgctt cgacggcccc       1200
ctgaccctgg tgtcctacaa gcccaagccc gccaagatgg tgtacctgct gtccagctgc       1260
gacgaggacg ccagcatcaa cgagagcacc ggcaagcccc agatggtgat gtactacaac       1320
cagaccaagg gcggcgtgga caccctggac cagatgtgca gcgtgatgac ctgcagcaga       1380
aagaccaaca gatggcccat ggccctgctg tacggcatga tcaatatcgc ctgcatcaac       1440
agcttcatca tctacagcca caacgtgtcc agcaagggcg agaaggtgca gagccggaag       1500
aaattcatgc ggaacctgta catgagcctg acctccagct tcatgagaaa gagactggaa       1560
gcccccaccc tgaagagata cctgcgggac aacatcacca acatcctgcc caacgaagtg       1620
ccaggaacaa gcgacgacag caccgaggaa cccgtgatga agaagaggac ctactgcacc       1680
tactgtccca gcaagatcag aagaaaggcc aacgccagct gcaagaaatg caaaaaagtg       1740
atctgccggg agcacaacat cgacatgtgc cagagctgtt tctagc                      1786
```

```
<210> SEQ ID NO 12
<211> LENGTH: 594
<212> TYPE: PRT
<213> ORGANISM: Trichoplusia ni

<400> SEQUENCE: 12

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
                20                  25                  30

His Val Ser Glu Asp Asp Val Gln Ser Asp Thr Glu Glu Ala Phe Ile
            35                  40                  45

Asp Glu Val His Glu Val Gln Pro Thr Ser Ser Gly Ser Glu Ile Leu
        50                  55                  60

Asp Glu Gln Asn Val Ile Glu Gln Pro Gly Ser Ser Leu Ala Ser Asn
65                  70                  75                  80

Arg Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn Ile Val Arg Ser Gln Arg Gly Pro Thr Arg Met Cys Arg Asn Ile
        115                 120                 125

Tyr Asp Pro Leu Leu Cys Phe Lys Leu Phe Phe Thr Asp Glu Ile Ile
    130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
    210                 215                 220

Arg Met Asp Asp Lys Ser Ile Arg Pro Thr Leu Arg Glu Asn Asp Val
225                 230                 235                 240

Phe Thr Pro Val Arg Lys Leu Trp Asp Leu Phe Ile His Gln Cys Ile
                245                 250                 255
```

-continued

```
Gln Asn Tyr Thr Pro Gly Ala His Leu Thr Ile Asp Glu Gln Leu Leu
            260             265             270

Gly Phe Arg Gly Arg Cys Pro Phe Arg Met Tyr Ile Pro Asn Lys Pro
            275             280             285

Ser Lys Tyr Gly Ile Lys Ile Leu Met Met Cys Asp Ser Gly Thr Lys
            290             295             300

Tyr Met Ile Asn Gly Met Pro Tyr Leu Gly Arg Gly Thr Gln Thr Asn
305             310             315             320

Gly Val Pro Leu Gly Glu Tyr Tyr Val Lys Glu Leu Ser Lys Pro Val
            325             330             335

His Gly Ser Cys Arg Asn Ile Thr Cys Asp Asn Trp Phe Thr Ser Ile
            340             345             350

Pro Leu Ala Lys Asn Leu Leu Gln Glu Pro Tyr Lys Leu Thr Ile Val
            355             360             365

Gly Thr Val Arg Ser Asn Lys Arg Glu Ile Pro Glu Val Leu Lys Asn
370             375             380

Ser Arg Ser Arg Pro Val Gly Thr Ser Met Phe Cys Phe Asp Gly Pro
385             390             395             400

Leu Thr Leu Val Ser Tyr Lys Pro Lys Pro Ala Lys Met Val Tyr Leu
            405             410             415

Leu Ser Ser Cys Asp Glu Asp Ala Ser Ile Asn Glu Ser Thr Gly Lys
            420             425             430

Pro Gln Met Val Met Tyr Tyr Asn Gln Thr Lys Gly Gly Val Asp Thr
            435             440             445

Leu Asp Gln Met Cys Ser Val Met Thr Cys Ser Arg Lys Thr Asn Arg
            450             455             460

Trp Pro Met Ala Leu Leu Tyr Gly Met Ile Asn Ile Ala Cys Ile Asn
465             470             475             480

Ser Phe Ile Ile Tyr Ser His Asn Val Ser Ser Lys Gly Glu Lys Val
            485             490             495

Gln Ser Arg Lys Lys Phe Met Arg Asn Leu Tyr Met Ser Leu Thr Ser
            500             505             510

Ser Phe Met Arg Lys Arg Leu Glu Ala Pro Thr Leu Lys Arg Tyr Leu
            515             520             525

Arg Asp Asn Ile Thr Asn Ile Leu Pro Asn Glu Val Pro Gly Thr Ser
            530             535             540

Asp Asp Ser Thr Glu Glu Pro Val Met Lys Lys Arg Thr Tyr Cys Thr
545             550             555             560

Tyr Cys Pro Ser Lys Ile Arg Arg Lys Ala Asn Ala Ser Cys Lys Lys
            565             570             575

Cys Lys Lys Val Ile Cys Arg Glu His Asn Ile Asp Met Cys Gln Ser
            580             585             590

Cys Phe
```

<210> SEQ ID NO 13
<211> LENGTH: 1786
<212> TYPE: DNA
<213> ORGANISM: Trichoplusia ni

<400> SEQUENCE: 13

```
atgggctcta gcctggacga cgagcacatc ctgagcgccc tgctgcagag cgacgacgaa      60
ctggtgggcg aggacagcga cagcgagatc agcgaccacg tgtccgagga cgacgtgcag     120
tccgacaccg aggaagcctt catcgacgag gtgcacgaag tgcagcctac cagcagcggc     180
```

-continued

```
tccgagatcc tggacgagca gaacgtgatc gagcagcctg gcagctccct ggccagcaac      240
agaatcctga ccctgcccca gagaaccatc agaggcaaga acaagcactg ctggtccacc      300
tccaagagca ccaggcggag cagagtgtcc gccctgaaca tcgtgcggag ccagaggggc      360
cccaccagaa tgtgcagaaa catctacgac cccctgctgt gcttcaagct gttcttcacc      420
gacgagatca tcagcgagct ggtgaagtgg accaacgccg agatcagcct gaagaggcgg      480
gagagcatga ccgcgccac cttcagagac accaacgagg acgagatcta cgccttcttc      540
ggcatcctgg tgatgaccgc cgtgagaaag gacaaccaca tgagcaccga cgacctgttc      600
gacagatccc tgagcatggt gtacgtgtcc gtgatgagca gagacagatt cgacttcctg      660
atcagatgcc tgagaatgga cgacaagagc atcagaccca ccctgcggga gaacgacgtg      720
ttcacccccg tgcggaagat ctgggacctg ttcatccacc agtgcatcca gaactacacc      780
cctggcgccc acctgaccat cgatgagcag ctgctgggct tcagaggcag atgccccttc      840
agaatgtaca tccccaacaa gcccagcaag tacggcatca agatcctgat gatgtgcgac      900
agcggcacca agtacatgat caacggcatg ccctacctgg gcagaggcac ccagacaaac      960
ggcgtgcccc tgggcgagta ctacgtgaaa gaactgagca agcctgtgca tggcagctgc      1020
aggaacatca cctgcgacaa ctggttcacc agcatccccc tggccaagaa cctgctgcag      1080
gaaccctaca agctgaccat cgtgggcacc gtgcggagca acaagcggga tcccagag      1140 gtgctgaaga acagcagatc cagacctgtg ggaacaagca tgttctgctt cgacggcccc      1200
ctgaccctgg tgtcctacaa gcccaagccc gccaagatgg tgtacctgct gtccagctgc      1260
gacgaggacg ccagcatcaa cgagagcacc ggcaagcccc agatggtgat gtactacaac      1320
cagaccaagg cggcgtgga caccctggac cagatgtgca gcgtgatgac ctgcagcaga      1380
aagaccaaca gatggcccat ggccctgctg tacggcatga tcaatatcgc ctgcatcaac      1440
agcttcatca tctacagcca caacgtgtcc agcaagggcg agaaggtgca gagccggaag      1500
aaattcatgc ggaacctgta catgagcctg acctccagct tcatgagaaa gagactggaa      1560
gcccccaccc tgaagagata cctgcgggac aacatcacca acatcctgcc caacgaagtg      1620
ccaggaacaa gcgacgacag caccgaggaa cccgtgatga agaagaggac ctactgcacc      1680
tactgtccca gcaagatcag aagaaaggcc aacgccagct gcaagaaatg caaaaaagtg      1740
atctgccggg agcacaacat cgacatgtgc cagagctgtt tctagc      1786
```

```
<210> SEQ ID NO 14
<211> LENGTH: 594
<212> TYPE: PRT
<213> ORGANISM: Trichoplusia ni

<400> SEQUENCE: 14

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
            20                  25                  30

His Val Ser Glu Asp Asp Val Gln Ser Asp Thr Glu Glu Ala Phe Ile
        35                  40                  45

Asp Glu Val His Glu Val Gln Pro Thr Ser Ser Gly Ser Glu Ile Leu
        50                  55                  60

Asp Glu Gln Asn Val Ile Glu Gln Pro Gly Ser Ser Leu Ala Ser Asn
65                  70                  75                  80

Arg Ile Leu Thr Leu Pro Gln Arg Thr Ile Arg Gly Lys Asn Lys His
                85                  90                  95
```

```
Cys Trp Ser Thr Ser Lys Ser Thr Arg Arg Ser Arg Val Ser Ala Leu
            100                 105                 110

Asn Ile Val Arg Ser Gln Arg Gly Pro Thr Arg Met Cys Arg Asn Ile
            115                 120                 125

Tyr Asp Pro Leu Leu Cys Phe Lys Leu Phe Phe Thr Asp Glu Ile Ile
            130                 135                 140

Ser Glu Leu Val Lys Trp Thr Asn Ala Glu Ile Ser Leu Lys Arg Arg
        145                 150                 155                 160

Glu Ser Met Thr Gly Ala Thr Phe Arg Asp Thr Asn Glu Asp Glu Ile
                    165                 170                 175

Tyr Ala Phe Phe Gly Ile Leu Val Met Thr Ala Val Arg Lys Asp Asn
                180                 185                 190

His Met Ser Thr Asp Asp Leu Phe Asp Arg Ser Leu Ser Met Val Tyr
                195                 200                 205

Val Ser Val Met Ser Arg Asp Arg Phe Asp Phe Leu Ile Arg Cys Leu
            210                 215                 220

Arg Met Asp Asp Lys Ser Ile Arg Pro Thr Leu Arg Glu Asn Asp Val
        225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
                260                 265                 270

Gly Phe Arg Gly Arg Cys Pro Phe Arg Met Tyr Ile Pro Asn Lys Pro
                275                 280                 285

Ser Lys Tyr Gly Ile Lys Ile Leu Met Met Cys Asp Ser Gly Thr Lys
            290                 295                 300

Tyr Met Ile Asn Gly Met Pro Tyr Leu Gly Arg Gly Thr Gln Thr Asn
        305                 310                 315                 320

Gly Val Pro Leu Gly Glu Tyr Tyr Val Lys Glu Leu Ser Lys Pro Val
                    325                 330                 335

His Gly Ser Cys Arg Asn Ile Thr Cys Asp Asn Trp Phe Thr Ser Ile
                340                 345                 350

Pro Leu Ala Lys Asn Leu Leu Gln Glu Pro Tyr Lys Leu Thr Ile Val
                355                 360                 365

Gly Thr Val Arg Ser Asn Lys Arg Glu Ile Pro Glu Val Leu Lys Asn
        370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
                420                 425                 430

Pro Gln Met Val Met Tyr Tyr Asn Gln Thr Lys Gly Gly Val Asp Thr
            435                 440                 445

Leu Asp Gln Met Cys Ser Val Met Thr Cys Ser Arg Lys Thr Asn Arg
        450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Ser Leu Thr Ser
            500                 505                 510
```

-continued

```
Ser Phe Met Arg Lys Arg Leu Glu Ala Pro Thr Leu Lys Arg Tyr Leu
        515                 520                 525

Arg Asp Asn Ile Thr Asn Ile Leu Pro Asn Glu Val Pro Gly Thr Ser
        530                 535                 540

Asp Asp Ser Thr Glu Glu Pro Val Met Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
                580                 585                 590

Cys Phe

<210> SEQ ID NO 15
<211> LENGTH: 1786
<212> TYPE: DNA
<213> ORGANISM: Trichoplusia ni

<400> SEQUENCE: 15
atgggctcta gcctggacga cgagcacatc ctgagcgccc tgctgcagag cgacgacgaa          60
ctggtgggcg aggacagcga cagcgagatc agcgaccacg tgtccgagga cgacgtgcag         120
tccgacaccg aggaagcctt catcgacgag gtgcacgaag tgcagcctac cagcagcggc         180
tccgagatcc tggacgagca gaacgtgatc gagcagcctg cagctccct ggccagcaac          240 agaatcctga ccctgcccca gagaaccatc agaggcaaga caagcactg ctggtccacc          300 tccaagagca ccaggcggag cagagtgtcc gccctgaaca tcgtgcggag ccagagggc          360 cccaccagaa tgtgcagaaa catctacgac cccctgctgt gcttcaagct gttcttcacc         420
gacgagatca tcagcgagct ggtgaagtgg accaacgccg agatcagcct gaagaggcgg         480
gagagcatga ccggcgccac cttcagagac accaacgagg acgagatcta cgccttcttc         540
ggcatcctgg tgatgaccgc cgtgagaaag gacaaccaca tgagcaccga cgacctgttc         600
gacagatccc tgagcatggt gtacgtgtcc gtgatgagca gagacagatt cgacttcctg         660
atcagatgcc tgagaatgga cgacaagagc atcagaccca ccctgcggga gaacgacgtg         720
ttcacccccg tgcggaagct gtgggacctg ttcatccacc agtgcatcca gaactacacc         780
cctggcgccc acctgaccat cgatgagcag ctgctgggct tcagaggcag atgcccttc          840 agaatgtaca tccccaacaa gcccagcaag tacggcatca gatcctgat gatgtgcgac          900 agcggcacca gtacatgat caacggcatg ccctacctgg gcagaggcac ccagacaaac          960
ggcgtgcccc tgggcgagta ctacgtgaaa gaactgagca gcctgtgca tggcagctgc         1020 aggaacatca cctgcgacaa ctggttcacc agcatccccc tggccaagaa cctgctgcag        1080
gaaccctaca gctgaccat cgtgggcacc gtgcggagca caagcggga gatcccagag          1140 gtgctgaaga acagcagatc cagacctgtg ggaacaagca tgttctgctt cgacggcccc        1200
ctgaccctgg tgtcctacaa gcccaagccc gccaagatgg tgtacctgct gtccagctgc        1260
gacgaggacg ccagcatcaa cgagagcacc ggcaagcccc agatggtgat gtactacaac        1320
cagaccaagg cggcgtgga cacctggac cagatgtgca gcgtgatgac ctgcagcaga          1380
aagaccaaca gatggcccat ggccctgctg tacggcatga tcaatatcgc ctgcatcaac        1440
agcttcatca tctacagcca acgtgtcc agcaagggcg agaaggtgca gagccggaag          1500
aaattcatgc ggaacctgta catgagcctg acctccagct tcatgagaaa gagactggaa        1560
gcccccaccc tgaagagata cctgcgggac aacatcagca catcctgcc caacgaagtg        1620
```

-continued

```
ccaggaacaa gcgacgacag caccgaggaa cccgtgatga agaagaggac ctactgcacc    1680
tactgtccca gcaagatcag aagaaaggcc aacgccagct gcaagaaatg caaaaaagtg    1740
atctgccggg agcacaacat cgacatgtgc cagagctgtt tctagc                   1786

<210> SEQ ID NO 16
<211> LENGTH: 594
<212> TYPE: PRT
<213> ORGANISM: Trichoplusia ni

<400> SEQUENCE: 16

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
                20                  25                  30

His Val Ser Glu Asp Asp Val Gln Ser Asp Thr Glu Glu Ala Phe Ile
            35                  40                  45

Asp Glu Val His Glu Val Gln Pro Thr Ser Ser Gly Ser Glu Ile Leu
        50                  55                  60

Asp Glu Gln Asn Val Ile Glu Gln Pro Gly Ser Ser Leu Ala Ser Asn
65                  70                  75                  80

Arg Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn Ile Val Arg Ser Gln Arg Gly Pro Thr Arg Met Cys Arg Asn Ile
            115                 120                 125

Tyr Asp Pro Leu Leu Cys Phe Lys Leu Phe Phe Thr Asp Glu Ile Ile
        130                 135                 140

Ser Glu Leu Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
        210                 215                 220

Arg Met Asp Asp Lys Ser Ile Arg Pro Thr Leu Arg Glu Asn Asp Val
225                 230                 235                 240

Phe Thr Pro Val Arg Lys Leu Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
        275                 280                 285

Ser Lys Tyr Gly Ile Lys Ile Leu Met Met Cys Asp Ser Gly Thr Lys
        290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350
```

```
Pro Leu Ala Lys Asn Leu Leu Gln Glu Pro Tyr Lys Leu Thr Ile Val
        355                 360                 365

Gly Thr Val Arg Ser Asn Lys Arg Glu Ile Pro Glu Val Leu Lys Asn
        370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
                420                 425                 430

Pro Gln Met Val Met Tyr Tyr Asn Gln Thr Lys Gly Gly Val Asp Thr
        435                 440                 445

Leu Asp Gln Met Cys Ser Val Met Thr Cys Ser Arg Lys Thr Asn Arg
        450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Ser Leu Thr Ser
                500                 505                 510

Ser Phe Met Arg Lys Arg Leu Glu Ala Pro Thr Leu Lys Arg Tyr Leu
        515                 520                 525

Arg Asp Asn Ile Ser Asn Ile Leu Pro Asn Glu Val Pro Gly Thr Ser
        530                 535                 540

Asp Asp Ser Thr Glu Glu Pro Val Met Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
                580                 585                 590

Cys Phe
```

```
<210> SEQ ID NO 17
<211> LENGTH: 1786
<212> TYPE: RNA
<213> ORGANISM: Trichoplusia ni

<400> SEQUENCE: 17
augggcucua gccuggacga cgagcacauc cugagcgccc ugcugcagag cgacgacgaa      60 cugguggggcg aggacagcga cagcgagauc agcgaccacg uguccgagga cgacgugcag     120
uccgacaccg aggaagccuu caucgacgag gugcacgaag ugcagccuac cagcagcggc     180
uccgagaucc uggacgagca gaacgugauc gagcagccug gcagcucccu ggccagcaac     240
agaauccuga cccugcccca gagaaccauc agaggcaaga acaagcacug cugguccacc     300
uccaagagca ccaggcggag cagagugucc gcccugaaca ucgugcggag ccagaggggc     360
cccaccagaa ugugcagaaa caucuacgac ccccugcugu gcuucaagcu guucuucacc     420
gacgagauca ucagcgagau cgugaagugg accaacgccg agaucagccu gaagaggcgg     480
gagagcauga ccggcgccac cuucagagac accaacgagg acgagaucua cgccuucuuc     540
ggcauccugg ugaugaccgc cgugagaaag gacaaccaca ugagcaccga cgaccuguuc     600 gacgauccc ugagcauggu guacgugucc gugaugagca gagacagauu cgacuuccug     660
aucagaugcc ugagaaugga cgacaagagc aucagacccca cccugcggga gaacgacgug     720
```

-continued

```
uucaccccg ugcggaagcu guggaccug uucauccacc agugcaucca gaacuacacc      780
ccuggcgccc accugaccau cgaugagcag cugcuggggcu ucagaggcag augccccuuc    840
agaauguaca uccccaacaa gcccagcaag uacggcauca agauccugau gaugugcgac    900
agcggcacca aguacaugau caacggcaug cccuaccugg gcagaggcac ccagacaaac    960
ggcgugcccc ugggcgagua cuacgugaaa gaacugagca agccugugca uggcagcugc    1020
aggaacauca ccugcgacaa cugguucacc agcauccccc uggccaagaa ccugcugcag    1080
gaacccuaca agcugaccau cguggcacc gugcggagca acaagcggga gaucccagag     1140
gugcugaaga acagcagauc cagaccugug ggaacaagca uguucugcuu cgacggcccc    1200
cugacccugg ugucccuacaa gcccaagccc gccaagaugg uguaccugcu guccagcugc    1260
gacgaggacg ccagcaucaa cgagagcacc ggcaagcccc agauggugau guacuacaac    1320
cagaccaagg gcggcgugga caccccuggac cagaugugca gcgugaugac cugcagcaga   1380
aagaccaaca gauggcccau ggcccugcug uacggcauga ucaauaucgc cugcaucaac    1440
agcuucauca ucuacagcca caacgugucc agcaagggcg agaaggugca gagccggaag    1500
aaauucaugc ggaaccugua caugagccug accuccagcu ucaugagaaa gagacuggaa    1560
gcccccaccc ugaagagaua ccugcgggac aacaucacca acauccugcc caacgaagug    1620
ccaggaacaa gcgacgacag cacccgaggaa cccgugauga agaagaggac cuacugcacc    1680 uacugucca gcaagaucag aagaaaaggcc aacgccagcu gcaagaaaug caaaaaagug     1740
aucugccggg agcacaacau cgacaugugc cagagcuguu ucuagc                  1786
```

<210> SEQ ID NO 18
<211> LENGTH: 1786
<212> TYPE: RNA
<213> ORGANISM: Trichoplusia ni

<400> SEQUENCE: 18

```
augggcucua gccuggacga cgagcacauc cugagcgccc ugcugcagag cgacgacgaa     60 cugguggcg aggacagcga cagcgagauc agcgaccacg uguccgagga cgacgugcag       120
uccgacaccg aggaagccuu caucgacgag gugcacgaag ugcagccuac cagcagcggc     180
uccgagaucc uggacgagca gaacgugauc gagcagccug gcagcucccu ggccagcaac    240
agaauccuga cccugcccca gagaaccauc agaggcaaga acaagcacug cugguccacc     300
uccaagagca ccaggcggag cagaguguccc gcccugaaca ucgugcggag ccagaggggc    360
cccaccagaa ugugcagaaa causcuacgac ccccugcugu gcuucaagcu guucuucacc    420
gacgagauca ucagcgagcu ggugaagugg accaacgccg agaucagccu gaagaggcgg     480
gagagcauga ccggcgccac cuucagagac accaacgagg acgagaucua cgccuucuuc    540
ggcauccugg ugaugaccgc cgugagaaag gacaaccaca ugagcaccga cgaccuguuc    600
gacagauccc ugagcauggu guacguguccc gugaugagca gagacagauu cgacuuccug    660
aucagaugcc ugagaauggda cgacaagagc aucagaccca cccugcggga gaacgacgug     720 uucaccccg ugcggaagcu guggaccug uucauccacc agugcaucca gaacuacacc       780
ccuggcgccc accugaccau cgaugagcag cugcuggggcu ucagaggcag augccccuuc    840
agaauguaca uccccaacaa gcccagcaag uacggcauca agauccugau gaugugcgac    900
agcggcacca aguacaugau caacggcaug cccuaccugg gcagaggcac ccagacaaac    960
ggcgugcccc ugggcgagua cuacgugaaa gaacugagca agccugugca uggcagcugc    1020
```

-continued

```
aggaacauca ccugcgacaa cugguucacc agcauccccc uggccaagaa ccugcugcag    1080
gaacccuaca agcugaccau cgugggcacc gugcggagca acaagcggga gaucccagag    1140
gugcugaaga acagcagauc cagaccugug ggaacaagca uguucugcuu cgacggcccc    1200
cugacccugg uguccuacaa gcccaagccc gccaagaugg uguaccugcu guccagcugc    1260
gacgaggacg ccagcaucaa cgagagcacc ggcaagcccc agauggugau guacuacaac    1320
cagaccaagg gcggcgugga cacccuggac cagaugugca gcgugaugac cugcagcaga    1380
aagaccaaca gauggcccau ggcccugcug uacggcauga ucaauaucgc cugcaucaac    1440
agcuucauca ucuacagcca caacgugucc agcaagggcg agaaggugca gagccggaag    1500
aaauucaugc ggaaccugua caugagccug accuccagcu ucaugagaaa gagacuggaa    1560
gcccccaccc ugaagagaua ccugcgggac aacaucacca acauccugcc caacgaagug    1620
ccaggaacaa gcgacgacag caccgaggaa cccgugauga agaagaggac cuacugcacc    1680
uacuguccca gcaagaucag aagaaaggcc aacgccagcu gcaagaaaug caaaaaagug    1740
aucugccggg agcacaacau cgacaugugc cagagcuguu ucuagc                  1786
```

MUTATED PIGGYBAC® TRANSPOSASE

This application is a National Stage application under 35 U.S.C. § 371 of International Patent Application No. PCT/US2019/065129, having an international filing date of Dec. 9, 2019, which claims the benefit of U.S. Provisional Patent Application No. 62/777,325, filed Dec. 10, 2018 and U.S. Provisional Patent Application No. 62/925,516, filed Oct. 24, 2019.

FIELD OF DISCLOSURE

The present invention relates to PIGGYBAC® transposases engineered to increase stability in a cell and use of the engineered PIGGYBAC® transposases for stably transfecting cells, cell line development, genome modification, and improving titer of recombinant proteins, among other uses.

SEQUENCE LISTING

This application contains, as a separate part of the disclosure, a sequence list in computer-readable form (Filename: A-2320-WO-PCT_Sequence.txt, created Nov. 5, 2019, which is 64 KB in size), and which is incorporated by reference in its entirety.

BACKGROUND

Due to their broad applications, biologics are used worldwide in a variety of applications, such as therapeutics and diagnostics. Currently, about 51% of approved biologics are produced using mammalian cells, with the Chinese hamster ovary (CHO) cells being the predominate cellular factory (Zhou and Kantardjeff, Mammalian cell cultures for biologics manufacturing, Springer, Heidelberg, New York, 2014. As a result, the biopharmaceutical industry is undergoing a rapid paradigm shift. Speed-to-market and cost-efficiency are now more important than ever before. High R&D costs and long development lead times for biopharmaceutical drugs have made it imperative to eliminate delays and inefficiencies in drug development and more importantly, manufacturing. At the same time, product pipelines are increasing in complexity and diversity, biopharmaceutical companies now require infrastructures that can accommodate multiple modalities with varying demands, ranging from personalized therapies derived from donor cells to production of biologic drugs in quantities ranging from grams to hundreds of kilograms per year.

As such, there is a need to increase recombinant protein production from host cells and improve long term stability of expression. One way to achieve this objective is to improve the titers of proteins expressed by cell expression systems. The invention described herein provides mutations that contribute to increased stability of PIGGYBAC® transposase expressed in host cells. It was found that PIGGY-BAC® transposases encoded by nucleic acid sequences engineered with such mutations lead to improved titer of the recombinant proteins expressed in cells comprising the engineered PIGGYBAC® transposase compared to the titer of the recombinant proteins expressed in cells comprising wild type PIGGYBAC® transposase or no PIGGYBAC® transposase.

BRIEF SUMMARY OF THE INVENTION

In one aspect the invention provides a PIGGYBAC® transposase comprising an amino acid substitution at one or more of the positions 147, 176, 221, 247, 429, 533, and 573 of SEQ ID NO: 2. In one embodiment the PIGGYBAC® transposase comprises an amino acid substitution of leucine for the isoleucine at one or more of the positions 147, 176, 221, and 247 of SEQ ID NO:2. In one embodiment the PIGGYBAC® transposase comprises an amino acid substitution of threonine for serine at one or more of the positions 429, 533, and 573 of SEQ ID NO: 2. In one embodiment the PIGGYBAC® transposase comprises an amino acid substitution of leucine for the isoleucine at one or more of the positions 147, 176, 221, and 247 and/or an amino acid substitution of threonine for serine at one or more of the positions 429, 533, and 573 of SEQ ID NO:2. In a related embodiment the PIGGYBAC® transposase comprises at least one of the following amino acid substitutions, a leucine for the isoleucine at position 147 of SEQ ID NO:2, a leucine for the isoleucine at position 247 of SEQ ID NO:2, and a threonine for the serine at position 533 of SEQ ID NO:2. In a related embodiment the PIGGYBAC® transposase comprises at least two of the following amino acid substitutions, a leucine for the isoleucine at position 147 of SEQ ID NO:2, a leucine for the isoleucine at position 247 of SEQ ID NO:2, and a threonine for the serine at position 533 of SEQ ID NO:2. In another related embodiment the PIGGYBAC® transposase comprises a leucine for isoleucine substitution at position 147 of SEQ ID NO:2, a leucine for isoleucine substitution at position 247 of SEQ ID NO:2, and a threonine for serine substitution at position 533 of SEQ ID NO: 2. In one embodiment the PIGGYBAC® transposase comprises the titer of a recombinant protein of interest expressed by a cell transfected with the engineered PIGGYBAC® transposase as described herein is improved compared to the titer of the same protein of interest expressed by a cell transfected with a wild type PIGGYBAC® transposase or no PIGGYBAC® transposase. In one embodiment, the recombinant protein of interest is an antigen binding protein.

In one aspect the invention provides a PIGGYBAC® transposase engineered to increase stability in a host cell, wherein the PIGGYBAC® transposase comprises an amino acid substitution at one or more of the positions 147, 176, 221, 247, 429, 533, and 573 of SEQ ID NO: 2.

In another aspect the invention provides a PIGGYBAC® transposase having the amino acid sequence of SEQ ID NO: 4, SEQ ID NO: 6, SEQ ID NO: 8, SEQ ID NO: 10, SEQ ID NO: 12, SEQ ID NO: 14, or SEQ ID NO: 16. In another aspect the invention provides a PIGGYBAC® transposase having the amino acid sequence of SEQ ID NO: 4, SEQ ID NO: 6, or SEQ ID NO: 8. In another aspect the invention provides a PIGGYBAC® transposase having the amino acid sequence of SEQ ID NO: 12, SEQ ID NO: 14, or SEQ ID NO: 16. In another aspect the invention provides a PIGGY-BAC® transposase having the amino acid sequence of SEQ ID NO: 10 or 12. In another aspect the invention provides a PIGGYBAC® transposase having the amino acid sequence of SEQ ID NO:4. In another aspect the invention provides a PIGGYBAC® transposase having the amino acid sequence of SEQ ID NO:6. In another aspect the invention provides a PIGGYBAC® transposase having the amino acid sequence of SEQ ID NO: 8. In another aspect the invention provides a PIGGYBAC® transposase having the amino acid sequence of SEQ ID NO:10. In another aspect the invention provides a PIGGYBAC® transposase having the amino acid sequence of SEQ ID NO: 12. In another aspect the invention provides a PIGGYBAC® transposase having the amino acid sequence of SEQ ID NO: 14. In another aspect the invention provides a PIGGYBAC® transposase having the amino acid sequence of SEQ ID NO: 16.

In another aspect the invention provides an engineered nucleic acid molecule encoding a PIGGYBAC® transposase as described herein. In another aspect the invention provides a PIGGYBAC® transposase encoded by the nucleic acid sequence of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, or SEQ ID NO: 18. In another aspect the invention provides a PIGGYBAC® transposase encoded by the nucleic acid sequence of SEQ ID NO: 3, SEQ ID NO: 5, or SEQ ID NO: 7. In another aspect the invention provides a PIGGYBAC® transposase encoded by the nucleic acid sequence of SEQ ID NO: 11, SEQ ID NO: 13, or SEQ ID NO: 15. In another aspect the invention provides a PIGGYBAC® transposase encoded by the nucleic acid sequence of SEQ ID NO: 9, or SEQ ID NO: 11. In another aspect the invention provides a PIGGYBAC® transposase encoded by the nucleic acid sequence of SEQ ID NO: 17, or SEQ ID NO: 18. In another aspect the invention provides a PIGGYBAC® transposase encoded by the nucleic acid sequence of SEQ ID NO: 3. In another aspect the invention provides a PIGGYBAC® transposase encoded by the nucleic acid sequence of SEQ ID NO: 5. In another aspect the invention provides a PIGGYBAC® transposase encoded by the nucleic acid sequence of SEQ ID NO: 7. In another aspect the invention provides a PIGGYBAC® transposase encoded by the nucleic acid sequence of SEQ ID NO: 9. In another aspect the invention provides a PIGGYBAC® transposase encoded by the nucleic acid sequence of SEQ ID NO: 11. In another aspect the invention provides a PIGGYBAC® transposase encoded by the nucleic acid sequence of SEQ ID NO: 13. In another aspect the invention provides a PIGGYBAC® transposase encoded by the nucleic acid sequence of SEQ ID NO: 15. In another aspect the invention provides a PIGGYBAC® transposase encoded by the nucleic acid sequence of SEQ ID NO: 17. In another aspect the invention provides a PIGGYBAC® transposase encoded by the nucleic acid sequence of SEQ ID NO: 18.

In another aspect the invention provides a vector comprising the nucleic acid molecule encoding a PIGGYBAC® transposase as described herein. In one embodiment the vector comprises the nucleic acid molecule encoding a PIGGYBAC® transposase as described herein, further comprising at least one nucleic acid sequence encoding at least one protein of interest flanked by at least the 5' and 3' inverted repeat elements of a PIGGYBAC® transposon. In one embodiment the vector comprises one or more nucleic acid sequences encoding one or more proteins of interest.

In another aspect the invention provides a cell transfected with a vector as described herein. In one embodiment the cell is transfected with a PIGGYBAC® transposase encoded by the nucleic acid sequence of SEQ ID NO: 17 or 18. In one embodiment the cell is a host cell. In one embodiment the cell is a CHO cell. In one embodiment the cell is an immune cell.

In another aspect the invention provides a cell co-transfected with an engineered nucleic acid molecule encoding a PIGGYBAC® transposase as described herein, and a vector comprising at least one nucleic acid molecule encoding at least one protein of interest flanked by at least the 5' and 3' inverted repeat elements of a PIGGYBAC® transposon. In another embodiment the invention provides a cell co-transfected with a vector comprising an engineered nucleic acid molecule encoding a PIGGYBAC® transposase as described herein, and a vector comprising at least one nucleic acid molecule encoding at least one protein of interest flanked by at least the 5' and 3' inverted repeat elements of a PIGGYBAC® transposon. In another embodiment the invention provides a cell co-transfected with a vector comprising an engineered nucleic acid molecule encoding a PIGGYBAC® transposase as described herein, and also comprising at least one nucleic acid molecule encoding at least one protein of interest flanked by at least the 5' and 3' inverted repeat elements of a PIGGYBAC® transposon.

In another aspect the invention provides a cell as described herein, wherein the titer of a protein of interest expressed by the cell transfected with the engineered PIG-GYBAC® transposase is improved compared to the titer of the same protein of interest expressed by a cell transfected with a wild type PIGGYBAC® transposase or no PIGGY-BAC® transposase. In one embodiment is provided a recombinant protein of interest expressed by the cell. In a related embodiment is a pharmaceutical composition comprising the recombinant protein of interest.

In another aspect the invention provides a method for improving the titer of a recombinant protein of interest expressed by a host cell comprising engineering a nucleic acid molecule encoding a PIGGYBAC® transposase to increase stability in the host cell: co-transfecting the host cell the engineered nucleic acid molecule encoding the PIGGYBAC® transposase and with a vector comprising the nucleic acid sequence encoding the protein of interest flanked by at least the 5' and 3' inverted repeat elements of a PIGGYBAC® transposon; and culturing the cells to express the recombinant protein of interest, wherein the titer of the recombinant protein of interest expressed by the host cell transfected with the engineered PIGGYBAC® transposase is improved compared to the titer of the recombinant protein of interest expressed by a host cell transfected with a wild type PIGGYBAC® transposase or no PIGGYBAC® transposase. In one embodiment the host cell is transfected with a first vector comprising the engineered nucleic acid molecule encoding the PIGGYBAC® transposase and with a second vector comprising the nucleic acid sequence encoding the protein of interest flanked by at least the 5' and 3' inverted repeat elements of a PIGGYBAC® transposon. In one embodiment the host cell is transfected with a single vector comprising the engineered nucleic acid molecule encoding the PIGGYBAC® transposase and a nucleic acid sequence encoding the protein of interest flanked by at least the 5' and 3' inverted repeat elements of a PIGGYBAC® transposon.

In another aspect the invention provides a method for increasing recombinant protein production in a mammalian cell culture expressing a recombinant protein comprising establishing a cell culture in a bioreactor using a host cell that has been co-transfected with a nucleic acid molecule encoding a PIGGYBAC® transposase engineered to increase stability in the host cell, and a vector comprising the nucleic acid molecule encoding the protein of interest flanked by at least the inverted repeat elements of a PIG-GYBAC® transposon; and expressing the recombinant protein of interest: wherein the titer of the recombinant protein of interest expressed by the host cell transfected with the engineered PIGGYBAC® transposase is improved compared to the titer of the recombinant protein of interest expressed by the host cell transfected with a wild type PIGGYBAC® transposase or no PIGGYBAC® transposase. In one embodiment the host cell has been co-transfected with a vector comprising a nucleic acid molecule encoding a PIGGYBAC® transposase engineered to increase stability in the host cell, and a vector comprising the nucleic acid molecule encoding the protein of interest flanked by at least the inverted repeat elements of a PIGGYBAC® transposon. In one embodiment the host cell is transfected with a single vector comprising the engineered nucleic acid molecule encoding the PIGGYBAC® transposase and a nucleic acid sequence encoding the protein of interest flanked by at least the 5' and 3' inverted repeat elements of a PIGGYBAC® transposon.

In another aspect the invention provides a method for producing an isolated, purified, recombinant protein of interest comprising establishing a cell culture in a bioreactor with a host cell expressing a recombinant protein of interest, wherein the cell line has been co-transfected with a nucleic acid sequence encoding a PIGGYBAC® transposase engineered to increase stability in the host cell, and a vector comprising the nucleic acid sequence encoding the protein of interest flanked by at least the 5' and 3' inverted repeat elements of a PIGGYBAC® transposon: culturing the cells to express the recombinant protein of interest: harvesting the recombinant protein of interest, processing the recombinant protein of interest through one or more unit operations, and obtaining an isolated, purified, recombinant protein of interest. In one embodiment the cell line has been co-transfected with a vector comprising a nucleic acid sequence encoding a PIGGYBAC® transposase engineered to increase stability in the host cell, and a vector comprising the nucleic acid sequence encoding the protein of interest flanked by at least the 5' and 3' inverted repeat elements of a PIGGYBAC® transposon. In one embodiment the host cell is transfected with a single vector comprising the engineered nucleic acid molecule encoding the PIGGYBAC® transposase and a nucleic acid sequence encoding the protein of interest flanked by at least the 5' and 3' inverted repeat elements of a PIGGYBAC® transposon. In one embodiment at least one unit operation is a capture chromatography step selected from affinity chromatography, ion exchange chromatography, anion exchange chromatography, cation exchange chromatography, multi-modal chromatography, hydrophobic interaction chromatography, and hydroxyapatite chromatography. In a related at least one unit operation is a polish chromatography step selected from ion exchange chromatography, anion exchange chromatography, cation exchange chromatography, multi-modal chromatography, hydrophobic interaction chromatography, and hydroxyapatite chromatography. In one embodiment at least one unit operation is selected from virus inactivation, virus filtration, depth filtration, and UF/DF. In one embodiment the titer of the recombinant protein of interest expressed by the host cell transfected with the engineered PIGGYBAC® transposase is improved compared to the titer of the recombinant protein of interest expressed by the host cell transfected with a wild type PIGGYBAC® transposase or no PIGGYBAC® transposase. In one embodiment is the isolated, purified, recombinant protein of. In a related embodiment is a pharmaceutical composition comprising the isolated protein of interest.

In one aspect the invention provides a kit for transfecting a cell comprising a vector comprising a nucleic acid sequence encoding a PIGGYBAC® transposase engineered to increase stability in the host cell; and a vector comprising at least the 5' and 3' inverted repeat elements of a PIGGYBAC® transposon into which at least one nucleic acid sequence encoding at least one protein of interest is inserted.

In one aspect the invention provides a method of generating non-viral genetically modified cells, comprising: (a) establishing a vector comprising a nucleic acid sequence encoding a PIGGYBAC® transposase engineered to increase stability in a cell and at least one nucleic acid sequence encoding at least one protein of interest flanked by at least the 5' and 3' inverted repeat elements of a PIGGYBAC® transposon: (b) isolating native immune cells from a donor or subject: (b) transfecting the cells with the vector and a nucleic acid sequence encoding a PIGGYBAC® transposase engineered to increase stability in a cell; and (c) expanding the cells by cell culture into a larger population of non-viral, genetically modified cells. In one embodiment the cells are transfected with the vector comprising at least one nucleic acid sequence encoding at least one protein of interest flanked by at least the 5' and 3' inverted repeat elements of a PIGGYBAC® transposon, and a vector comprising a nucleic acid sequence encoding a PIGGYBAC® transposase engineered to increase stability in a cell. In one embodiment the cells are transfected with a vector comprising at least one nucleic acid sequence encoding at least one protein of interest flanked by at least the 5' and 3' inverted repeat elements of a PIGGYBAC® transposon, and a nucleic acid sequence encoding a PIGGYBAC® transposase engineered to increase stability in a cell.

In one aspect the invention provides a method of treating a subject with a non-viral genetically modified cell, comprising: (a) establishing a vector comprising a least one nucleic acid sequence encoding at least one protein of interest flanked by at least the 5' and 3' inverted repeat elements of a PIGGYBAC® transposon: (b) isolating native immune cells from a subject or donor: (c) transfecting the cells with the vector and a nucleic acid sequence encoding a PIGGYBAC® transposase engineered to increase stability in a cell: (d) expanding the cells by cell culture into a larger population of genetically modified cells: (e) isolating the transformed cells from the cell culture to obtain a cell population comprising the genetically modified cells; and (f) reintroducing the non-viral, genetically modified cells into the subject. In one embodiment the cells are transfected with the vector comprising at least one nucleic acid sequence encoding at least one protein of interest flanked by at least the 5' and 3' inverted repeat elements of a PIGGYBAC® transposon, and a vector comprising a nucleic acid sequence encoding a PIGGYBAC® transposase engineered to increase stability in a cell. In one embodiment the cells are transfected with a vector comprising at least one nucleic acid sequence encoding at least one protein of interest flanked by at least the 5' and 3' inverted repeat elements of a PIGGYBAC® transposon, and a nucleic acid sequence encoding a PIGGYBAC® transposase engineered to increase stability in a cell. In one embodiment the native immune cell is a mononuclear cell. In one embodiment the native immune cell is a T cell. In one embodiment at least one protein of interest is an antigen receptor, a T cell receptor, or a chimeric antigen receptor. In one embodiment the cell is also transfected with a nucleic acid molecule encoding a suicide gene, an inducible on or accelerator switch, or both. In one embodiment are non-viral genetically modified cells, cell populations, or cell cultures. In one embodiment is a formulation comprising the genetically modified cells or cell populations. In another embodiment is a method of treating or preventing a disease or disorder in a donor or subject in need thereof comprising administering to the donor or subject an effective amount of the genetically modified cells or cell populations.

BRIEF DESCRIPTION OF THE DRAWINGS

FIG. 1: Predicted secondary structure. Bars indicate predicted alpha-helical regions, arrows indicate predicted beta sheet regions. The mPBase sequence is SEQ ID NO: 2.

6A): Electroporation-based transfection method comparing DNA transposase to mRNA transposase. Increasing the mRNA transposase improved expression. 1) 0 μg transposase, 20 μg mAb DNA; 2) Double mutant "ILT" DNA; 20 μg mAb DNA, 5 μg transposase, ratio 4:1; 3) Double mutant "ILT" mRNA 20 μg mAb DNA, 5 μg transposase, ratio 4:1; 4) Double mutant "ILT" mRNA 20 μg mAb DNA, 10 μg transposase, ratio 2:1; 5) Double mutant "ILT" mRNA 20 μg mAb DNA, 20 μg transposase, ratio 1:1; 11) Double mutant "ILT" mRNA 14 μg mAb DNA, 100 μg transposase, ratio 7:1; 12) Double mutant "ILT" mRNA 28 μg mAb DNA, 200 μg transposase, ratio 7:1.

6B): The lipid-based transfection method comparing DNA transposase to mRNA transposase. Increasing the mRNA transposase improved expression. PIGGY-BAC® transposase double mutant "ILT" DNA 2 μg mAb DNA, 0.5 μg transposase, ratio 4:1; 2 μg mAb DNA, 2 μg transposase, ratio 1:1; 4 μg mAb DNA, 4 μg transposase, ratio 1:1; PIGGYBAC® transposase double mutant "ILT" mRNA 2 μg mAb DNA, 0.5 μg transposase, ratio 4:1; 2 μg mAb DNA, 2 μg transposase, ratio 1:1; 4 μg mAb DNA, 4 μg transposase, ratio 1:1.

Figure 7:
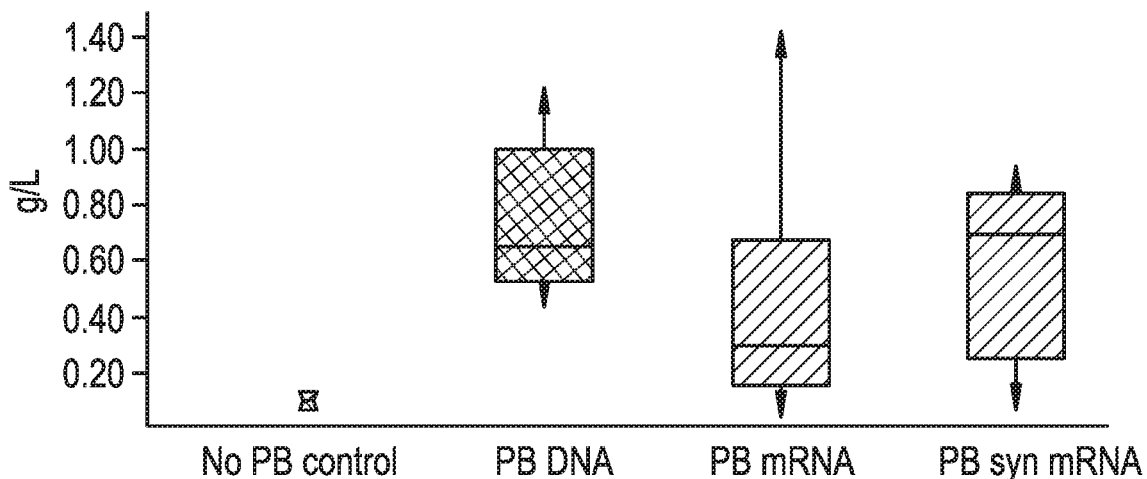

FIG. 7 Expression levels in transfected pools from electroporation. Transfection of the double mutant transposase "ILT" DNA and both mRNAs. Synthetic mRNA (PB syn mRNA) and mRNA (PB mRNA) transfected pools had similar titers to the DNA (PB DNA) transposase pools and higher titers than no transposase control pools. Down arrow is Min. Up arrow is Max. White Bar is median.

Figure 8A:
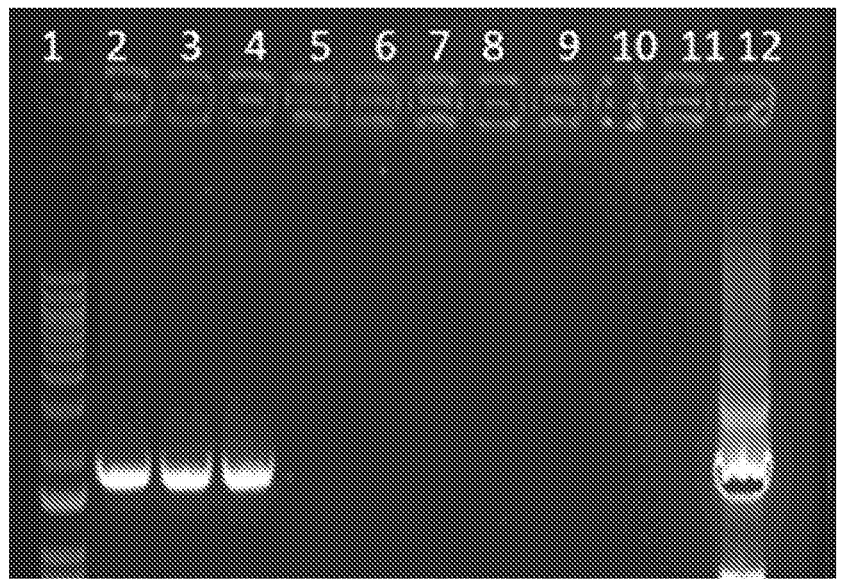

FIGS. 8A and B: Integration at the genomic and transcript level of DNA and mRNA in transfected cell line pools.

8A) All pool cell lines transfected with double mutant, "ILT", DNA transposase had integration at the genomic level, whereas those transfected with mRNA did not have integration at the genomic level. An ~1.7 kb band indicates the presence of the transposase in the genome of the cell line. Lane 1 Ladder. Lanes 2-4 PIGGY-BAC® transposase double mutant "ILT" DNA. Lane 5 No transfection. Lanes 6-11 PIGGYBAC® transposase double mutant "ILT" mRNA. Lane 12 plasmid DNA control.

8B) Gel image of an RT PCR assay to check for transcription at the RNA level. All pool cell lines transfected with double mutant, "ILT", DNA transposase had transcription at the RNA level, whereas those transfected with mRNA did not have transcription at the RNA level. An ~1.7 kb band indicates the presence of the transposase transcript. Lane 1 Ladder. Lanes 2-3 PIGGYBAC® transposase double mutant "ILT" mRNA. Lane 4 PIGGYBAC® transposase double mutant "ILT" DNA. Lane 5 plasmid DNA control.

Figure 9:
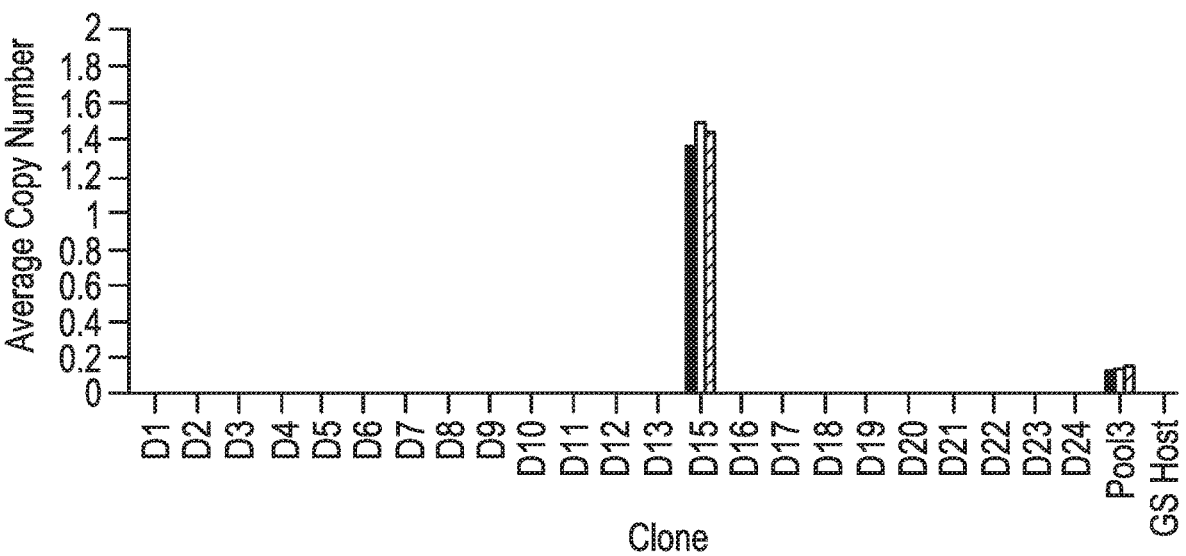

FIG. 9 The pool had low copy number and contained clones that did not have integration of the transposase.

FIG. 10 TCR-T cells generated using non-viral gene delivery and PIGGYBAC® transposase exhibit robust function in vitro. (A) T cells are successfully engineered to express TCRs using the double mutant, ILT. (B) Target-cell lysis and (C) proliferation of PIGGYBAC®-engineered TCR-T cells following 5-day co-incubation with antigen-presenting cells.

DETAILED DESCRIPTION OF THE INVENTION

DNA transposons, or transposable elements, are genetic elements that can mobilize from one location to another in the host genome. Transposable elements are typically divided into two classes, Class 1 is represented by the retrotransposons, and Class 2 includes the "cut-and-paste" DNA transposons.

Class 2 DNA transposons are characterized by two components, the transposon comprising a DNA segment flanked by two terminal inverted repeats, and a transposase that catalyzes the transposon's mobilization. The transposase acts by binding the inverted repeats, excising the DNA segment (the cut) flanked by the terminal inverted repeats and reintegrating the segment into a new location (the paste).

The PIGGYBAC® transposon is a Class 2 transposon and although originally isolated from *Trichoplusia ni* (cabbage looper moth), it has been shown to actively transpose in mammalian cells, with a preference for accessible chromatin structures (Li et al., Molecular and Cellular Biology 33(7): 1317-1330, 2013: Yoshida et al., Scientific Reports Article number 43613(2017)). Due to its ability to introduce exogeneous DNA into a genome and promote stable transgene expression, the PIGGYBAC® transposon system is a useful tool for genetic manipulation in mammalian cells and has been used to facilitate the stable transfection of mammalian cells, to generate stable and high producing polyclonal cultures of mammalian cells, rapid production of recombinant protein from heterogeneous populations of transfected cells and developing clones for cell line development, due to it's recognition motif that is commonly associated with regions of open chromatin and actively transcribed regions (Published US Patent Application No: US 2010/0311116; Ding et al., Cell 122(3):473-483, 2005: Wu et al., Proc. Natl. Acad. Sci. USA 103(4) 15008-13, 2006, Matasci et al., Biotechnology & Bioengineering 108(9): 2141-50, 2011: Matasci et al., BMC Proceedings 5(SUPPL.8) p. 34, 2011: Balasubramanian et al., J. Biotechnology 200:61-9, 2015: Balasubramanian et al., Biotechnology Progress 32(5):1308-1317, 2016; Balasubramanian et al., Biotechnology & Bioengineering 113(6):1234-43, 2016; Ahmadi et al., PLOS ONE 12(6):e0179902, 2017: Rajendra et al., Biotechnology Progress 33(2):534-540, 2017; and Rajendra et al., Biotechnology Progress 33(6): 1436-1448, 2017.

Efforts have been made to improve PIGGYBAC® efficiency on a molar basis through modifications to the transposase to increase excision frequency using a display library approach and/or performing sequence comparisons with homologs from other species and generating hyperactive transposases (see for example U.S. Pat. Nos. 8,399,643; 9,670,503; 9,783,790; 9,546,382; and Yusa et al. Proc. Natl. Acad. Sci. USA 108(4): 1531-36, 2011).

Not much is known about the structure of PIGGYBAC® transposase. Analysis of the PIGGYBAC® transposase amino acid sequence showed that it is a mostly alpha helical protein. In an attempt to improve stability of PIGGYBAC® transposase introduced into a cell, mutations were made within the alpha helices and putative N-linked glycosylation sites (i.e. NXS/t motif) and were found to increase titer as described herein. Engineered versions of PIGGYBAC® transposases, including single mutations or combinations of mutations, were transfected into cells along with a Protein of interest flanked by at least the 5' and 3' inverted repeat elements of a PIGGYBAC® transposon and were evaluated for expression of the protein of interest in comparison with similar cells transfected with a wild type, unmutated, PIG-GYBAC® transposase from *Trichoplusia ni* (SEQ ID NO: 2) and cells containing no PIGGYBAC® transposase. The PIGGYBAC® transposases encoded by nucleic acid sequences engineered to increase stability were found to improve titer of recombinant proteins expressed in cells comprising an engineered PIGGYBAC® transposase compared to the titer of the recombinant proteins expressed in cells comprising wild type PIGGYBAC® transposase or no PIGGYBAC® transposase.

As used herein, the term "PIGGYBAC® transposon" or "PIGGYBAC® transposable element" refers to a polynucleotide sequence that can be excised from a donor polynucleotide (e.g., a vector) and integrated into a target site, for instance, the genomic or extrachromosomal DNA of a cell. For example, the PIGGYBAC® transposable element from *Trichoplusia ni* is 2472 bp in length with short inverted repeats including an asymmetric terminal repeat structure with a 3-bp spacer between the 5' 13-bp terminal repeat and 5' 19-bp internal repeat and a 31-bp spacer between the 3' 13-bp terminal repeat and 3' 19-bp internal repeat, and a single 2.1-kp open reading frame encoding a functional transposase. (Li et al., Mol. Genet. Genomics (2001) 266: 190-198: Cary et al., Virology (1989) 172:156-169).

As used herein, the 5' and 3' inverted repeat elements of a PIGGYBAC® transposon refer to the 5' and 3' segments including the target TTAA site, terminal repeats spacers, and internal repeats of a PIGGYBAC® transposon, in the case to *T. ni*, these include the target TTAA sites, 5' 13-bp terminal repeat and 5' 19-bp internal repeat with a 3-bp spacer between and the 3' 13-bp terminal repeat and 3' 19-bp internal repeat a 31-bp spacer between.

As used herein, the term "PIGGYBAC® transposase" refers to a polypeptide that catalyzes the excision of a PIGGYBAC® transposon from a donor polynucleotide (e.g., a vector) and the subsequent integration of the PIG-GYBAC® transposon into the genomic or extrachromosomal DNA of a target cell. The PIGGYBAC® transposase makes use of a cut and paste mechanism, inserting at a TTAA target site that is duplicated upon insertion and excised precisely after insertion, restoring the donor site to its pretransposon state. (Elick et al., Genetica 98:33-41, 1996. Fraser et al., Insect Mol. Biol. 5:141-151, 1996. Wang and Fraser, Insect Mol. Biol. 1:109-116, 1993). The PIG-GYBAC® transposase may be present as a polypeptide. Alternatively, the PIGGYBAC® transposase may present a nucleic acid molecule that includes a coding sequence encoding a PIGGYBAC® transposase. In some embodiments of the invention, when the PIGGYBAC® transposase is present as an engineered nucleic acid molecule encoding the engineered PIGGYBAC® transposase, the engineered nucleic acid molecule may be present on the same vector that includes the PIGGYBAC® transposon, i.e., in cis. In other embodiments of the invention, the engineered nucleic acid molecule may be present on a second vector separate from the transposon, i.e., in trans. The engineered PIGGY-BAC® transposases described herein are unique in that the titer of a recombinant protein of interest expressed by a cell comprising an engineered PIGGYBAC® transposase is improved compared to the titer of the recombinant protein of interest expressed by a cell comprising a wild type PIGGY-BAC® transposase or no PIGGYBAC® transposase.

The terms "polypeptide" or "protein" are used interchangeably throughout and refer to a molecule comprising two or more amino acid residues joined to each other by peptide bonds. Polypeptides and proteins also include macromolecules having one or more deletions from, insertions to, and/or substitutions of the amino acid residues of the native sequence, that is, a polypeptide or protein produced by a naturally-occurring and non-recombinant cell: or is produced by a genetically-engineered or recombinant cell, and comprise molecules having one or more deletions from, insertions to, and/or substitutions of the amino acid residues of the amino acid sequence of the native protein. Polypeptides and proteins also include amino acid polymers in which one or more amino acids are chemical analogs of a corresponding naturally-occurring amino acid and polymers. Polypeptides and proteins are also inclusive of modifications including, but not limited to, glycosylation, lipid attachment, sulfation, gamma-carboxylation of glutamic acid residues, hydroxylation and ADP-ribosylation.

The PIGGYBAC® transposases described herein are intended to include polypeptides bearing one or more insertions, deletions, or substitutions, or any combination thereof, of amino acid residues as well as modifications other than insertions, deletions, or substitutions of amino acid residues as compared to the wild type *Trichoplusia ni* (Cabbage looper moth) PIGGYBAC® transposase (SEQ ID NO:2). As used herein, "amino acid substitution at one or more of positions" means substitutions at 1, 2, 3, 4, 5, 6, or 7 of the recited positions. In some embodiments, "amino acid substitution at one or more of positions" means substitutions at 1, 2, 3, 4, 5 or 6 of the recited positions. In some embodiments, "amino acid substitution at one or more of positions" means substitutions at 1, 2, 3, 4, or 5 of the recited positions. In some embodiments, "amino acid substitution at one or more of positions" means substitutions at 1, 2, 3, or 4, of the recited positions. In some embodiments, "amino acid substitution at one or more of positions" means substitutions at 1, 2, or 3 of the recited positions. In some embodiments, "amino acid substitution at one or more of positions" means substitutions at 1 or 2 of the recited positions.

The invention provides a PIGGYBAC® transposase comprising an amino acid substitution at one or more of the positions 147, 176, 221, 247, 429, 533, and 573 of SEQ ID NO: 2. In one embodiment the transposase comprises an amino acid substitution of leucine for the isoleucine at one or more of the positions 147, 176, 221, and 247 of SEQ ID NO:2. In one embodiment the transposase comprises an amino acid substitution of threonine for serine at one or more of the positions 429, 533, and 573 of SEQ ID NO:2. In one embodiment the transposase comprises an amino acid substitution of leucine for the isoleucine at one or more of the positions 147, 176, 221, and 247 and/or an amino acid substitution of threonine for serine at one or more of the positions 429, 533, and 573 of SEQ ID NO:2. In a related embodiment the transposase comprises at least one of the following amino acid substitutions, a leucine for the isoleucine at position 147 of SEQ ID NO:2, a leucine for the isoleucine at position 247 of SEQ ID NO:2, and a threonine for the serine at position 533 of SEQ ID NO:2. In a related embodiment the transposase comprises at least two of the following amino acid substitutions, a leucine for the isoleucine at position 147 of SEQ ID NO:2, a leucine for the isoleucine at position 247 of SEQ ID NO:2, and a threonine for the serine at position 533 of SEQ ID NO:2. In another related embodiment the transposase comprises a leucine for isoleucine substitution at position 147 of SEQ ID NO:2, a leucine for isoleucine substitution at position 247 of SEQ ID NO: 2, and a threonine for serine substitution at position 533 of SEQ ID NO:2. In one embodiment the titer of a recombinant protein of interest expressed by a cell transfected with the engineered PIGGYBAC® transposase is improved compared to the titer of the same protein of interest expressed by a cell transfected with a wild type PIGGYBAC® transposase or no PIGGYBAC® transposase.

The invention also provides a PIGGYBAC® transposase engineered to increase stability in a host cell, wherein the PIGGYBAC® transposase comprises an amino acid substitution at one or more of the positions 147, 176, 221, 247, 429, 533, and 573 of SEQ ID NO: 2. In another aspect the invention provides a PIGGYBAC® transposase having the amino acid sequence of SEQ ID NO: 4, SEQ ID NO: 6, SEQ ID NO: 8, SEQ ID NO: 10, SEQ ID NO: 12, SEQ ID NO: 14, or SEQ ID NO: 16. In another aspect the invention provides a PIGGYBAC® transposase having the amino acid sequence of SEQ ID NO: 4, SEQ ID NO: 6, or SEQ ID NO: 8. In another aspect the invention provides a PIGGYBAC® transposase having the amino acid sequence of SEQ ID NO: 12, SEQ ID NO: 14, or SEQ ID NO: 16. In another aspect the invention provides a PIGGYBAC® transposase having the amino acid sequence of SEQ ID NO: 10 or 12. In another aspect the invention provides a PIGGYBAC® transposase having the amino acid sequence of SEQ ID NO:4. In another aspect the invention provides a PIGGYBAC® transposase having the amino acid sequence of SEQ ID NO:6. In another aspect the invention provides a PIGGYBAC® transposase having the amino acid sequence of SEQ ID NO: 8. In another aspect the invention provides a PIGGYBAC® transposase having the amino acid sequence of SEQ ID NO:10. In another aspect the invention provides a PIGGYBAC® transposase having the amino acid sequence of SEQ ID NO: 12. In another aspect the invention provides a PIGGYBAC® transposase having the amino acid sequence of SEQ ID NO: 14. In another aspect the invention provides a PIGGYBAC® transposase having the amino acid sequence of SEQ ID NO: 16.

TABLE 1

Amino acid sequences of wild type and mutated PIGGYBAC ® transposases

| SEQ ID NO: | ID | SEQUENCE |
|---|---|---|
| 2 | WT | MGSSLDDEHILSALLQSDDELVGEDSDSEISDHVSEDDVQSDT EEAFIDE VHEVQPTSSGSEILDEQNVIEQPGSSLASNRILTLPQRTIRGKN KHCWST SKSTRRSRVSALNIVRSQRGPTRMCRNIYDPLLCFKLFFTDEII SEIVKW TNAEISLKRRESMTGATFRDTNEDEIYAFFGILVMTAVRKDN HMSTDDLF DRSLSMVYVSVMSRDRFDFLIRCLRMDDKSIRPTLRENDVFT PVRKIWDL FIHQCIQNYTPGAHLTIDEQLLGFRGRCPFRMYIPNKPSKYGIK ILMMCD SGTKYMINGMPYLGRGTQTNGVPLGEYYVKELSKPVHGSCR NITCDNWFT SIPLAKNLLQEPYKLTIVGTVRSNKREIPEVLKNSRSRPVGTS MFCFDGP LTLVSYKPKPAKMVYLLSSCDEDASINESTGKPQMVMYYNQ TKGGVDTLD QMCSVMTCSRKTNRWPMALLYGMINIACINSFIIYSHNVSSK GEKVQSRK KFMRNLYMSLTSSFMRKRLEAPTLKRYLRDNISNILPNEVPG TSDDSTEE PVMKKRTYCTYCPSKIRRKANASCKKCKKVICREHNIDMCQ SCF |
| 4 | I147L | MGSSLDDEHILSALLQSDDELVGEDSDSEISDHVSEDDVQSDT EEAFIDE VHEVQPTSSGSEILDEQNVIEQPGSSLASNRILTLPQRTIRGKN KHCWST SKSTRRSRVSALNIVRSQRGPTRMCRNIYDPLLCFKLFFTDEII SELVKW TNAEISLKRRESMTGATFRDTNEDEIYAFFGILVMTAVRKDN HMSTDDLF DRSLSMVYVSVMSRDRFDFLIRCLRMDDKSIRPTLRENDVFT PVRKIWDL FIHQCIQNYTPGAHLTIDEQLLGFRGRCPFRMYIPNKPSKYGIK ILMMCD SGTKYMINGMPYLGRGTQTNGVPLGEYYVKELSKPVHGSCR NITCDNWFT SIPLAKNLLQEPYKLTIVGTVRSNKREIPEVLKNSRSRPVGTS MFCFDGP LTLVSYKPKPAKMVYLLSSCDEDASINESTGKPQMVMYYNQ TKGGVDTLD |

TABLE 1-continued

Amino acid sequences of wild type and mutated PIGGYBAC ® transposases

| SEQ ID NO: | ID | SEQUENCE |
|---|---|---|
| | | QMCSVMTCSRKTNRWPMALLYGMINIACINSFIIYSHNVSSK<br>GEKVQSRK<br>KFMRNLYMSLTSSFMRKRLEAPTLKRYLRDNISNILPNEVPG<br>TSDDSTEE<br>PVMKKRTYCTYCPSKIRRKANASCKKCKKVICREHNIDMCQ<br>SCF |
| 6 | I247L | MGSSLDDEHILSALLQSDDELVGEDSDSEISDHVSEDDVQSDT<br>EEAFIDE<br>VHEVQPTSSGSEILDEQNVIEQPGSSLASNRILTLPQRTIRGKN<br>KHCWST<br>SKSTRRSRVSALNIVRSQRGPTRMCRNIYDPLLCFKLFFTDEII<br>SEIVKW<br>TNAEISLKRRESMTGATFRDTNEDEIYAFFGILVMTAVRKDN<br>HMSTDDLF<br>DRSLSMVYVSVMSRDRFDFLIRCLRMDDKSIRPTLRENDVFT<br>PVRKLWDL<br>FIHQCIQNYTPGAHLTIDEQLLGFRGRCPFRMYIPNKPSKYGIK<br>ILMMCD<br>SGTKYMINGMPYLGRGTQTNGVPLGEYYVKELSKPVHGSCR<br>NITCDNWFT<br>SIPLAKNLLQEPYKLTIVGTVRSNKREIPEVLKNSRSRPVGTS<br>MFCFDGP<br>LTLVSYKPKPAKMVYLLSSCDEDASINESTGKPQMVMYYNQ<br>TKGGVDTLD<br>QMCSVMTCSRKTNRWPMALLYGMINIACINSFIIYSHNVSSK<br>GEKVQSRK<br>KFMRNLYMSLTSSFMRKRLEAPTLKRYLRDNISNILPNEVPG<br>TSDDSTEE<br>PVMKKRTYCTYCPSKIRRKANASCKKCKKVICREHNIDMCQ<br>SCF |
| 8 | S533T | MGSSLDDEHILSALLQSDDELVGEDSDSEISDHVSEDDVQSDT<br>EEAFIDE<br>VHEVQPTSSGSEILDEQNVIEQPGSSLASNRILTLPQRTIRGKN<br>KHCWST<br>SKSTRRSRVSALNIVRSQRGPTRMCRNIYDPLLCFKLFFTDEII<br>SEIVKW<br>TNAEISLKRRESMTGATFRDTNEDEIYAFFGILVMTAVRKDN<br>HMSTDDLF<br>DRSLSMVYVSVMSRDRFDFLIRCLRMDDKSIRPTLRENDVFT<br>PVRKIWDL<br>FIHQCIQNYTPGAHLTIDEQLLGFRGRCPFRMYIPNKPSKYGIK<br>ILMMCD<br>SGTKYMINGMPYLGRGTQTNGVPLGEYYVKELSKPVHGSCR<br>NITCDNWFT<br>SIPLAKNLLQEPYKLTIVGTVRSNKREIPEVLKNSRSRPVGTS<br>MFCFDGP<br>LTLVSYKPKPAKMVYLLSSCDEDASINESTGKPQMVMYYNQ<br>TKGGVDTLD<br>QMCSVMTCSRKTNRWPMALLYGMINIACINSFIIYSHNVSSK<br>GEKVQSRK<br>KFMRNLYMSLTSSFMRKRLEAPTLKRYLRDNITNILPNEVPG<br>TSDDSTEE<br>PVMKKRTYCTYCPSKIRRKANASCKKCKKVICREHNIDMCQ<br>SCF |
| 10 | LLT<br>(I247L<br>I147L<br>S533T) | MGSSLDDEHILSALLQSDDELVGEDSDSEISDHVSEDDVQSDT<br>EEAFIDE<br>VHEVQPTSSGSEILDEQNVIEQPGSSLASNRILTLPQRTIRGKN<br>KHCWST<br>SKSTRRSRVSALNIVRSQRGPTRMCRNIYDPLLCFKLFFTDEII<br>SELVKW<br>TNAEISLKRRESMTGATFRDTNEDEIYAFFGILVMTAVRKDN<br>HMSTDDLF<br>DRSLSMVYVSVMSRDRFDFLIRCLRMDDKSIRPTLRENDVFT<br>PVRKLWDL<br>FIHQCIQNYTPGAHLTIDEQLLGFRGRCPFRMYIPNKPSKYGIK<br>ILMMCD<br>SGTKYMINGMPYLGRGTQTNGVPLGEYYVKELSKPVHGSCR<br>NITCDNWFT<br>SIPLAKNLLQEPYKLTIVGTVRSNKREIPEVLKNSRSRPVGTS<br>MFCFDGP<br>LTLVSYKPKPAKMVYLLSSCDEDASINESTGKPQMVMYYNQ<br>TKGGVDTLD |

TABLE 1-continued

Amino acid sequences of wild type and mutated PIGGYBAC ® transposases

| SEQ ID NO: | ID | SEQUENCE |
|---|---|---|
| | | QMCSVMTCSRKTNRWPMALLYGMINIACINSFIIYSHNVSSK GEKVQSRK KFMRNLYMSLTSSFMRKRLEAPTLKRYLRDNITNILPNEVPG TSDDSTEE PVMKKRTYCTYCPSKIRRKANASCKKCKKVICREHNIDMCQ SCF |
| 12 | ILT (I247 I147L S533T) | MGSSLDDEHILSALLQSDDELVGEDSDSEISDHVSEDDVQSDT EEAFIDE VHEVQPTSSGSEILDEQNVIEQPGSSLASNRILTLPQRTIRGKN KHCWST SKSTRRSRVSALNIVRSQRGPTRMCRNIYDPLLCFKLFFTDEII SEIVKW TNAEISLKRRESMTGATFRDTNEDEIYAFFGILVMTAVRKDN HMSTDDLF DRSLSMVYVSVMSRDRFDFLIRCLRMDDKSIRPTLRENDVFT PVRKLWDL FIHQCIQNYTPGAHLTIDEQLLGFRGRCPFRMYIPNKPSKYGIK ILMMCD SGTKYMINGMPYLGRGTQTNGVPLGEYYVKELSKPVHGSCR NITCDNWFT SIPLAKNLLQEPYKLTIVGTVRSNKREIPEVLKNSRSRPVGTS MFCFDGP LTLVSYKPKPAKMVYLLSSCDEDASINESTGKPQMVMYYNQ TKGGVDTLD QMCSVMTCSRKTNRWPMALLYGMINIACINSFIIYSHNVSSK GEKVQSRK KFMRNLYMSLTSSFMRKRLEAPTLKRYLRDNITNILPNEVPG TSDDSTEE PVMKKRTYCTYCPSKIRRKANASCKKCKKVICREHNIDMCQ SCF |
| 14 | LIT (I247L I147 S533T) | MGSSLDDEHILSALLQSDDELVGEDSDSEISDHVSEDDVQSDT EEAFIDE VHEVQPTSSGSEILDEQNVIEQPGSSLASNRILTLPQRTIRGKN KHCWST SKSTRRSRVSALNIVRSQRGPTRMCRNIYDPLLCFKLFFTDEII SELVKW TNAEISLKRRESMTGATFRDTNEDEIYAFFGILVMTAVRKDN HMSTDDLF DRSLSMVYVSVMSRDRFDFLIRCLRMDDKSIRPTLRENDVFT PVRKIWDL FIHQCIQNYTPGAHLTIDEQLLGFRGRCPFRMYIPNKPSKYGIK ILMMCD SGTKYMINGMPYLGRGTQTNGVPLGEYYVKELSKPVHGSCR NITCDNWFT SIPLAKNLLQEPYKLTIVGTVRSNKREIPEVLKNSRSRPVGTS MFCFDGP LTLVSYKPKPAKMVYLLSSCDEDASINESTGKPQMVMYYNQ TKGGVDTLD QMCSVMTCSRKTNRWPMALLYGMINIACINSFIIYSHNVSSK GEKVQSRK KFMRNLYMSLTSSFMRKRLEAPTLKRYLRDNITNILPNEVPG TSDDSTEE PVMKKRTYCTYCPSKIRRKANASCKKCKKVICREHNIDMCQ SCF |
| 16 | LLS (I247L I147L S533) | MGSSLDDEHILSALLQSDDELVGEDSDSEISDHVSEDDVQSDT EEAFIDE VHEVQPTSSGSEILDEQNVIEQPGSSLASNRILTLPQRTIRGKN KHCWST SKSTRRSRVSALNIVRSQRGPTRMCRNIYDPLLCFKLFFTDEII SELVKW TNAEISLKRRESMTGATFRDTNEDEIYAFFGILVMTAVRKDN HMSTDDLF DRSLSMVYVSVMSRDRFDFLIRCLRMDDKSIRPTLRENDVFT PVRKLWDL FIHQCIQNYTPGAHLTIDEQLLGFRGRCPFRMYIPNKPSKYGIK ILMMCD SGTKYMINGMPYLGRGTQTNGVPLGEYYVKELSKPVHGSCR NITCDNWFT SIPLAKNLLQEPYKLTIVGTVRSNKREIPEVLKNSRSRPVGTS MFCFDGP LTLVSYKPKPAKMVYLLSSCDEDASINESTGKPQMVMYYNQ TKGGVDTLD |

TABLE 1-continued

Amino acid sequences of wild type and mutated PIGGYBAC ® transposases

| SEQ ID NO: | ID | SEQUENCE |
|---|---|---|
| | | QMCSVMTCSRKTNRWPMALLYGMINIACINSFIIYSHNVSSK GEKVQSRK KFMRNLYMSLTSSFMRKRLEAPTLKRYLRDNISNILPNEVPG TSDDSTEE PVMKKRTYCTYCPSKIRRKANASCKKCKKVICREHNIDMCQ SCF |

The terms "polynucleotide", "nucleic acid molecule", or "engineered nucleic acid molecule" are used interchangeably throughout and include both single-stranded and double-stranded nucleic acids and includes genomic DNA, RNA, mRNA, cDNA, or synthetic origin or some combination thereof which is not associated with sequences normally found in nature. The terms "isolated polynucleotide", "isolated nucleic acid molecule" or "isolated engineered nucleic acid molecule" specifically refer to sequences of synthetic origin or those not normally found in nature. Isolated nucleic acid molecules comprising specified sequences may include, in addition to the specified sequences, coding sequences for up to ten or even up to twenty other proteins or portions thereof or may include operably linked regulatory sequences that control expression of the coding region of the recited nucleic acid sequences, and/or may include vector sequences. The nucleotides comprising the nucleic acid molecules can be ribonucleotides or deoxyribonucleotides or a modified form of either type of nucleotide. The modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate.

As used herein, the term "isolated" means (i) free of at least some other proteins or polynucleotides with which it would normally be found, (ii) is essentially free of other proteins or polynucleotides from the same source, e.g., from the same species, (iii) separated from at least about 50 percent of polypeptides, polynucleotides, lipids, carbohydrates, or other materials with which it is associated in nature, (iv) operably associated (by covalent or noncovalent interaction) with a polypeptide or polynucleotide with which it is not associated in nature, or (v) does not occur in nature.

In one embodiment the invention provides an engineered nucleic acid molecule encoding a PIGGYBAC® transposase as described herein. The invention also provides a PIGGYBAC® transposase encoded by the nucleic acid sequence of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, or SEQ ID NO: 18. In another aspect the invention provides a PIGGYBAC® transposase encoded by the nucleic acid sequence of SEQ ID NO: 3, SEQ ID NO: 5, or SEQ ID NO: 7. In another aspect the invention provides a PIGGYBAC® transposase encoded by the nucleic acid sequence of SEQ ID NO: 11, SEQ ID NO: 13, or SEQ ID NO: 15. In another aspect the invention provides a PIGGYBAC® transposase encoded by the nucleic acid sequence of SEQ ID NO: 9, or SEQ ID NO: 11. In another aspect the invention provides a PIGGYBAC® transposase encoded by the nucleic acid sequence of SEQ ID NO: 17, or SEQ ID NO: 18. In another aspect the invention provides a PIGGYBAC® transposase encoded by the nucleic acid sequence of SEQ ID NO: 3. In another aspect the invention provides a PIGGYBAC® transposase encoded by the nucleic acid sequence of SEQ ID NO: 5. In another aspect the invention provides a PIGGYBAC® transposase encoded by the nucleic acid sequence of SEQ ID NO: 7. In another aspect the invention provides a PIGGYBAC® transposase encoded by the nucleic acid sequence of SEQ ID NO: 9. In another aspect the invention provides a PIGGYBAC® transposase encoded by the nucleic acid sequence of SEQ ID NO: 11. In another aspect the invention provides a PIGGYBAC® transposase encoded by the nucleic acid sequence of SEQ ID NO: 13. In another aspect the invention provides a PIGGYBAC® transposase encoded by the nucleic acid sequence of SEQ ID NO: 15. In another aspect the invention provides a PIGGYBAC® transposase encoded by the nucleic acid sequence of SEQ ID NO: 17. In another aspect the invention provides a PIGGYBAC® transposase encoded by the nucleic acid sequence of SEQ ID NO: 18.

TABLE 2

Nucleic acid sequences of wild type and mutated PIGGYBAC® transposases

| SEQ ID NO: | ID | NUCLEIC ACID SEQUENCE |
|---|---|---|
| 1 | WT | ATGGGCTCTAGCCTGGACGACGAGCACATCCTGAGCGCCC TGCTGCAG AGCGACGACGAACTGGTGGGCGAGGACAGCGACAGCGAG ATCAGCGACCA CGTGTCCGAGGACGACGTGCAGTCCGACACCGAGGAAGC CTTCATCGACG AGGTGCACGAAGTGCAGCCTACCAGCAGCGGCTCCGAGAT CCTGGACGAG CAGAACGTGATCGAGCAGCCTGGCAGCTCCCTGGCCAGCA ACAGAATCCT |

TABLE 2-continued

Nucleic acid sequences of wild type and mutated PIGGYBAC®
transposases

| SEQ ID NO: | ID | NUCLEIC ACID SEQUENCE |
|---|---|---|
| | | GACCCTGCCCCAGAGAACCATCAGAGGCAAGAACAAGCA CTGCTGGTCCA |
| | | CCTCCAAGAGCACCAGGCGGAGCAGAGTGTCCGCCCTGAA CATCGTGCGG |
| | | AGCCAGAGGGGCCCCACCAGAATGTGCAGAAACATCTAC GACCCCCTGCT |
| | | GTGCTTCAAGCTGTTCTTCACCGACGAGATCATCAGCGAG ATCGTGAAGT |
| | | GGACCAACGCCGAGATCAGCCTGAAGAGGCGGGAGAGCA TGACCGGCGCC |
| | | ACCTTCAGAGACACCAACGAGGACGAGATCTACGCCTTCT TCGGCATCCT |
| | | GGTGATGACCGCCGTGAGAAAGGACAACCACATGAGCAC CGACGACCTGT |
| | | TCGACAGATCCCTGAGCATGGTGTACGTGTCCGTGATGAG CAGAGACAGA |
| | | TTCGACTTCCTGATCAGATGCCTGAGAATGGACGACAAGA GCATCAGACC |
| | | CACCCTGCGGGAGAACGACGTGTTCACCCCCGTGCGGAAG ATCTGGGACC |
| | | TGTTCATCCACCAGTGCATCCAGAACTACACCCCTGGCGC CCACCTGACC |
| | | ATCGATGAGCAGCTGCTGGGCTTCAGAGGCAGATGCCCCT TCAGAATGTA |
| | | CATCCCCAACAAGCCCAGCAAGTACGGCATCAAGATCCTG ATGATGTGCG |
| | | ACAGCGGCACCAAGTACATGATCAACGGCATGCCCTACCT GGGCAGAGGC |
| | | ACCCAGACAAACGGCGTGCCCCTGGGCGAGTACTACGTGA AAGAACTGAG |
| | | CAAGCCTGTGCATGGCAGCTGCAGGAACATCACCTGCGAC AACTGGTTCA |
| | | CCAGCATCCCCCTGGCCAAGAACCTGCTGCAGGAACCCTA CAAGCTGACC |
| | | ATCGTGGGCACCGTGCGGAGCAACAAGCGGGAGATCCCA GAGGTGCTGAA |
| | | GAACAGCAGATCCAGACCTGTGGGAACAAGCATGTTCTGC TTCGACGGCC |
| | | CCCTGACCCTGGTGTCCTACAAGCCCAAGCCCGCCAAGAT GGTGTACCTG |
| | | CTGTCCAGCTGCGACGAGGACGCCAGCATCAACGAGAGC ACCGGCAAGCC |
| | | CCAGATGGTGATGTACTACAACCAGACCAAGGGCGGCGTG GACACCCTGG |
| | | ACCAGATGTGCAGCGTGATGACCTGCAGCAGAAAGACCA ACAGATGGCCC |
| | | ATGGCCCTGCTGTACGGCATGATCAATATCGCCTGCATCA ACAGCTTCAT |
| | | CATCTACAGCCACAACGTGTCCAGCAAGGGCGAGAAGGT GCAGAGCCGGA |
| | | AGAAATTCATGCGGAACCTGTACATGAGCCTGACCTCCAG CTTCATGAGA |
| | | AAGAGACTGGAAGCCCCCACCCTGAAGAGATACCTGCGG GACAACATCAG |
| | | CAACATCCTGCCCAACGAAGTGCCAGGAACAAGCGACGA CAGCACCGAGG |
| | | AACCCGTGATGAAGAAGAGGACCTACTGCACCTACTGTCC CAGCAAGATC |
| | | AGAAGAAAGGCCAACGCCAGCTGCAAGAAATGCAAAAAA GTGATCTGCCG |
| | | GGAGCACAACATCGACATGTGCCAGAGCTGTTTCTAGC |
| 3 | I147L | ATGGGCTCTAGCCTGGACGACGAGCACATCCTGAGCGCCC TGCTGCAG |
| | | AGCGACGACGAACTGGTGGGCGAGGACAGCGACAGCGAG ATCAGCGACCA |
| | | CGTGTCCGAGGACGACGTGCAGTCCGACACCGAGGAAGC CTTCATCGACG |
| | | AGGTGCACGAAGTGCAGCCTACCAGCAGCGGCTCCGAGAT CCTGGACGAG |
| | | CAGAACGTGATCGAGCAGCCTGGCAGCTCCCTGGCCAGCA ACAGAATCCT |

TABLE 2-continued

Nucleic acid sequences of wild type and mutated PIGGYBAC®
transposases

| SEQ ID NO: | ID | NUCLEIC ACID SEQUENCE |
|---|---|---|
| | | GACCCTGCCCCAGAGAACCATCAGAGGCAAGAACAAGCA |
| | | CTGCTGGTCCA |
| | | CCTCCAAGAGCACCAGGCGGAGCAGAGTGTCCGCCCTGAA |
| | | CATCGTGCGG |
| | | AGCCAGAGGGGCCCCACCAGAATGTGCAGAAACATCTAC |
| | | GACCCCCTGCT |
| | | GTGCTTCAAGCTGTTCTTCACCGACGAGATCATCAGCGAG |
| | | CTGGTGAAGT |
| | | GGACCAACGCCGAGATCAGCCTGAAGAGGCGGGAGAGCA |
| | | TGACCGGCGCC |
| | | ACCTTCAGAGACACCAACGAGGACGAGATCTACGCCTTCT |
| | | TCGGCATCCT |
| | | GGTGATGACCGCCGTGAGAAAGGACAACCACATGAGCAC |
| | | CGACGACCTGT |
| | | TCGACAGATCCCTGAGCATGGTGTACGTGTCCGTGATGAG |
| | | CAGAGACAGA |
| | | TTCGACTTCCTGATCAGATGCCTGAGAATGGACGACAAGA |
| | | GCATCAGACC |
| | | CACCCTGCGGGAGAACGACGTGTTCACCCCCGTGCGGAAG |
| | | ATCTGGGACC |
| | | TGTTCATCCACCAGTGCATCCAGAACTACACCCCTGGCGC |
| | | CCACCTGACC |
| | | ATCGATGAGCAGCTGCTGGGCTTCAGAGGCAGATGCCCCT |
| | | TCAGAATGTA |
| | | CATCCCCAACAAGCCCAGCAAGTACGGCATCAAGATCCTG |
| | | ATGATGTGCG |
| | | ACAGCGGCACCAAGTACATGATCAACGGCATGCCCTACCT |
| | | GGGCAGAGGC |
| | | ACCCAGACAAACGGCGTGCCCCTGGGCGAGTACTACGTGA |
| | | AAGAACTGAG |
| | | CAAGCCTGTGCATGGCAGCTGCAGGAACATCACCTGCGAC |
| | | AACTGGTTCA |
| | | CCAGCATCCCCCTGGCCAAGAACCTGCTGCAGGAACCCTA |
| | | CAAGCTGACC |
| | | ATCGTGGGCACCGTGCGGAGCAACAAGCGGGAGATCCCA |
| | | GAGGTGCTGAA |
| | | GAACAGCAGATCCAGACCTGTGGGAACAAGCATGTTCTGC |
| | | TTCGACGGCC |
| | | CCCTGACCCTGGTGTCCTACAAGCCCAAGCCCGCCAAGAT |
| | | GGTGTACCTG |
| | | CTGTCCAGCTGCGACGAGGACGCCAGCATCAACGAGAGC |
| | | ACCGGCAAGCC |
| | | CCAGATGGTGATGTACTACAACCAGACCAAGGGCGGCGTG |
| | | GACACCCTGG |
| | | ACCAGATGTGCAGCGTGATGACCTGCAGCAGAAAGACCA |
| | | ACAGATGGCCC |
| | | ATGGCCCTGCTGTACGGCATGATCAATATCGCCTGCATCA |
| | | ACAGCTTCAT |
| | | CATCTACAGCCACAACGTGTCCAGCAAGGGCGAGAAGGT |
| | | GCAGAGCCGGA |
| | | AGAAATTCATGCGGAACCTGTACATGAGCCTGACCTCCAG |
| | | CTTCATGAGA |
| | | AAGAGACTGGAAGCCCCCACCCTGAAGAGATACCTGCGG |
| | | GACAACATCAG |
| | | CAACATCCTGCCCAACGAAGTGCCAGGAACAAGCGACGA |
| | | CAGCACCGAGG |
| | | AACCCGTGATGAAGAAGAGGACCTACTGCACCTACTGTCC |
| | | CAGCAAGATC |
| | | AGAAGAAAGGCCAACGCCAGCTGCAAGAAATGCAAAAAA |
| | | GTGATCTGCCG |
| | | GGAGCACAACATCGACATGTGCCAGAGCTGTTTCTAGC |
| 5 | I247L | ATGGGCTCTAGCCTGGACGACGAGCACATCCTGAGCGCCC |
| | | TGCTGCAG |
| | | AGCGACGACGAACTGGTGGGCGAGGACAGCGACAGCGAG |
| | | ATCAGCGACCA |
| | | CGTGTCCGAGGACGACGTGCAGTCCGACACCGAGGAAGC |
| | | CTTCATCGACG |
| | | AGGTGCACGAAGTGCAGCCTACCAGCAGCGGCTCCGAGAT |
| | | CCTGGACGAG |
| | | CAGAACGTGATCGAGCAGCCTGGCAGCTCCCTGGCCAGCA |
| | | ACAGAATCCT |

TABLE 2-continued

Nucleic acid sequences of wild type and mutated PIGGYBAC®
transposases

| SEQ ID NO: | ID | NUCLEIC ACID SEQUENCE |
|---|---|---|
| | | GACCCTGCCCCAGAGAACCATCAGAGGCAAGAACAAGCA |
| | | CTGCTGGTCCA |
| | | CCTCCAAGAGCACCAGGCGGAGCAGAGTGTCCGCCCTGAA |
| | | CATCGTGCGG |
| | | AGCCAGAGGGGCCCCACCAGAATGTGCAGAAACATCTAC |
| | | GACCCCCTGCT |
| | | GTGCTTCAAGCTGTTCTTCACCGACGAGATCATCAGCGAG |
| | | ATCGTGAAGT |
| | | GGACCAACGCCGAGATCAGCCTGAAGAGGCGGGAGAGCA |
| | | TGACCGGCGCC |
| | | ACCTTCAGAGACACCAACGAGGACGAGATCTACGCCTTCT |
| | | TCGGCATCCT |
| | | GGTGATGACCGCCGTGAGAAAGGACAACCACATGAGCAC |
| | | CGACGACCTGT |
| | | TCGACAGATCCCTGAGCATGGTGTACGTGTCCGTGATGAG |
| | | CAGAGACAGA |
| | | TTCGACTTCCTGATCAGATGCCTGAGAATGGACGACAAGA |
| | | GCATCAGACC |
| | | CACCCTGCGGGAGAACGACGTGTTCACCCCCGTGCGGAAG |
| | | CTGTGGGACC |
| | | TGTTCATCCACCAGTGCATCCAGAACTACACCCCTGGCGC |
| | | CCACCTGACC |
| | | ATCGATGAGCAGCTGCTGGGCTTCAGAGGCAGATGCCCCT |
| | | TCAGAATGTA |
| | | CATCCCCAACAAGCCCAGCAAGTACGGCATCAAGATCCTG |
| | | ATGATGTGCG |
| | | ACAGCGGCACCAAGTACATGATCAACGGCATGCCCTACCT |
| | | GGGCAGAGGC |
| | | ACCCAGACAAACGGCGTGCCCCTGGGCGAGTACTACGTGA |
| | | AAGAACTGAG |
| | | CAAGCCTGTGCATGGCAGCTGCAGGAACATCACCTGCGAC |
| | | AACTGGTTCA |
| | | CCAGCATCCCCCTGGCCAAGAACCTGCTGCAGGAACCCTA |
| | | CAAGCTGACC |
| | | ATCGTGGGCACCGTGCGGAGCAACAAGCGGGAGATCCCA |
| | | GAGGTGCTGAA |
| | | GAACAGCAGATCCAGACCTGTGGGAACAAGCATGTTCTGC |
| | | TTCGACGGCC |
| | | CCCTGACCCTGGTGTCCTACAAGCCCAAGCCCGCCAAGAT |
| | | GGTGTACCTG |
| | | CTGTCCAGCTGCGACGAGGACGCCAGCATCAACGAGAGC |
| | | ACCGGCAAGCC |
| | | CCAGATGGTGATGTACTACAACCAGACCAAGGGCGGCGTG |
| | | GACACCCTGG |
| | | ACCAGATGTGCAGCGTGATGACCTGCAGCAGAAAGACCA |
| | | ACAGATGGCCC |
| | | ATGGCCCTGCTGTACGGCATGATCAATATCGCCTGCATCA |
| | | ACAGCTTCAT |
| | | CATCTACAGCCACAACGTGTCCAGCAAGGGCGAGAAGGT |
| | | GCAGAGCCGGA |
| | | AGAAATTCATGCGGAACCTGTACATGAGCCTGACCTCCAG |
| | | CTTCATGAGA |
| | | AAGAGACTGGAAGCCCCCACCCTGAAGAGATACCTGCGG |
| | | GACAACATCAG |
| | | CAACATCCTGCCCAACGAAGTGCCAGGAACAAGCGACGA |
| | | CAGCACCGAGG |
| | | AACCCGTGATGAAGAAGAGGACCTACTGCACCTACTGTCC |
| | | CAGCAAGATC |
| | | AGAAGAAAGGCCAACGCCAGCTGCAAGAAATGCAAAAAA |
| | | GTGATCTGCCG |
| | | GGAGCACAACATCGACATGTGCCAGAGCTGTTTCTAGC |
| 7 | S533T | ATGGGCTCTAGCCTGGACGACGAGCACATCCTGAGCGCCC |
| | | TGCTGCAG |
| | | AGCGACGACGAACTGGTGGGCGAGGACAGCGACAGCGAG |
| | | ATCAGCGACCA |
| | | CGTGTCCGAGGACGACGTGCAGTCCGACACCGAGGAAGC |
| | | CTTCATCGACG |
| | | AGGTGCACGAAGTGCAGCCTACCAGCAGCGGCTCCGAGAT |
| | | CCTGGACGAG |
| | | CAGAACGTGATCGAGCAGCCTGGCAGCTCCCTGGCCAGCA |
| | | ACAGAATCCT |

TABLE 2-continued

Nucleic acid sequences of wild type and mutated PIGGYBAC®
transposases

| SEQ ID NO: | ID | NUCLEIC ACID SEQUENCE |
|---|---|---|
| | | GACCCTGCCCCAGAGAACCATCAGAGGCAAGAACAAGCA |
| | | CTGCTGGTCCA |
| | | CCTCCAAGAGCACCAGGCGGAGCAGAGTGTCCGCCCTGAA |
| | | CATCGTGCGG |
| | | AGCCAGAGGGGCCCCACCAGAATGTGCAGAAACATCTAC |
| | | GACCCCCTGCT |
| | | GTGCTTCAAGCTGTTCTTCACCGACGAGATCATCAGCGAG |
| | | ATCGTGAAGT |
| | | GGACCAACGCCGAGATCAGCCTGAAGAGGCGGGAGAGCA |
| | | TGACCGGCGCC |
| | | ACCTTCAGAGACACCAACGAGGACGAGATCTACGCCTTCT |
| | | TCGGCATCCT |
| | | GGTGATGACCGCCGTGAGAAAGGACAACCACATGAGCAC |
| | | CGACGACCTGT |
| | | TCGACAGATCCCTGAGCATGGTGTACGTGTCCGTGATGAG |
| | | CAGAGACAGA |
| | | TTCGACTTCCTGATCAGATGCCTGAGAATGGACGACAAGA |
| | | GCATCAGACC |
| | | CACCCTGCGGGAGAACGACGTGTTCACCCCCGTGCGGAAG |
| | | ATCTGGGACC |
| | | TGTTCATCCACCAGTGCATCCAGAACTACACCCCTGGCGC |
| | | CCACCTGACC |
| | | ATCGATGAGCAGCTGCTGGGCTTCAGAGGCAGATGCCCCT |
| | | TCAGAATGTA |
| | | CATCCCCAACAAGCCCAGCAAGTACGGCATCAAGATCCTG |
| | | ATGATGTGCG |
| | | ACAGCGGCACCAAGTACATGATCAACGGCATGCCCTACCT |
| | | GGGCAGAGGC |
| | | ACCCAGACAAACGGCGTGCCCCTGGGCGAGTACTACGTGA |
| | | AAGAACTGAG |
| | | CAAGCCTGTGCATGGCAGCTGCAGGAACATCACCTGCGAC |
| | | AACTGGTTCA |
| | | CCAGCATCCCCCTGGCCAAGAACCTGCTGCAGGAACCCTA |
| | | CAAGCTGACC |
| | | ATCGTGGGCACCGTGCGGAGCAACAAGCGGGAGATCCCA |
| | | GAGGTGCTGAA |
| | | GAACAGCAGATCCAGACCTGTGGGAACAAGCATGTTCTGC |
| | | TTCGACGGCC |
| | | CCCTGACCCTGGTGTCCTACAAGCCCAAGCCCGCCAAGAT |
| | | GGTGTACCTG |
| | | CTGTCCAGCTGCGACGAGGACGCCAGCATCAACGAGAGC |
| | | ACCGGCAAGCC |
| | | CCAGATGGTGATGTACTACAACCAGACCAAGGGCGGCGTG |
| | | GACACCCTGG |
| | | ACCAGATGTGCAGCGTGATGACCTGCAGCAGAAAGACCA |
| | | ACAGATGGCCC |
| | | ATGGCCCTGCTGTACGGCATGATCAATATCGCCTGCATCA |
| | | ACAGCTTCAT |
| | | CATCTACAGCCACAACGTGTCCAGCAAGGGCGAGAAGGT |
| | | GCAGAGCCGGA |
| | | AGAAATTCATGCGGAACCTGTACATGAGCCTGACCTCCAG |
| | | CTTCATGAGA |
| | | AAGAGACTGGAAGCCCCCACCCTGAAGAGATACCTGCGG |
| | | GACAACATCAC |
| | | CAACATCCTGCCCAACGAAGTGCCAGGAACAAGCGACGA |
| | | CAGCACCGAGG |
| | | AACCCGTGATGAAGAAGAGGACCTACTGCACCTACTGTCC |
| | | CAGCAAGATC |
| | | AGAAGAAAGGCCAACGCCAGCTGCAAGAAATGCAAAAAA |
| | | GTGATCTGCCG |
| | | GGAGCACAACATCGACATGTGCCAGAGCTGTTTCTAGC |
| 9 | LLT (I247L I147L S533T) | ATGGGCTCTAGCCTGGACGACGAGCACATCCTGAGCGCCC |
| | | TGCTGCAG |
| | | AGCGACGACGAACTGGTGGGCGAGGACAGCGACAGCGAG |
| | | ATCAGCGACCA |
| | | CGTGTCCGAGGACGACGTGCAGTCCGACACCGAGGAAGC |
| | | CTTCATCGACG |
| | | AGGTGCACGAAGTGCAGCCTACCAGCAGCGGCTCCGAGAT |
| | | CCTGGACGAG |
| | | CAGAACGTGATCGAGCAGCCTGGCAGCTCCCTGGCCAGCA |
| | | ACAGAATCCT |

TABLE 2-continued

Nucleic acid sequences of wild type and mutated PIGGYBAC®
transposases

| SEQ ID NO: | ID | NUCLEIC ACID SEQUENCE |
|---|---|---|
| | | GACCCTGCCCCAGAGAACCATCAGAGGCAAGAACAAGCA |
| | | CTGCTGGTCCA |
| | | CCTCCAAGAGCACCAGGCGGAGCAGAGTGTCCGCCCTGAA |
| | | CATCGTGCGG |
| | | AGCCAGAGGGGCCCCACCAGAATGTGCAGAAACATCTAC |
| | | GACCCCCTGCT |
| | | GTGCTTCAAGCTGTTCTTCACCGACGAGATCATCAGCGAG |
| | | CTGGTGAAGT |
| | | GGACCAACGCCGAGATCAGCCTGAAGAGGCGGGAGAGCA |
| | | TGACCGGCGCC |
| | | ACCTTCAGAGACACCAACGAGGACGAGATCTACGCCTTCT |
| | | TCGGCATCCT |
| | | GGTGATGACCGCCGTGAGAAAGGACAACCACATGAGCAC |
| | | CGACGACCTGT |
| | | TCGACAGATCCCTGAGCATGGTGTACGTGTCCGTGATGAG |
| | | CAGAGACAGA |
| | | TTCGACTTCCTGATCAGATGCCTGAGAATGGACGACAAGA |
| | | GCATCAGACC |
| | | CACCCTGCGGGAGAACGACGTGTTCACCCCCGTGCGGAAG |
| | | CTGTGGGACC |
| | | TGTTCATCCACCAGTGCATCCAGAACTACACCCCTGGCGC |
| | | CCACCTGACC |
| | | ATCGATGAGCAGCTGCTGGGCTTCAGAGGCAGATGCCCCT |
| | | TCAGAATGTA |
| | | CATCCCCAACAAGCCCAGCAAGTACGGCATCAAGATCCTG |
| | | ATGATGTGCG |
| | | ACAGCGGCACCAAGTACATGATCAACGGCATGCCCTACCT |
| | | GGGCAGAGGC |
| | | ACCCAGACAAACGGCGTGCCCCTGGGCGAGTACTACGTGA |
| | | AAGAACTGAG |
| | | CAAGCCTGTGCATGGCAGCTGCAGGAACATCACCTGCGAC |
| | | AACTGGTTCA |
| | | CCAGCATCCCCCTGGCCAAGAACCTGCTGCAGGAACCCTA |
| | | CAAGCTGACC |
| | | ATCGTGGGCACCGTGCGGAGCAACAAGCGGGAGATCCCA |
| | | GAGGTGCTGAA |
| | | GAACAGCAGATCCAGACCTGTGGGAACAAGCATGTTCTGC |
| | | TTCGACGGCC |
| | | CCCTGACCCTGGTGTCCTACAAGCCCAAGCCCGCCAAGAT |
| | | GGTGTACCTG |
| | | CTGTCCAGCTGCGACGAGGACGCCAGCATCAACGAGAGC |
| | | ACCGGCAAGCC |
| | | CCAGATGGTGATGTACTACAACCAGACCAAGGGCGGCGTG |
| | | GACACCCTGG |
| | | ACCAGATGTGCAGCGTGATGACCTGCAGCAGAAAGACCA |
| | | ACAGATGGCCC |
| | | ATGGCCCTGCTGTACGGCATGATCAATATCGCCTGCATCA |
| | | ACAGCTTCAT |
| | | CATCTACAGCCACAACGTGTCCAGCAAGGGCGAGAAGGT |
| | | GCAGAGCCGGA |
| | | AGAAATTCATGCGGAACCTGTACATGAGCCTGACCTCCAG |
| | | CTTCATGAGA |
| | | AAGAGACTGGAAGCCCCCACCCTGAAGAGATACCTGCGG |
| | | GACAACATCAC |
| | | CAACATCCTGCCCAACGAAGTGCCAGGAACAAGCGACGA |
| | | CAGCACCGAGG |
| | | AACCCGTGATGAAGAAGAGGACCTACTGCACCTACTGTCC |
| | | CAGCAAGATC |
| | | AGAAGAAAGGCCAACGCCAGCTGCAAGAAATGCAAAAAA |
| | | GTGATCTGCCG |
| | | GGAGCACAACATCGACATGTGCCAGAGCTGTTTCTAGC |
| | | | |
| 11 | ILT (I147 I247L S533T) | ATGGGCTCTAGCCTGGACGACGAGCACATCCTGAGCGCCC TGCTGCAG |
| | | AGCGACGACGAACTGGTGGGCGAGGACAGCGACAGCGAG ATCAGCGACCA |
| | | CGTGTCCGAGGACGACGTGCAGTCCGACACCGAGGAAGC CTTCATCGACG |
| | | AGGTGCACGAAGTGCAGCCTACCAGCAGCGGCTCCGAGAT CCTGGACGAG |
| | | CAGAACGTGATCGAGCAGCCTGGCAGCTCCCTGGCCAGCA ACAGAATCCT |

TABLE 2-continued

Nucleic acid sequences of wild type and mutated PIGGYBAC® transposases

| SEQ ID NO: | ID | NUCLEIC ACID SEQUENCE |
|---|---|---|
| | | GACCCTGCCCCAGAGAACCATCAGAGGCAAGAACAAGCA |
| | | CTGCTGGTCCA |
| | | CCTCCAAGAGCACCAGGCGGAGCAGAGTGTCCGCCCTGAA |
| | | CATCGTGCGG |
| | | AGCCAGAGGGGCCCCACCAGAATGTGCAGAAACATCTAC |
| | | GACCCCCTGCT |
| | | GTGCTTCAAGCTGTTCTTCACCGACGAGATCATCAGCGAG |
| | | ATCGTGAAGT |
| | | GGACCAACGCCGAGATCAGCCTGAAGAGGCGGGAGAGCA |
| | | TGACCGGCGCC |
| | | ACCTTCAGAGACACCAACGAGGACGAGATCTACGCCTTCT |
| | | TCGGCATCCT |
| | | GGTGATGACCGCCGTGAGAAAGGACAACCACATGAGCAC |
| | | CGACGACCTGT |
| | | TCGACAGATCCCTGAGCATGGTGTACGTGTCCGTGATGAG |
| | | CAGAGACAGA |
| | | TTCGACTTCCTGATCAGATGCCTGAGAATGGACGACAAGA |
| | | GCATCAGACC |
| | | CACCCTGCGGGAGAACGACGTGTTCACCCCCGTGCGGAAG |
| | | CTGTGGGACC |
| | | TGTTCATCCACCAGTGCATCCAGAACTACACCCCTGGCGC |
| | | CCACCTGACC |
| | | ATCGATGAGCAGCTGCTGGGCTTCAGAGGCAGATGCCCCT |
| | | TCAGAATGTA |
| | | CATCCCCAACAAGCCCAGCAAGTACGGCATCAAGATCCTG |
| | | ATGATGTGCG |
| | | ACAGCGGCACCAAGTACATGATCAACGGCATGCCCTACCT |
| | | GGGCAGAGGC |
| | | ACCCAGACAAACGGCGTGCCCCTGGGCGAGTACTACGTGA |
| | | AAGAACTGAG |
| | | CAAGCCTGTGCATGGCAGCTGCAGGAACATCACCTGCGAC |
| | | AACTGGTTCA |
| | | CCAGCATCCCCCTGGCCAAGAACCTGCTGCAGGAACCCTA |
| | | CAAGCTGACC |
| | | ATCGTGGGCACCGTGCGGAGCAACAAGCGGGAGATCCCA |
| | | GAGGTGCTGAA |
| | | GAACAGCAGATCCAGACCTGTGGGAACAAGCATGTTCTGC |
| | | TTCGACGGCC |
| | | CCCTGACCCTGGTGTCCTACAAGCCCAAGCCCGCCAAGAT |
| | | GGTGTACCTG |
| | | CTGTCCAGCTGCGACGAGGACGCCAGCATCAACGAGAGC |
| | | ACCGGCAAGCC |
| | | CCAGATGGTGATGTACTACAACCAGACCAAGGGCGGCGTG |
| | | GACACCCTGG |
| | | ACCAGATGTGCAGCGTGATGACCTGCAGCAGAAAGACCA |
| | | ACAGATGGCCC |
| | | ATGGCCCTGCTGTACGGCATGATCAATATCGCCTGCATCA |
| | | ACAGCTTCAT |
| | | CATCTACAGCCACAACGTGTCCAGCAAGGGCGAGAAGGT |
| | | GCAGAGCCGGA |
| | | AGAAATTCATGCGGAACCTGTACATGAGCCTGACCTCCAG |
| | | CTTCATGAGA |
| | | AAGAGACTGGAAGCCCCCACCCTGAAGAGATACCTGCGG |
| | | GACAACATCAC |
| | | CAACATCCTGCCCAACGAAGTGCCAGGAACAAGCGACGA |
| | | CAGCACCGAGG |
| | | AACCCGTGATGAAGAAGAGGACCTACTGCACCTACTGTCC |
| | | CAGCAAGATC |
| | | AGAAGAAAGGCCAACGCCAGCTGCAAGAAATGCAAAAAA |
| | | GTGATCTGCCG |
| | | GGAGCACAACATCGACATGTGCCAGAGCTGTTTCTAGC |
| 13 | LIT (I147L I247 S533T) | ATGGGCTCTAGCCTGGACGACGAGCACATCCTGAGCGCCC |
| | | TGCTGCAG |
| | | AGCGACGACGAACTGGTGGGCGAGGACAGCGACAGCGAG |
| | | ATCAGCGACCA |
| | | CGTGTCCGAGGACGACGTGCAGTCCGACACCGAGGAAGC |
| | | CTTCATCGACG |
| | | AGGTGCACGAAGTGCAGCCTACCAGCAGCGGCTCCGAGAT |
| | | CCTGGACGAG |
| | | CAGAACGTGATCGAGCAGCCTGGCAGCTCCCTGGCCAGCA |
| | | ACAGAATCCT |

31
32

TABLE 2-continued

Nucleic acid sequences of wild type and mutated PIGGYBAC®
transposases

| SEQ ID NO: | ID | NUCLEIC ACID SEQUENCE |
|---|---|---|
| | | GACCCTGCCCCAGAGAACCATCAGAGGCAAGAACAAGCA |
| | | CTGCTGGTCCA |
| | | CCTCCAAGAGCACCAGGCGGAGCAGAGTGTCCGCCCTGAA |
| | | CATCGTGCGG |
| | | AGCCAGAGGGGCCCCACCAGAATGTGCAGAAACATCTAC |
| | | GACCCCCTGCT |
| | | GTGCTTCAAGCTGTTCTTCACCGACGAGATCATCAGCGAG |
| | | CTGGTGAAGT |
| | | GGACCAACGCCGAGATCAGCCTGAAGAGGCGGGAGAGCA |
| | | TGACCGGCGCC |
| | | ACCTTCAGAGACACCAACGAGGACGAGATCTACGCCTTCT |
| | | TCGGCATCCT |
| | | GGTGATGACCGCCGTGAGAAAGGACAACCACATGAGCAC |
| | | CGACGACCTGT |
| | | TCGACAGATCCCTGAGCATGGTGTACGTGTCCGTGATGAG |
| | | CAGAGACAGA |
| | | TTCGACTTCCTGATCAGATGCCTGAGAATGGACGACAAGA |
| | | GCATCAGACC |
| | | CACCCTGCGGGAGAACGACGTGTTCACCCCCGTGCGGAAG |
| | | ATCTGGGACC |
| | | TGTTCATCCACCAGTGCATCCAGAACTACACCCCTGGCGC |
| | | CCACCTGACC |
| | | ATCGATGAGCAGCTGCTGGGCTTCAGAGGCAGATGCCCCT |
| | | TCAGAATGTA |
| | | CATCCCCAACAAGCCCAGCAAGTACGGCATCAAGATCCTG |
| | | ATGATGTGCG |
| | | ACAGCGGCACCAAGTACATGATCAACGGCATGCCCTACCT |
| | | GGGCAGAGGC |
| | | ACCCAGACAAACGGCGTGCCCCTGGGCGAGTACTACGTGA |
| | | AAGAACTGAG |
| | | CAAGCCTGTGCATGGCAGCTGCAGGAACATCACCTGCGAC |
| | | AACTGGTTCA |
| | | CCAGCATCCCCCTGGCCAAGAACCTGCTGCAGGAACCCTA |
| | | CAAGCTGACC |
| | | ATCGTGGGCACCGTGCGGAGCAACAAGCGGGAGATCCCA |
| | | GAGGTGCTGAA |
| | | GAACAGCAGATCCAGACCTGTGGGAACAAGCATGTTCTGC |
| | | TTCGACGGCC |
| | | CCCTGACCCTGGTGTCCTACAAGCCCAAGCCCGCCAAGAT |
| | | GGTGTACCTG |
| | | CTGTCCAGCTGCGACGAGGACGCCAGCATCAACGAGAGC |
| | | ACCGGCAAGCC |
| | | CCAGATGGTGATGTACTACAACCAGACCAAGGGCGGCGTG |
| | | GACACCCTGG |
| | | ACCAGATGTGCAGCGTGATGACCTGCAGCAGAAAGACCA |
| | | ACAGATGGCCC |
| | | ATGGCCCTGCTGTACGGCATGATCAATATCGCCTGCATCA |
| | | ACAGCTTCAT |
| | | CATCTACAGCCACAACGTGTCCAGCAAGGGCGAGAAGGT |
| | | GCAGAGCCGGA |
| | | AGAAATTCATGCGGAACCTGTACATGAGCCTGACCTCCAG |
| | | CTTCATGAGA |
| | | AAGAGACTGGAAGCCCCCACCCTGAAGAGATACCTGCGG |
| | | GACAACATCAC |
| | | CAACATCCTGCCCAACGAAGTGCCAGGAACAAGCGACGA |
| | | CAGCACCGAGG |
| | | AACCCGTGATGAAGAAGAGGACCTACTGCACCTACTGTCC |
| | | CAGCAAGATC |
| | | AGAAGAAAGGCCAACGCCAGCTGCAAGAAATGCAAAAAA |
| | | GTGATCTGCCG |
| | | GGAGCACAACATCGACATGTGCCAGAGCTGTTTCTAGC |
| | | |
| 15 | LLS (I147L I247L S533S) | ATGGGCTCTAGCCTGGACGACGAGCACATCCTGAGCGCCC |
| | | TGCTGCAG |
| | | AGCGACGACGAACTGGTGGGCGAGGACAGCGACAGCGAG |
| | | ATCAGCGACCA |
| | | CGTGTCCGAGGACGACGTGCAGTCCGACACCGAGGAAGC |
| | | CTTCATCGACG |
| | | AGGTGCACGAAGTGCAGCCTACCAGCAGCGGCTCCGAGAT |
| | | CCTGGACGAG |
| | | CAGAACGTGATCGAGCAGCCTGGCAGCTCCCTGGCCAGCA |
| | | ACAGAATCCT |

TABLE 2-continued

Nucleic acid sequences of wild type and mutated PIGGYBAC®
transposases

| SEQ ID NO: | ID | NUCLEIC ACID SEQUENCE |
|---|---|---|
| | | GACCCTGCCCCAGAGAACCATCAGAGGCAAGAACAAGCA |
| | | CTGCTGGTCCA |
| | | CCTCCAAGAGCACCAGGCGGAGCAGAGTGTCCGCCCTGAA |
| | | CATCGTGCGG |
| | | AGCCAGAGGGGCCCCACCAGAATGTGCAGAAACATCTAC |
| | | GACCCCCTGCT |
| | | GTGCTTCAAGCTGTTCTTCACCGACGAGATCATCAGCGAG |
| | | CTGGTGAAGT |
| | | GGACCAACGCCGAGATCAGCCTGAAGAGGCGGGAGAGCA |
| | | TGACCGGCGCC |
| | | ACCTTCAGAGACACCAACGAGGACGAGATCTACGCCTTCT |
| | | TCGGCATCCT |
| | | GGTGATGACCGCCGTGAGAAAGGACAACCACATGAGCAC |
| | | CGACGACCTGT |
| | | TCGACAGATCCCTGAGCATGGTGTACGTGTCCGTGATGAG |
| | | CAGAGACAGA |
| | | TTCGACTTCCTGATCAGATGCCTGAGAATGGACGACAAGA |
| | | GCATCAGACC |
| | | CACCCTGCGGGAGAACGACGTGTTCACCCCCGTGCGGAAG |
| | | CTGTGGGACC |
| | | TGTTCATCCACCAGTGCATCCAGAACTACACCCCTGGCGC |
| | | CCACCTGACC |
| | | ATCGATGAGCAGCTGCTGGGCTTCAGAGGCAGATGCCCCT |
| | | TCAGAATGTA |
| | | CATCCCCAACAAGCCCAGCAAGTACGGCATCAAGATCCTG |
| | | ATGATGTGCG |
| | | ACAGCGGCACCAAGTACATGATCAACGGCATGCCCTACCT |
| | | GGGCAGAGGC |
| | | ACCCAGACAAACGGCGTGCCCCTGGGCGAGTACTACGTGA |
| | | AAGAACTGAG |
| | | CAAGCCTGTGCATGGCAGCTGCAGGAACATCACCTGCGAC |
| | | AACTGGTTCA |
| | | CCAGCATCCCCCTGGCCAAGAACCTGCTGCAGGAACCCTA |
| | | CAAGCTGACC |
| | | ATCGTGGGCACCGTGCGGAGCAACAAGCGGGAGATCCCA |
| | | GAGGTGCTGAA |
| | | GAACAGCAGATCCAGACCTGTGGGAACAAGCATGTTCTGC |
| | | TTCGACGGCC |
| | | CCCTGACCCTGGTGTCCTACAAGCCCAAGCCCGCCAAGAT |
| | | GGTGTACCTG |
| | | CTGTCCAGCTGCGACGAGGACGCCAGCATCAACGAGAGC |
| | | ACCGGCAAGCC |
| | | CCAGATGGTGATGTACTACAACCAGACCAAGGGCGGCGTG |
| | | GACACCCTGG |
| | | ACCAGATGTGCAGCGTGATGACCTGCAGCAGAAAGACCA |
| | | ACAGATGGCCC |
| | | ATGGCCCTGCTGTACGGCATGATCAATATCGCCTGCATCA |
| | | ACAGCTTCAT |
| | | CATCTACAGCCACAACGTGTCCAGCAAGGGCGAGAAGGT |
| | | GCAGAGCCGGA |
| | | AGAAATTCATGCGGAACCTGTACATGAGCCTGACCTCCAG |
| | | CTTCATGAGA |
| | | AAGAGACTGGAAGCCCCCACCCTGAAGAGATACCTGCGG |
| | | GACAACATCAG |
| | | CAACATCCTGCCCAACGAAGTGCCAGGAACAAGCGACGA |
| | | CAGCACCGAGG |
| | | AACCCGTGATGAAGAAGAGGACCTACTGCACCTACTGTCC |
| | | CAGCAAGATC |
| | | AGAAGAAAGGCCAACGCCAGCTGCAAGAAATGCAAAAAA |
| | | GTGATCTGCCG |
| | | GGAGCACAACATCGACATGTGCCAGAGCTGTTTCTAGC |
| 17 | ILT (I147I I247L S533T) RNA | AUGGGCUCUAGCCUGGACGACGAGCACAUCCUGAGCGCC |
| | | CUGCUGCAG |
| | | AGCGACGACGAACUGGUGGGCGAGGACAGCGACAGCGAG |
| | | AUCAGCGACCA |
| | | CGUGUCCGAGGACGACGUGCAGUCCGACACCGAGGAAGC |
| | | CUUCAUCGACG |
| | | AGGUGCACGAAGUGCAGCCUACCAGCAGCGGCUCCGAGA |
| | | UCCUGGACGAG |
| | | CAGAACGUGAUCGAGCAGCCUGGCAGCUCCCUGGCCAGC |
| | | AACAGAAUCCU |

TABLE 2-continued

Nucleic acid sequences of wild type and mutated PIGGYBAC®
transposases

| SEQ ID NO: | ID | NUCLEIC ACID SEQUENCE |
|---|---|---|
| | | GACCCUGCCCCAGAGAACCAUCAGAGGCAAGAACAAGCA |
| | | CUGCUGGUCCA |
| | | CCUCCAAGAGCACCAGGCGGAGCAGAGUGUCCGCCCUGA |
| | | ACAUCGUGCGG |
| | | AGCCAGAGGGGCCCCACCAGAAUGUGCAGAAACAUCUAC |
| | | GACCCCCUGCU |
| | | GUGCUUCAAGCUGUUCUUCACCGACGAGAUCAUCAGCGA |
| | | GAUCGUGAAGU |
| | | GGACCAACGCCGAGAUCAGCCUGAAGAGGCGGGAGAGCA |
| | | UGACCGGCGCC |
| | | ACCUUCAGAGACACCAACGAGGACGAGAUCUACGCCUUC |
| | | UUCGGCAUCCU |
| | | GGUGAUGACCGCCGUGAGAAAGGACAACCACAUGAGCAC |
| | | CGACGACCUGU |
| | | UCGACAGAUCCCUGAGCAUGGUGUACGUGUCCGUGAUGA |
| | | GCAGAGACAGA |
| | | UUCGACUUCCUGAUCAGAUGCCUGAGAAUGGACGACAAG |
| | | AGCAUCAGACC |
| | | CACCCUGCGGGAGAACGACGUGUUCACCCCCGUGCGGAA |
| | | GCUGUGGGACC |
| | | UGUUCAUCCACCAGUGCAUCCAGAACUACACCCCUGGCG |
| | | CCCACCUGACC |
| | | AUCGAUGAGCAGCUGCUGGGCUUCAGAGGCAGAUGCCCC |
| | | UUCAGAAUGUA |
| | | CAUCCCCAACAAGCCCAGCAAGUACGGCAUCAAGAUCCU |
| | | GAUGAUGUGCG |
| | | ACAGCGGCACCAAGUACAUGAUCAACGGCAUGCCCUACC |
| | | UGGGCAGAGGC |
| | | ACCCAGACAAACGGCGUGCCCCUGGGCGAGUACUACGUG |
| | | AAAGAACUGAG |
| | | CAAGCCUGUGCAUGGCAGCUGCAGGAACAUCACCUGCGA |
| | | CAACUGGUUCA |
| | | CCAGCAUCCCCCUGGCCAAGAACCUGCUGCAGGAACCCU |
| | | ACAAGCUGACC |
| | | AUCGUGGGCACCGUGCGGAGCAACAAGCGGGAGAUCCCA |
| | | GAGGUGCUGAA |
| | | GAACAGCAGAUCCAGACCUGUGGGAACAAGCAUGUUCUG |
| | | CUUCGACGGCC |
| | | CCCUGACCCUGGUGUCCUACAAGCCCAAGCCCGCCAAGA |
| | | UGGUGUACCUG |
| | | CUGUCCAGCUGCGACGAGGACGCCAGCAUCAACGAGAGC |
| | | ACCGGCAAGCC |
| | | CCAGAUGGUGAUGUACUACAACCAGACCAAGGGCGGCGU |
| | | GGACACCCUGG |
| | | ACCAGAUGUGCAGCGUGAUGACCUGCAGCAGAAAGACCA |
| | | ACAGAUGGCCC |
| | | AUGGCCCUGCUGUACGGCAUGAUCAAUAUCGCCUGCAUC |
| | | AACAGCUUCAU |
| | | CAUCUACAGCCACAACGUGUCCAGCAAGGGCGAGAAGGU |
| | | GCAGAGCCGGA |
| | | AGAAAUUCAUGCGGAACCUGUACAUGAGCCUGACCUCCA |
| | | GCUUCAUGAGA |
| | | AAGAGACUGGAAGCCCCCACCCUGAAGAGAUACCUGCGG |
| | | GACAACAUCAC |
| | | CAACAUCCUGCCCAACGAAGUGCCAGGAACAAGCGACGA |
| | | CAGCACCGAGG |
| | | AACCCGUGAUGAAGAAGAGGACCUACUGCACCUACUGUC |
| | | CCAGCAAGAUC |
| | | AGAAGAAAGGCCAACGCCAGCUGCAAGAAAUGCAAAAA |
| | | AGUGAUCUGCCG |
| | | GGAGCACAACAUCGACAUGUGCCAGAGCUGUUUCUAGC |
| 18 | LLT (I147L I247L S533T) RNA | AUGGGCUCUAGCCUGGACGACGAGCACAUCCUGAGCGCC CUGCUGCAG |
| | | AGCGACGACGAACUGGUGGGCGAGGACAGCGACAGCGAG AUCAGCGACCA |
| | | CGUGUCCGAGGACGACGUGCAGUCCGACACCGAGGAAGC CUUCAUCGACG |
| | | AGGUGCACGAAGUGCAGCCUACCAGCAGCGGCUCCGAGA UCCUGGACGAG |
| | | CAGAACGUGAUCGAGCAGCCUGGCAGCUCCCUGGCCAGC AACAGAAUCCU |

TABLE 2-continued

Nucleic acid sequences of wild type and mutated PIGGYBAC®
transposases

| SEQ ID NO: | ID | NUCLEIC ACID SEQUENCE |
|---|---|---|
| | | GACCCUGCCCCAGAGAACCAUCAGAGGCAAGAACAAGCA |
| | | CUGCUGGUCCA |
| | | CCUCCAAGAGCACCAGGCGGAGCAGAGUGUCCGCCCUGA |
| | | ACAUCGUGCGG |
| | | AGCCAGAGGGGCCCCACCAGAAUGUGCAGAAACAUCUAC |
| | | GACCCCCUGCU |
| | | GUGCUUCAAGCUGUUCUUCACCGACGAGAUCAUCAGCGA |
| | | GCUGGUGAAGU |
| | | GGACCAACGCCGAGAUCAGCCUGAAGAGGCGGGAGAGCA |
| | | UGACCGGCGCC |
| | | ACCUUCAGAGACACCAACGAGGACGAGAUCUACGCCUUC |
| | | UUCGGCAUCCU |
| | | GGUGAUGACCGCCGUGAGAAAGGACAACCACAUGAGCAC |
| | | CGACGACCUGU |
| | | UCGACAGAUCCCUGAGCAUGGUGUACGUGUCCGUGAUGA |
| | | GCAGAGACAGA |
| | | UUCGACUUCCUGAUCAGAUGCCUGAGAAUGGACGACAAG |
| | | AGCAUCAGACC |
| | | CACCCUGCGGGAGAACGACGUGUUCACCCCCGUGCGGAA |
| | | GCUGUGGGACC |
| | | UGUUCAUCCACCAGUGCAUCCAGAACUACACCCCUGGCG |
| | | CCCACCUGACC |
| | | AUCGAUGAGCAGCUGCUGGGCUUCAGAGGCAGAUGCCCC |
| | | UUCAGAAUGUA |
| | | CAUCCCCAACAAGCCCAGCAAGUACGGCAUCAAGAUCCU |
| | | GAUGAUGUGCG |
| | | ACAGCGGCACCAAGUACAUGAUCAACGGCAUGCCCUACC |
| | | UGGGCAGAGGC |
| | | ACCCAGACAAACGGCGUGCCCCUGGGCGAGUACUACGUG |
| | | AAAGAACUGAG |
| | | CAAGCCUGUGCAUGGCAGCUGCAGGAACAUCACCUGCGA |
| | | CAACUGGUUCA |
| | | CCAGCAUCCCCCUGGCCAAGAACCUGCUGCAGGAACCCU |
| | | ACAAGCUGACC |
| | | AUCGUGGGCACCGUGCGGAGCAACAAGCGGGAGAUCCCA |
| | | GAGGUGCUGAA |
| | | GAACAGCAGAUCCAGACCUGUGGGAACAAGCAUGUUCUG |
| | | CUUCGACGGCC |
| | | CCCUGACCCUGGUGUCCUACAAGCCCAAGCCCGCCAAGA |
| | | UGGUGUACCUG |
| | | CUGUCCAGCUGCGACGAGGACGCCAGCAUCAACGAGAGC |
| | | ACCGGCAAGCC |
| | | CCAGAUGGUGAUGUACUACAACCAGACCAAGGGCGGCGU |
| | | GGACACCCUGG |
| | | ACCAGAUGUGCAGCGUGAUGACCUGCAGCAGAAAGACCA |
| | | ACAGAUGGCCC |
| | | AUGGCCCUGCUGUACGGCAUGAUCAAUAUCGCCUGCAUC |
| | | AACAGCUUCAU |
| | | CAUCUACAGCCACAACGUGUCCAGCAAGGGCGAGAAGGU |
| | | GCAGAGCCGGA |
| | | AGAAAUUCAUGCGGAACCUGUACAUGAGCCUGACCUCCA |
| | | GCUUCAUGAGA |
| | | AAGAGACUGGAAGCCCCCACCCUGAAGAGAUACCUGCGG |
| | | GACAACAUCAC |
| | | CAACAUCCUGCCCAACGAAGUGCCAGGAACAAGCGACGA |
| | | CAGCACCGAGG |
| | | AACCCGUGAUGAAGAAGAGGACCUACUGCACCUACUGUC |
| | | CCAGCAAGAUC |
| | | AGAAGAAAGGCCAACGCCAGCUGCAAGAAAUGCAAAAA |
| | | AGUGAUCUGCCG |
| | | GGAGCACAACAUCGACAUGUGCCAGAGCUGUUUCUAGC |

Polypeptides and proteins of interest can be of scientific or commercial interest, including protein-based therapeutics. Proteins of interest include, among other things, secreted proteins, non-secreted proteins, intracellular proteins or membrane-bound proteins. Polypeptides and proteins of interest can be produced by recombinant animal cell lines using cell culture methods and may be referred to as "recombinant proteins". The expressed protein(s) may be produced intracellularly or secreted into the culture medium from which it can be recovered and/or collected. The term "isolated protein" or "isolated recombinant protein" refers to a polypeptide or protein of interest, that is purified away from proteins or polypeptides or other contaminants that would interfere with its therapeutic, diagnostic, prophylactic, research or other use. Proteins of interest include proteins that exert a therapeutic effect by binding a target, particularly a target among those listed below, including targets derived therefrom, targets related thereto, and modifications thereof.

Proteins of interest include "antigen-binding proteins". Antigen-binding protein refers to proteins or polypeptides that comprise an antigen-binding region or antigen-binding portion that has affinity for another molecule to which it binds (antigen). Antigen-binding proteins encompass antibodies, peptibodies, antibody fragments, antibody derivatives, antibody analogs, fusion proteins (including single-chain variable fragments (scFvs) and double-chain (divalent) scFvs, muteins, and Xmabs. Also included are bispecific T cell engagers (BiTE®), bispecific T cell engagers having extensions, such as half life extensions, for example HLE BiTEs, Heterog BITE and others, chimeric antigen receptors (CARs, CAR Ts), and T cell receptors (TCRs).

An scFv is a single chain antibody fragment having the variable regions of the heavy and light chains of an antibody linked together. See U.S. Pat. Nos. 7,741,465, and 6,319,494 as well as Eshhar et al., Cancer Immunol Immunotherapy (1997) 45:131-136. An scFv retains the parent antibody's ability to specifically interact with target antigen.

The term "antibody" includes reference to both glycosylated and non-glycosylated immunoglobulins of any isotype or subclass or to an antigen-binding region thereof that competes with the intact antibody for specific binding. Unless otherwise specified, antibodies include human, humanized, chimeric, multi-specific, monoclonal, polyclonal, heteroIgG, bispecific, and oligomers or antigen binding fragments thereof. Antibodies include the IgG1-, IgG2- IgG3- or IgG4-type. Also included are proteins having an antigen binding fragment or region such as Fab, Fab', F(ab')2, Fv, diabodies, Fd, dAb, maxibodies, single chain antibody molecules, single domain $V_H H$, complementarity determining region (CDR) fragments, scFv, diabodies, triabodies, tetrabodies and polypeptides that contain at least a portion of an immunoglobulin that is sufficient to confer specific antigen binding to a target polypeptide.

Also included are human, humanized, and other antigen-binding proteins, such as human and humanized antibodies, that do not engender significantly deleterious immune responses when administered to a human.

Also included are modified proteins, such as are proteins modified chemically by a non-covalent bond, covalent bond, or both a covalent and non-covalent bond. Also included are proteins further comprising one or more post-translational modifications which may be made by cellular modification systems or modifications introduced ex vivo by enzymatic and/or chemical methods or introduced in other ways.

Proteins of interest may also include recombinant fusion proteins comprising, for example, a multimerization domain, such as a leucine zipper, a coiled coil, an Fc portion of an immunoglobulin, and the like. Also included are proteins comprising all or part of the amino acid sequences of differentiation antigens (referred to as CD proteins) or their ligands or proteins substantially similar to either of these.

In some embodiments, proteins of interest may include colony stimulating factors, such as granulocyte colony-stimulating factor (G-CSF). Such G-CSF agents include, but are not limited to, Neupogen® (filgrastim) and Neulasta® (pegfilgrastim). Also included are erythropoiesis stimulating agents (ESA), such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoctin alfa, epoetin beta, epoetin zeta, epoetin theta, and epoetin delta, epoetin omega, epoctin iota, tissue plasminogen activator, GLP-1 receptor agonists, as well as the molecules or variants or analogs thereof and biosimilars of any of the foregoing.

In some embodiments, proteins of interest may include proteins that bind specifically to one or more CD proteins, HER receptor family proteins, cell adhesion molecules, growth factors, nerve growth factors, fibroblast growth factors, transforming growth factors (TGF), insulin-like growth factors, osteoinductive factors, insulin and insulin-related proteins, coagulation and coagulation-related proteins, colony stimulating factors (CSFs), other blood and serum proteins blood group antigens: receptors, receptor-associated proteins, growth hormones, growth hormone receptors, T-cell receptors: neurotrophic factors, neurotrophins, relaxins, interferons, interleukins, viral antigens, lipoproteins, integrins, rheumatoid factors, immunotoxins, surface membrane proteins, transport proteins, homing receptors, addressins, regulatory proteins, and immunoadhesins.

In some embodiments proteins of interest bind to one of more of the following, alone or in any combination: CD proteins including but not limited to CD3, CD4, CD5, CD7, CD8, CD19, CD20, CD22, CD25, CD30, CD33, CD34, CD38, CD40, CD70, CD123, CD133, CD138, CD171, and CD174, HER receptor family proteins, including, for instance, HER2, HER3, HER4, and the EGF receptor, EGFRVIII, cell adhesion molecules, for example, LFA-1, Mol, p150,95, VLA-4, ICAM-1, VCAM, and alpha v/beta 3 integrin, growth factors, including but not limited to, for example, vascular endothelial growth factor ("VEGF"); VEGFR2, growth hormone, thyroid stimulating hormone, follicle stimulating hormone, luteinizing hormone, growth hormone releasing factor, parathyroid hormone, mullerian-inhibiting substance, human macrophage inflammatory protein (MIP-1-alpha), erythropoietin (EPO), nerve growth factor, such as NGF-beta, platelet-derived growth factor (PDGF), fibroblast growth factors, including, for instance, aFGF and bFGF, epidermal growth factor (EGF), Cripto, transforming growth factors (TGF), including, among others, TGF-α and TGF-β, including TGF-β1, TGF-β2, TGF-β3, TGF-β4, or TGF-β5, insulin-like growth factors-I and -II (IGF-I and IGF-II), des (1-3)-IGF-I (brain IGF-I), and osteoinductive factors, insulins and insulin-related proteins, including but not limited to insulin, insulin A-chain, insulin B-chain, proinsulin, and insulin-like growth factor binding proteins: (coagulation and coagulation-related proteins, such as, among others, factor VIII, tissue factor, von Willebrand factor, protein C, alpha-1-antitrypsin, plasminogen activators, such as urokinase and tissue plasminogen activator ("t-PA"), bombazine, thrombin, thrombopoietin, and thrombopoietin receptor, colony stimulating factors (CSFs), including the following, among others, M-CSF, GM-CSF, and G-CSF, other blood and serum proteins, including but not limited to albumin, IgE, and blood group antigens, receptors and receptor-associated proteins, including, for example, flk2/flt3 receptor, obesity (OB) receptor, growth hormone receptors, and T-cell receptors: neurotrophic factors, including but not limited to, bone-derived neurotrophic factor (BDNF) and neurotrophin-3, -4, -5, or -6 (NT-3, NT-4, NT-5, or NT-6); relaxin A-chain, relaxin B-chain, and prorelaxin, interferons, including for example, interferon-alpha, -beta, and -gamma, interleukins (ILs), e.g., IL-1 to IL-10, IL-12, IL-15, IL-17, IL-23, IL-12/IL-23, IL-2Ra, IL1-R1, IL-6 receptor, IL-4 receptor and/or IL-13 to the receptor, IL-13RA2, or IL-17 receptor, IL-IRAP,: viral antigens, including but not limited to, an AIDS envelope viral antigen, lipoproteins, calcitonin, glucagon, atrial natriuretic factor, lung surfactant, tumor necrosis factor-alpha and -beta, enkephalinase, BCMA, IgKappa, ROR-1, ERBB2, mesothelin, RANTES (regulated on activation normally T-cell expressed and secreted), mouse gonadotropin-associated peptide, Dnase, FR-alpha, inhibin, and activin, integrin, protein A or D, rheumatoid factors, immunotoxins, bone morphogenetic protein (BMP), superoxide dismutase, surface membrane proteins, decay accelerating factor (DAF), AIDS envelope, transport proteins, homing receptors, MIC (MIC-a, MIC-B), ULBP 1-6, EPCAM, addressins, regulatory proteins, immunoadhesins, antigen-binding proteins, somatropin, CTGF, CTLA4, cotaxin-1, MUC1, CEA, c-MET, Claudin-18, GPC-3, EPHA2, FPA, LMP1, MG7, NY-ESO-1, PSCA, ganglioside GD2, glanglioside GM2, BAFF, OPGL (RANKL), myostatin, Dickkopf-1 (DKK-1), Ang2, NGF, IGF-1 receptor, hepatocyte growth factor (HGF), TRAIL-R2, c-Kit, B7RP-1, PSMA, NKG2D-1, programmed cell death protein 1 and ligand, PD1 and PDL1, mannose receptor/hCGB, hepatitis-C virus, mesothelin dsFv [PE38 conjugate, *Legionella pneumophila* (lly), IFN gamma, interferon gamma induced protein 10 (IP10), IFNAR, TALL-1, thymic stromal lymphopoietin (TSLP), proprotein convertase subtilisin/Kexin Type 9 (PCSK9), stem cell factors, Flt-3, calcitonin gene-related peptide (CGRP), OX40L, α4β7, platelet specific (platelet glycoprotein Iib/IIIb (PAC-1), transforming growth factor beta (TFGβ), Zona pellucida sperm-binding protein 3 (ZP-3), TWEAK, platelet derived growth factor receptor alpha (PDGFRα), sclerostin, and biologically active fragments or variants of any of the foregoing.

In another embodiment, proteins of interest include abciximab, adalimumab, adecatumumab, aflibercept, alemtuzumab, alirocumab, anakinra, atacicept, basiliximab, belimumab, bevacizumab, biosozumab, blinatumomab, brentuximab vedotin, brodalumab, cantuzumab mertansine, canakinumab, cetuximab, certolizumab pegol, conatumumab, daclizumab, denosumab, eculizumab, edrecolomab, efalizumab, epratuzumab, etanercept, evolocumab, galiximab, ganitumab, gemtuzumab, golimumab, ibritumomab tiuxetan, infliximab, ipilimumab, lerdelimumab, lumiliximab, lxdkizumab, mapatumumab, motesanib diphosphate, muromonab-CD3, natalizumab, nesiritide, nimotuzumab, nivolumab, ocrelizumab, ofatumumab, omalizumab, oprelvekin, palivizumab, panitumumab, pembrolizumab, pertuzumab, pexelizumab, ranibizumab, rilotumumab, rituximab, romiplostim, romosozumab, sargamostim, tocilizumab, tositumomab, trastuzumab, ustekinumab, vedolizumab, visilizumab, volociximab, zanolimumab, zalutumumab, and biosimilars of any of the foregoing.

Proteins of interest according to the invention encompass all of the foregoing and further include antibodies comprising 1, 2, 3, 4, 5, or 6 of the complementarity determining regions (CDRs) of any of the aforementioned antibodies. Also included are variants that comprise a region that is 70% or more, especially 80% or more, more especially 90% or more, yet more especially 95% or more, particularly 97% or more, more particularly 98% or more, yet more particularly 99% or more identical in amino acid sequence to a reference amino acid sequence of a protein of interest. Identity in this regard can be determined using a variety of well-known and readily available amino acid sequence analysis software. Preferred software includes those that implement the Smith- Waterman algorithms, considered a satisfactory solution to the problem of searching and aligning sequences. Other algorithms also may be employed, particularly where speed is an important consideration. Commonly employed programs for alignment and homology matching of DNAs, RNAs, and polypeptides that can be used in this regard include FASTA, TFASTA, BLASTN, BLASTP, BLASTX, TBLASTN, PROSRCH, BLAZE, and MPSRCH, the latter being an implementation of the Smith-Waterman algorithm for execution on massively parallel processors made by MasPar.

Proteins of interest can also include genetically engineered receptors such as chimeric antigen receptors (CARs or CAR-Ts) and T cell receptors (TCRs), as well as other proteins comprising an antigen binding molecule that interacts with that targeted antigen. CARs can be engineered to bind to an antigen (such as a cell-surface antigen) by incorporating an antigen binding molecule that interacts with that targeted antigen. CARs typically incorporate an antigen binding domain (such as scFv) in tandem with one or more costimulatory ("signaling") domains and one or more activating domains.

Preferably, the antigen binding molecule is an antibody fragment thereof, and more preferably one or more single chain antibody fragment ("scFv"). scFvs are preferred for use in chimeric antigen receptors because they can be engineered to be expressed as part of a single chain along with the other CAR components. See Krause et al., J. Exp. Med., 188(4): 619-626, 1998: Finney et al., Journal of Immunology, 161:2791-2797, 1998.

Chimeric antigen receptors incorporate one or more costimulatory (signaling) domains to increase their potency. See U.S. Pat. Nos. 7,741,465, and 6,319,494, as well as Krause et al. and Finney et al. (supra), Song et al., Blood 119:696-706 (2012); Kalos et al., Sci Transl. Med. 3:95 (2011); Porter et al., N. Engl. J. Med. 365:725-33 (2011), and Gross et al., Annu. Rev. Pharmacol. Toxicol. 56:59-83 (2016). Suitable costimulatory domains can be derived from, among other sources, CD28, CD28T, OX40, 4-1BB/CD137, CD2, CD3 (alpha, beta, delta, epsilon, gamma, zeta), CD4, CD5, CD7, CD8, CD9, CD16, CD22, CD27, CD30, CD 33, CD37, CD40, CD 45, CD64, CD80, CD86, CD134, CD137, CD154, PD-1, ICOS, lymphocyte function-associated antigen-1 (LFA-1 (CDI la/CD18), CD247, CD276 (B7-H3), LIGHT (tumor necrosis factor superfamily member 14: TNFSF14), NKG2C, Ig alpha (CD79a), DAP-10, Fc gamma receptor, MHC class I molecule, TNF, TNFr, integrin, signaling lymphocytic activation molecule, BTLA, Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLAI, CD49a, ITGA4, IA4, CD49D, ITGA6, VLA-6, CD49f, ITGAD, CDI-Id, ITGAE, CD103, ITGAL, CDI-la, LFA-1, ITGAM, CDI-lb, ITGAX, CDI-Ic, ITGBI, CD29, ITGB2, CD18, LFA-1, ITGB7, NKG2D, TNFR2, TRANCE/RANKL, DNAMI (CD226), SLAMF4 (CD244, 2B4), CD84, CD96 (Tactile), CEACAMI, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, 41-BB, GADS, SLP-76, PAG/Cbp, CD19a, CD83 ligand, or fragments or combinations thereof. The costimulatory domain can comprise one or more of an extracellular portions, a transmembrane portion, and an intracellular portion.

CARs also include one or more activating domains. CD3 zeta is an element of the T cell receptor on native T cells and has been shown to be an important intracellular activating element in CARs.

CARs are transmembrane proteins, comprising an extracellular domain, typically containing an antigen binding protein that it is capable of recognizing and binding to the antigen of interest, and also including a "hinge" region. In addition is a transmembrane domain and an intracellular (cytoplasmic) domain.

The extracellular domain is beneficial for signaling and for an efficient response of lymphocytes to an antigen. from any protein described herein or any combination thereof. The extracellular domain may be derived either from a synthetic or from a natural source, such as the proteins described herein. The extracellular domains often comprise a hinge portion. This is a portion of the extracellular domain, sometimes referred to as a "spacer" region. Hinges may be derived from the proteins as described herein, particularly the costimulatory proteins described above, as well as immunoglobulin (Ig) sequences or other suitable molecules to achieve the desired special distance from the target cell.

A transmembrane domain may be fused to the extracellular domain of the CAR. It can similarly be fused to the intracellular domain of the CAR. The transmembrane domain may be derived either from a synthetic or from a natural source, such as the proteins described herein, particularly the costimulatory proteins described above.

An intracellular (cytoplasmic) domain may be fused to the transmembrane domain and can provide activation of at least one of the normal effector functions of the immune cell. Effector function of a T cell, for example, may be cytolytic activity or helper activity including the secretion of cytokines. Intracellular domains can be derived from the proteins described herein, particularly from CD3.

A variety of known techniques can be utilized in making the polynucleotides, polypeptides, vectors, host cells, immune cells, compositions, and the like according to the invention.

Expression systems and constructs in the form of plasmids, expression vectors, transcription or expression cassettes that comprise at least one nucleic acid molecule as described above are also provided herein, as well host cells comprising such expression systems or constructs. As used herein, "vector" means any molecule or entity (e.g., nucleic acid, plasmid, bacteriophage, transposon, cosmid, chromosome, virus, virus capsid, virion, naked DNA, complexed DNA and the like) suitable for use to transfer and/or transport protein encoding information into a host cell and/or to a specific location and/or compartment within a host cell. Vectors can include viral and non-viral vectors, non-episomal mammalian vectors. Vectors are often referred to as expression vectors, for example, recombinant expression vectors and cloning vectors. The vector may be introduced into a host cell to allow replication of the vector itself and thereby amplify the copies of the polynucleotide contained therein. The cloning vectors may contain sequence components generally include, without limitation, an origin of replication, promoter sequences, transcription initiation sequences, enhancer sequences, and selectable markers. These elements may be selected as appropriate by a person of ordinary skill in the art.

Vectors are useful for transformation of a host cell and contain nucleic acid sequences that direct and/or control (in conjunction with the host cell) expression of one or more heterologous coding regions operatively linked thereto. An expression construct may include, but is not limited to, sequences that affect or control transcription, translation, and, if introns are present, affect RNA splicing of a coding region operably linked thereto. "Operably linked" means that the components to which the term is applied are in a relationship that allows them to carry out their inherent functions. For example, a control sequence, e.g., a promoter, in a vector that is "operably linked" to a protein coding sequence are arranged such that normal activity of the control sequence leads to transcription of the protein coding sequence resulting in recombinant expression of the encoded protein.

Vectors may be selected to be functional in the particular host cell employed (i.e., the vector is compatible with the host cell machinery, permitting amplification and/or expression of the gene can occur). In some embodiments, vectors are used that employ protein-fragment complementation assays using protein reporters, such as dihydrofolate reductase (see, for example, U.S. Pat. No. 6,270,964). Suitable expression vectors are known in the art and are also commercially available.

Typically, vectors used in any of the host cells will contain sequences for plasmid maintenance and for cloning and expression of exogenous nucleotide sequences. Such sequences will typically include one or more of the following nucleotide sequences: a promoter, one or more enhancer sequences, an origin of replication, transcriptional and translational control sequences, a transcriptional termination sequence, a complete intron sequence containing a donor and acceptor splice site, various pre- or pro-sequences to improve glycosylation or yield, a native or heterologous signal sequence (leader sequence or signal peptide) for polypeptide secretion, a ribosome binding site, a polyadenylation sequence, internal ribosome entry site (IRES) sequences, an expression augmenting sequence element (EASE), tripartite leader (TPA) and VA gene RNAs from Adenovirus 2, a polylinker region for inserting the polynucleotide encoding the polypeptide to be expressed, and a selectable marker element. Vectors may be constructed from a starting vector such as a commercially available vector, additional elements may be individually obtained and ligated into the vector. Methods used for obtaining each of the components are well known to one skilled in the art.

Vector components may be homologous (i.e., from the same species and/or strain as the host cell), heterologous (i.e., from a species other than the host cell species or strain), hybrid (i.e., a combination of flanking sequences from more than one source), synthetic or native. The sequences of components useful in the vectors may be obtained by methods well known in the art, such as those previously identified by mapping and/or by restriction endonuclease. In addition, they can be obtained by polymerase chain reaction (PCR) and/or by screening a genomic library with suitable probes.

A ribosome-binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed.

An origin of replication aids in the amplification of the vector in a host cell. They may be included as part of commercially available prokaryotic vectors and may also be chemically synthesized based on a known sequence and ligated into the vector. Various viral origins (e.g., SV40, polyoma, adenovirus, vesicular stomatitus virus (VSV), or papillomaviruses such as HPV or BPV) are useful for cloning vectors in mammalian cells.

Transcriptional and translational control sequences for mammalian host cell expression vectors can be excised from viral genomes. Commonly used promoter and enhancer sequences are derived from polyoma virus, adenovirus 2, simian virus 40 (SV40), and human cytomegalovirus (CMV). For example, the human CMV promoter/enhancer of immediate early gene 1 may be used. See e.g. Patterson et al. (1994), Applied Microbiol. Biotechnol. 40:691-98. DNA sequences derived from the SV40 viral genome, for example, SV40 origin, early and late promoter, enhancer, splice, and polyadenylation sites can be used to provide other genetic elements for expression of a structural gene sequence in a mammalian host cell. Viral early and late promoters are particularly useful because both are easily obtained from a viral genome as a fragment, which can also contain a viral origin of replication (Fiers et al. (1978), Nature 273:113: Kaufman (1990), Meth. in Enzymol. 185: 487-511). Smaller or larger SV40 fragments can also be used, provided the approximately 250 bp sequence extending from the Hind III site toward the Bgl I site located in the SV40 viral origin of replication site is included.

A transcription termination sequence is typically located 3' to the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis known to those of skill in the art.

A selectable marker gene encoding a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells: (b) complement auxotrophic deficiencies of the cell: or (c) supply critical nutrients not available from complex or defined media. Specific selectable markers are the kanamycin resistance gene, the ampicillin resistance gene, and the tetracycline resistance gene. Advantageously, a neomycin resistance gene may also be used for selection in both prokaryotic and eukaryotic host cells.

Other selectable genes may be used to amplify the gene that will be expressed. Amplification is the process wherein genes that are required for production of a protein critical for growth or cell survival are reiterated in tandem within the chromosomes of successive generations of recombinant cells. Examples of suitable selectable markers for mammalian cells include glutamine synthase (GS)/methionine sulfoximine (MSX) system, dihydrofolate reductase (DHFR), and promoterless thymidine kinase genes. Mammalian cell transformants are placed under selection pressure wherein only the transformants are uniquely adapted to survive by virtue of the selectable gene present in the vector. Selection pressure is imposed by culturing the transformed cells under conditions in which the concentration of selection agent in the medium is successively increased, thereby leading to the amplification of both the selectable gene and the DNA that encodes a protein of interest. As a result, increased quantities of a polypeptide of interest are synthesized from the amplified DNA.

In some cases, such as where glycosylation is desired in a eukaryotic host cell expression system, one may manipulate the various pre- or pro-sequences to improve glycosylation or yield. For example, one may alter the peptidase cleavage site of a particular signal peptide, or add prosequences, which also may affect glycosylation. The final protein product may have, in the −1 position (relative to the first amino acid of the mature protein), one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired polypeptide if the enzyme cuts at such area within the mature polypeptide.

Expression and cloning will typically contain a promoter that is recognized by the host organism and operably linked to the molecule encoding a protein of interest. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, uniformly transcribe a gene to which they are operably linked, that is, with little or no control over gene expression. A large number of promoters, recognized by a variety of potential host cells, are well known.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus, and Simian Virus 40 (SV40). Other suitable mammalian promoters include heterologous mammalian promoters, for example, heat-shock promoters and the actin promoter.

Additional promoters which may be of interest include, but are not limited to: SV40 early promoter (Benoist and Chambon, 1981, Nature 290:304-310); CMV promoter (Thornsen et al., 1984, Proc. Natl. Acad. U.S.A. 81:659-663); the promoter contained in the 3' long terminal repeat of Rous sarcoma virus (Yamamoto et al., 1980, Cell 22:787-797); herpes thymidine kinase promoter (Wagner et al., 1981, Proc. Natl. Acad. Sci. U.S.A. 78:1444-1445); glyceraldehyde-3-phosphate dehydrogenase (GAPDH); promoter and regulatory sequences from the metallothionine gene (Prinster et al., 1982, Nature 296:39-42); and prokaryotic promoters such as the beta-lactamase promoter (Villa-Kamaroff et al., 1978, Proc. Natl. Acad. Sci. U.S.A. 75:3727-3731); or the tac promoter (DeBoer et al., 1983, Proc. Natl. Acad. Sci. U.S.A. 80:21-25). Also of interest are the following animal transcriptional control regions, which exhibit tissue specificity and have been utilized in transgenic animals: the elastase I gene control region that is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); the insulin gene control region that is active in pancreatic beta cells (Hanahan, 1985, Nature 315:115-122); the immunoglobulin gene control region that is active in lymphoid cells (Grosschedl et al., 1984, Cell 38:647-658; Adames et al., 1985, Nature 318:533-538: Alexander et al., 1987, Mol. Cell. Biol. 7:1436-1444); the mouse mammary tumor virus control region that is active in testicular, breast, lymphoid and mast cells (Leder et al., 1986, Cell 45:485-495); the albumin gene control region that is active in liver (Pinkert et al., 1987, Genes and Devel. 1:268-276); the alpha-fetoprotein gene control region that is active in liver (Krumlauf et al., 1985, Mol. Cell. Biol. 5:1639-1648; Hammer et al., 1987, Science 253:53-58); the alpha 1-antitrypsin gene control region that is active in liver (Kelsey et al., 1987, Genes and Devel. 1:161-171); the beta-globin gene control region that is active in myeloid cells (Mogram et al., 1985, Nature 315:338-340; Kollias et al., 1986, Cell 46:89-94); the myelin basic protein gene control region that is active in oligodendrocyte cells in the brain (Readhead et al., 1987, Cell 48:703-712); the myosin light chain-2 gene control region that is active in skeletal muscle (Sani, 1985, Nature 314:283-286); and the gonadotropic releasing hormone gene control region that is active in the hypothalamus (Mason et al., 1986, Science 234:1372-1378).

An enhancer sequence may be inserted into the vector to increase transcription by higher eukaryotes. Enhancers are cis-acting elements of DNA, usually about 10-300 bp in length, that act on the promoter to increase transcription. Enhancers are relatively orientation and position independent, having been found at positions both 5' and 3' to the transcription unit. Several enhancer sequences available from mammalian genes are known (e.g., globin, elastase, albumin, alpha-feto-protein and insulin). Typically, however, an enhancer from a virus is used. The SV40 enhancer, the cytomegalovirus early promoter enhancer, the polyoma enhancer, and adenovirus enhancers known in the art are exemplary enhancing elements for the activation of eukaryotic promoters. While an enhancer may be positioned in the vector either 5' or 3' to a coding sequence, it is typically located at a site 5' from the promoter.

A sequence encoding an appropriate native or heterologous signal sequence (leader sequence or signal peptide) can be incorporated into an expression vector, to promote extracellular secretion of the protein of interest. The choice of signal peptide or leader depends on the type of host cells in which the protein of interest to be produced, and a heterologous signal sequence can replace the native signal sequence. Examples of signal peptides that are functional in mammalian host cells include the following: the signal sequence for interleukin-7 described in U.S. Pat. No. 4,965, 195: the signal sequence for interleukin-2 receptor described in Cosman et al., 1984, Nature 312:768; the interleukin-4 receptor signal peptide described in EP Patent No. 0367 566: the type I interleukin-1 receptor signal peptide described in U.S. Pat. No. 4,968,607: the type II interleukin-1 receptor signal peptide described in EP Patent No. 0 460 846.

Additional control sequences shown to improve expression of heterologous genes from mammalian expression vectors include such elements as the expression augmenting sequence element (EASE) derived from CHO cells (Morris et al., in Animal Cell Technology, pp. 529-534 (1997); U.S. Pat. Nos. 6,312,951 B1, 6,027,915, and 6,309,841 B1) and the tripartite leader (TPL) and VA gene RNAs from Adenovirus 2 (Gingeras et al. (1982), J. Biol. Chem. 257:13475-13491). The internal ribosome entry site (IRES) sequences of viral origin allows dicistronic mRNAs to be translated efficiently (Oh and Sarnow (1993), Current Opinion in Genetics and Development 3:295-300; Ramesh et al. (1996), Nucleic Acids Research 24:2697-2700).

In one embodiment, the invention provides a vector comprising a nucleic acid molecule encoding a PIGGY-BAC® transposase as described herein. In one embodiment the vector further comprises a PIGGYBAC® transposon comprising an insertion site for at least one exogenous nucleic acid molecule sequence encoding at least one protein of interest. In one embodiment, multiple proteins of interest are expressed by the exogeneous nucleic molecule(s). In one embodiment the vector includes bi-cistronic or multi-cistronic constructs that encode multiple proteins of interest. In one embodiment, the transposon comprises at least the 5' and 3' inverted repeat elements of a PIGGYBAC® transposon. In one embodiment is provides an engineered nucleic acid molecule encoding a PIGGYBAC® transposase as described herein. In one embodiment is provided a PIGGY-BAC® transposase encoded by the nucleic acid sequence of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, or SEQ ID NO: 18. In another aspect the invention provides a PIGGYBAC® transposase encoded by the nucleic acid sequence of SEQ ID NO: 3, SEQ ID NO: 5, or SEQ ID NO: 7. In another aspect the invention provides a PIGGYBAC® transposase encoded by the nucleic acid sequence of SEQ ID NO: 11, SEQ ID NO: 13, or SEQ ID NO: 15. In another aspect the invention provides a PIGGY-BAC® transposase encoded by the nucleic acid sequence of SEQ ID NO: 9, or SEQ ID NO: 11. In another aspect the invention provides a PIGGYBAC® transposase encoded by the nucleic acid sequence of SEQ ID NO: 17, or SEQ ID NO:18. In another aspect the invention provides a PIGGY-BAC® transposase encoded by the nucleic acid sequence of SEQ ID NO: 3. In another aspect the invention provides a PIGGYBAC® transposase encoded by the nucleic acid sequence of SEQ ID NO: 5. In another aspect the invention provides a PIGGYBAC® transposase encoded by the nucleic acid sequence of SEQ ID NO: 7. In another aspect the invention provides a PIGGYBAC® transposase encoded by the nucleic acid sequence of SEQ ID NO: 9. In another aspect the invention provides a PIGGYBAC® transposase encoded by the nucleic acid sequence of SEQ ID NO: 11. In another aspect the invention provides a PIGGYBAC® transposase encoded by the nucleic acid sequence of SEQ ID NO: 13. In another aspect the invention provides a PIGGYBAC® transposase encoded by the nucleic acid sequence of SEQ ID NO: 15. In another aspect the invention provides a PIGGY-BAC® transposase encoded by the nucleic acid sequence of SEQ ID NO: 17. In another aspect the invention provides a PIGGYBAC® transposase encoded by the nucleic acid sequence of SEQ ID NO:18.

In one embodiment is provided a PIGGYBAC® transposase comprising an amino acid substitution at one or more of the positions 147, 176, 221, 247, 429, 533, and 573 of SEQ ID NO: 2. In a related embodiment the PIGGYBAC® transposase comprises an amino acid substitution of leucine for the isoleucine at one or more of the positions 147, 176, 221, and 247 of SEQ ID NO:2. In a related embodiment the PIGGYBAC® transposase comprises an amino acid substitution of threonine for serine at one or more of the positions 429, 533, and 573 of SEQ ID NO:2. In a related embodiment the PIGGYBAC® transposase comprises an amino acid substitution of leucine for the isoleucine at one or more of the positions 147, 176, 221, and 247 and/or an amino acid substitution of threonine for serine at one or more of the positions 429, 533, and 573 of SEQ ID NO:2. In a related embodiment the PIGGYBAC® transposase comprises at least one of the following amino acid substitutions, a leucine for the isoleucine at position 147 of SEQ ID NO:2, a leucine for the isoleucine at position 247 of SEQ ID NO:2, and a threonine for the serine at position 533 of SEQ ID NO:2. In a related embodiment the PIGGYBAC® transposase comprises at least two of the following amino acid substitutions, a leucine for the isoleucine at position 147 of SEQ ID NO:2, a leucine for the isoleucine at position 247 of SEQ ID NO:2, and a threonine for the serine at position 533 of SEQ ID NO:2. In another related embodiment the PIGGYBAC® transposase comprises a leucine for isoleucine substitution at position 147 of SEQ ID NO:2, a leucine for isoleucine substitution at position 247 of SEQ ID NO:2, and a threonine for serine substitution at position 533 of SEQ ID NO: 2. In one embodiment is provided a PIGGYBAC® transposase having the amino acid sequence of SEQ ID NO: 4, SEQ ID NO: 6, SEQ ID NO: 8, SEQ ID NO: 10, SEQ ID NO: 12, SEQ ID NO: 14, or SEQ ID NO: 16. In another aspect the invention provides a PIGGYBAC® transposase having the amino acid sequence of SEQ ID NO: 4, SEQ ID NO: 6, or SEQ ID NO: 8. In another aspect the invention provides a PIGGYBAC® transposase having the amino acid sequence of SEQ ID NO: 12, SEQ ID NO: 14, or SEQ ID NO: 16. In another aspect the invention provides a PIGGY-BAC® transposase having the amino acid sequence of SEQ ID NO: 10 or 12. In another aspect the invention provides a PIGGYBAC® transposase having the amino acid sequence of SEQ ID NO:4. In another aspect the invention provides a PIGGYBAC® transposase having the amino acid sequence of SEQ ID NO:6. In another aspect the invention provides a PIGGYBAC® transposase having the amino acid sequence of SEQ ID NO:8. In another aspect the invention provides a PIGGYBAC® transposase having the amino acid sequence of SEQ ID NO:10. In another aspect the invention provides a PIGGYBAC® transposase having the amino acid sequence of SEQ ID NO: 12. In another aspect the invention provides a PIGGYBAC® transposase having the amino acid sequence of SEQ ID NO: 14. In another aspect the invention provides a PIGGYBAC® transposase having the amino acid sequence of SEQ ID NO: 16.

In one embodiment, a single vector comprising a PIG-GYBAC® transposase as described herein and transposon comprising an insertion site for at least one exogenous nucleic acid sequence encoding at least one protein of interest may transfected into a cell. In one embodiment, the invention provides a nucleic acid molecule encoding a PIGGYBAC® transposase as described herein further comprising at least one nucleic acid molecule encoding at least one protein of interest flanked by at least 5' and 3' invented repeat elements of a PIGGYBAC® transposon. In one embodiment, multiple proteins of interest are expressed by the exogeneous nucleic molecule(s). In one embodiment the vector includes bi-cistronic or multi-cistronic constructs that encode multiple proteins of interest.

In another embodiment, the invention provides a vector comprising an engineered nucleic acid molecule encoding a PIGGYBAC® transposase as described herein and a second vector comprising the PIGGYBAC® transposon comprising an insertion site for one or more exogenous nucleic acid molecules encoding at least one protein of interest, wherein the two vectors may be co-transfected into a cell. In a related embodiment, the transposon comprises at least the 5' and 3' inverted repeat elements of a PIGGYBAC® transposon. In one embodiment, multiple proteins of interest are expressed by the exogeneous nucleic molecule(s). In one embodiment the vector includes bi-cistronic or multi-cistronic constructs that encode multiple proteins of interest.

Following construction, one or more vectors may be inserted into a suitable cell for amplification and/or polypeptide expression. The transformation of an expression vector into a selected cell may be accomplished by well-known methods including transfection, infection, calcium phosphate co-precipitation, electroporation, nucleofection, microinjection, DEAE-dextran mediated transfection, cationic lipids mediated delivery, liposome mediated transfection, microprojectile bombardment, receptor-mediated gene delivery, delivery mediated by polylysine, histone, chitosan, and peptides. The method selected will in part be a function of the type of host cell to be used. These methods and other suitable methods are well known to the skilled artisan and are set forth in manuals and other technical publications, for example, in Sambrook et al., Molecular Cloning: A Laboratory Manual, 3rd ed., Cold Spring Harbor Laboratory Press, Cold Spring Harbor, N.Y. (2001).

As used herein, the term "transformation" refers to a change in a cell's genetic characteristics, and a cell has been transformed when it has been modified to contain new DNA or RNA. For example, a cell is transformed where it is genetically modified from its native state by introducing new genetic material via transfection, transduction, or other techniques. Following transfection or transduction, the transforming DNA can recombine with that of the cell by physically integrating into a chromosome of the cell or can be maintained transiently as an episomal element without being replicated, or can replicate independently as a plasmid. A cell is considered to have been "stably transformed" when the transforming DNA is replicated with the division of the cell.

As used herein, the term "transfection" refers to the uptake of foreign or exogenous DNA by a cell. A number of transfection techniques are well known in the art and are disclosed herein. See, e.g., Graham et al., 1973, Virology 52:456: Sambrook et al., 2001, Molecular Cloning: A Laboratory Manual, supra: Davis et al., 1986, Basic Methods in Molecular Biology, Elsevier: Chu et al., 1981, Gene 13:197.

As used herein, the term "transduction" refers to the process whereby foreign DNA is introduced into a cell via viral vector. See Jones et al., (1998). Genetics: principles and analysis. Boston: Jones & Bartlett Publ.

"Cell" or "Cells" include any prokaryotic or eukaryotic cell. Cells can be either ex vivo, in vitro, or in vivo, either separate or as part of a higher structure such as a tissue or organ. Cells include "host cells", also referred to as "cell lines", which are genetically engineered to express a polypeptide of commercial or scientific interest. Host cells are typically derived from a lineage arising from a primary culture that can be maintained in culture for an unlimited time. Genetically engineering the host cell involves transfecting, transforming or transducing the cells with a recombinant polynucleotide molecule, and/or otherwise altering (e.g., by homologous recombination and gene activation or fusion of a recombinant cell with a non-recombinant cell) to cause the host cell to express a desired recombinant polypeptide. Methods and vectors for genetically engineering cells and/or cell lines to express a polypeptide of interest are well known to those of skill in the art: for example, various techniques are illustrated in *Current Protocols in Molecular Biology*, Ausubel et al., eds. (Wiley & Sons, New York, 1990, and quarterly updates); Sambrook et al., Molecular Cloning: A Laboratory Manual (Cold Spring Laboratory Press, 1989); Kaufman, R. J., *Large Scale Mammalian Cell Culture*, 1990, pp. 15-69.

A host cell can be any prokaryotic cell (for example, *E. coli*) or eukaryotic cell (for example, yeast, insect, or animal cells (e.g., CHO cells)). Vector DNA can be introduced into prokaryotic or eukaryotic cells via conventional transformation or transfection techniques. Prokaryotic host cells include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacillus*, such as *B. subtilis* and *B. licheniformis, Pseudomonas*, and *Streptomyces. Saccharomyces cerevisiae*, or common baker's yeast, is the most commonly used among lower eukaryotic host microorganisms. However, a number of other genera, species, and strains are commonly available and useful herein, such as *Pichia*, e.g. *P. pastoris, Schizosaccharomyces pombe: Kluyveromyces, Yarrowia: Candida: Trichoderma* reesia: *Neurospora crassa: Schwanniomyces*, such as *Schwanniomyces occidentalis*; and filamentous fungi, such as, e.g., *Neurospora, Penicillium, Tolypocladium*, and *Aspergillus* hosts such as *nidulans* and *niger.*

Animal cell lines are derived from cells whose progenitors were derived from a multi-cellular animal. One type of animal cell line is a mammalian cell line. A wide variety of mammalian cell lines suitable for growth in culture are available from the American Type Culture Collection (Manassas, Va.) and commercial vendors. Examples of cell lines commonly used in the industry include monkey kidney CVI line transformed by SV40 (COS-7, ATCC CRL 1651); human embryonic kidney line (293 or 293 cells subcloned for growth in suspension culture, (Graham et al, J. Gen Virol. 36:59, 1977); baby hamster kidney cells (BHK, ATCC CCL 10); mouse Sertoli cells (TM4, Mather, Biol. Reprod. 23:243-251, 1980); monkey kidney cells (CVI ATCC CCL 70); African green monkey kidney cells (VERO-76, ATCC CRL-1587): human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human hepatoma cells (Hep G2, HB 8065); mouse mammary tumor (MMT 060562, ATCC CCL51); TRI cells (Mather et al., Annals N.Y Acad. Sci. 383:44-68, 1982); MRC 5 cells or FS4 cells: mammalian myeloma cells, and a number of other cell lines and Chinese hamster ovary (CHO) cells. CHO cells are widely used to produce complex recombinant proteins. The dihydrofolate reductase (DHFR)-deficient mutant cell lines (Urlaub et al. (1980), *Proc Natl Acad Sci USA* 77:4216-4220), DXB11 and DG-44, are desirable CHO host cell lines because the efficient DHFR selectable and amplifiable gene expression system allows high level recombinant protein expression in these cells (Kaufman R. J. (1990), *Meth Enzymol* 185:537-566). Also included are the glutamine synthase (GS)-knockout CHOK1SV cell lines, making use of glutamine synthetase (GS)-based methionine sulfoximine (MSX) selection. Also included is CHOK1 cells (ATCC CCL61). In addition, these cells are easy to manipulate as adherent or suspension cultures and exhibit relatively good genetic stability. CHO cells and proteins recombinantly expressed in them have been extensively characterized and have been approved for use in clinical commercial manufacturing by regulatory agencies.

Cells can also include mononuclear cells, peripheral blood mononuclear cells, bone marrow derived mononuclear cells, umbilical cord blood derived mononuclear cells, lymphocytes, monocytes, dendritic cells, macrophages, T cells, naive T cells, memory T cells, CD28$^+$ cells, CD4$^+$ cells, CD8$^+$ cells, CD45RA$^+$ cells, CD45RO$^+$ cells, natural killer cells, hematopoietic stem cells, pluripotent embryonic stem cells, induced pluripotent stem cells or combinations thereof. In particular, the cells may be collected from a donor or subject for the purpose of genetically modifying and reintroducing the cells to the donor or subject.

In one embodiment is provided a cell transfected with a PIGGYBAC® transposase encoded by the nucleic acid sequence of as described herein. In one embodiment, the invention provides a cell transfected with a PIGGYBAC® transposase encoded by a nucleic acid sequence of SEQ ID NO: 17 or 18. In one embodiment, the invention provides a cell transfected with a vector comprising an engineered nucleic acid molecule encoding a PIGGYBAC® transposase as described herein. In one embodiment, the invention provides a cell transfected with an engineered nucleic acid molecule encoding a PIGGYBAC® transposase as described herein and a vector comprising a nucleic acid molecule encoding a protein of interest flanked by at least the 5' and 3' inverted repeat elements of a PIGGYBAC® transposon. In another embodiment, the invention provides a cell co-transfected with a vector comprising the engineered nucleic acid molecule encoding a PIGGYBAC® transposase as described herein and a vector comprising a nucleic acid sequence encoding a protein of interest flanked by at least the 5' and 3' inverted repeat elements of a PIGGYBAC® transposon. In one embodiment, the invention provides a cell transfected with a vector comprising an engineered nucleic acid molecule encoding a PIGGYBAC® transposase as described herein and a nucleic acid molecule encoding a protein of interest flanked by at least the 5' and 3' inverted repeat elements of a PIGGYBAC® transposon. In a related embodiment the cell is a cell line. In a related embodiment the cell is a host cell. In a related embodiment the cell is a CHO cell. In a related embodiment, the cell is an immune cell. In a related embodiment, the titer of a recombinant protein of interest expressed by the cell transfected with the engineered PIGGYBAC® transposase is improved compared to the titer of the recombinant protein of interest expressed by a cell transfected with a wild type PIGGYBAC® transposase or no PIGGYBAC® transposase. In one embodiment is provides an engineered nucleic acid molecule encoding a PIGGYBAC® transposase as described herein. In one embodiment is provided a PIGGYBAC® transposase encoded by the nucleic acid sequence of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, or SEQ ID NO: 18. In another aspect the invention provides a PIGGYBAC® transposase encoded by the nucleic acid sequence of SEQ ID NO: 3, SEQ ID NO: 5, or SEQ ID NO: 7. In another aspect the invention provides a PIGGYBAC® transposase encoded by the nucleic acid sequence of SEQ ID NO: 11, SEQ ID NO: 13, or SEQ ID NO: 15. In another aspect the invention provides a PIGGYBAC® transposase encoded by the nucleic acid sequence of SEQ ID NO: 9, or SEQ ID NO: 11. In another aspect the invention provides a PIGGYBAC® transposase encoded by the nucleic acid sequence of SEQ ID NO: 17, or SEQ ID NO: 18. In another aspect the invention provides a PIGGYBAC® transposase encoded by the nucleic acid sequence of SEQ ID NO: 3. In another aspect the invention provides a PIGGYBAC® transposase encoded by the nucleic acid sequence of SEQ ID NO: 5. In another aspect the invention provides a PIGGYBAC® transposase encoded by the nucleic acid sequence of SEQ ID NO: 7. In another aspect the invention provides a PIGGYBAC® transposase encoded by the nucleic acid sequence of SEQ ID NO: 9. In another aspect the invention provides a PIGGYBAC® transposase encoded by the nucleic acid sequence of SEQ ID NO: 11. In another aspect the invention provides a PIGGYBAC® transposase encoded by the nucleic acid sequence of SEQ ID NO: 13. In another aspect the invention provides a PIGGYBAC® transposase encoded by the nucleic acid sequence of SEQ ID NO: 15. In another aspect the invention provides a PIGGYBAC® transposase encoded by the nucleic acid sequence of SEQ ID NO: 17. In another aspect the invention provides a PIGGYBAC® transposase encoded by the nucleic acid sequence of SEQ ID NO: 18.

In one embodiment is provided a PIGGYBAC® transposase comprising an amino acid substitution at one or more of the positions 147, 176, 221, 247, 429, 533, and 573 of SEQ ID NO: 2. In a related embodiment the PIGGYBAC® transposase comprises an amino acid substitution of leucine for the isoleucine at one or more of the positions 147, 176, 221, and 247 of SEQ ID NO:2. In a related embodiment the PIGGYBAC® transposase comprises an amino acid substitution of threonine for serine at one or more of the positions 429, 533, and 573 of SEQ ID NO:2. In a related embodiment the PIGGYBAC® transposase comprises an amino acid substitution of leucine for the isoleucine at one or more of the positions 147, 176, 221, and 247 and/or an amino acid substitution of threonine for serine at one or more of the positions 429, 533, and 573 of SEQ ID NO:2. In a related embodiment the PIGGYBAC® transposase comprises at least one of the following amino acid substitutions, a leucine for the isoleucine at position 147 of SEQ ID NO:2, a leucine for the isoleucine at position 247 of SEQ ID NO:2, and a threonine for the serine at position 533 of SEQ ID NO:2. In a related embodiment the PIGGYBAC® transposase comprises at least two of the following amino acid substitutions, a leucine for the isoleucine at position 147 of SEQ ID NO:2, a leucine for the isoleucine at position 247 of SEQ ID NO:2, and a threonine for the serine at position 533 of SEQ ID NO:2. In another related embodiment the PIGGYBAC® transposase comprises a leucine for isoleucine substitution at position 147 of SEQ ID NO:2, a leucine for isoleucine substitution at position 247 of SEQ ID NO:2, and a threonine for serine substitution at position 533 of SEQ ID NO:2. In one embodiment is provided a PIGGYBAC® transposase having the amino acid sequence of SEQ ID NO: 4, SEQ ID NO: 6, SEQ ID NO: 8, SEQ ID NO: 10, SEQ ID NO: 12, SEQ ID NO: 14, or SEQ ID NO: 16. In another aspect the invention provides a PIGGYBAC® transposase having the amino acid sequence of SEQ ID NO: 4, SEQ ID NO: 6, or SEQ ID NO: 8. In another aspect the invention provides a PIGGYBAC® transposase having the amino acid sequence of SEQ ID NO: 12, SEQ ID NO: 14, or SEQ ID NO: 16. In another aspect the invention provides a PIGGYBAC® transposase having the amino acid sequence of SEQ ID NO: 10 or 12. In another aspect the invention provides a PIGGYBAC® transposase having the amino acid sequence of SEQ ID NO:4. In another aspect the invention provides a PIGGYBAC® transposase having the amino acid sequence of SEQ ID NO:6. In another aspect the invention provides a PIGGYBAC® transposase having the amino acid sequence of SEQ ID NO:8. In another aspect the invention provides a PIGGYBAC® transposase having the amino acid sequence of SEQ ID NO:10. In another aspect the invention provides a PIGGYBAC® transposase having the amino acid sequence of SEQ ID NO: 12. In another aspect the invention provides a PIGGYBAC® transposase having the amino acid sequence of SEQ ID NO: 14. In another aspect the invention provides a PIGGYBAC® transposase having the amino acid sequence of SEQ ID NO: 16.

In one embodiment, the invention provides engineering a nucleic acid molecule encoding a PIGGYBAC® transposase to increase stability in a cell and transfecting the cell with a vector comprising the engineered nucleic acid molecule encoding the engineered PIGGYBAC® transposase and a nucleic acid molecule encoding a protein of interest flanked by at least the 5' and 3' inverted repeat elements of a PIGGYBAC® transposon, wherein the titer of the recombinant protein of interest expressed by the cell transfected with the engineered PIGGYBAC® transposase is improved compared to the titer of the recombinant protein of interest expressed by a cell transfected with a wild type PIGGY-BAC® transposase or no PIGGYBAC® transposase. In one embodiment is provides an engineered nucleic acid molecule encoding a PIGGYBAC® transposase as described herein. In one embodiment is provided a PIGGYBAC® transposase encoded by the nucleic acid sequence of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, or SEQ ID NO: 18. In another aspect the invention provides a PIGGYBAC® transposase encoded by the nucleic acid sequence of SEQ ID NO: 3, SEQ ID NO: 5, or SEQ ID NO: 7. In another aspect the invention provides a PIGGYBAC® transposase encoded by the nucleic acid sequence of SEQ ID NO: 11, SEQ ID NO: 13, or SEQ ID NO: 15. In another aspect the invention provides a PIGGY-BAC® transposase encoded by the nucleic acid sequence of SEQ ID NO: 9, or SEQ ID NO: 11. In another aspect the invention provides a PIGGYBAC® transposase encoded by the nucleic acid sequence of SEQ ID NO: 17, or SEQ ID NO: 18. In another aspect the invention provides a PIGGY-BAC® transposase encoded by the nucleic acid sequence of SEQ ID NO: 3. In another aspect the invention provides a PIGGYBAC® transposase encoded by the nucleic acid sequence of SEQ ID NO: 5. In another aspect the invention provides a PIGGYBAC® transposase encoded by the nucleic acid sequence of SEQ ID NO: 7. In another aspect the invention provides a PIGGYBAC® transposase encoded by the nucleic acid sequence of SEQ ID NO: 9. In another aspect the invention provides a PIGGYBAC® transposase encoded by the nucleic acid sequence of SEQ ID NO: 11. In another aspect the invention provides a PIGGYBAC® transposase encoded by the nucleic acid sequence of SEQ ID NO: 13. In another aspect the invention provides a PIGGYBAC® transposase encoded by the nucleic acid sequence of SEQ ID NO: 15. In another aspect the invention provides a PIGGY-BAC® transposase encoded by the nucleic acid sequence of SEQ ID NO: 17. In another aspect the invention provides a PIGGYBAC® transposase encoded by the nucleic acid sequence of SEQ ID NO: 18.

In one embodiment is provided a PIGGYBAC® transposase comprising an amino acid substitution at one or more of the positions 147, 176, 221, 247, 429, 533, and 573 of SEQ ID NO: 2. In a related embodiment the PIGGYBAC® transposase comprises an amino acid substitution of leucine for the isoleucine at one or more of the positions 147, 176, 221, and 247 of SEQ ID NO:2. In a related embodiment the PIGGYBAC® transposase comprises an amino acid substitution of threonine for serine at one or more of the positions 429, 533, and 573 of SEQ ID NO:2. In a related embodiment the PIGGYBAC® transposase comprises an amino acid substitution of leucine for the isoleucine at one or more of the positions 147, 176, 221, and 247 and/or an amino acid substitution of threonine for serine at one or more of the positions 429, 533, and 573 of SEQ ID NO:2. In a related embodiment the PIGGYBAC® transposase comprises at least one of the following amino acid substitutions, a leucine for the isoleucine at position 147 of SEQ ID NO:2, a leucine for the isoleucine at position 247 of SEQ ID NO:2, and a threonine for the serine at position 533 of SEQ ID NO:2. In a related embodiment the PIGGYBAC® transposase comprises at least two of the following amino acid substitutions, a leucine for the isoleucine at position 147 of SEQ ID NO:2, a leucine for the isoleucine at position 247 of SEQ ID NO:2, and a threonine for the serine at position 533 of SEQ ID NO:2. In another related embodiment the PIGGYBAC® transposase comprises a leucine for isoleucine substitution at position 147 of SEQ ID NO:2, a leucine for isoleucine substitution at position 247 of SEQ ID NO:2, and a threonine for serine substitution at position 533 of SEQ ID NO:2.

In one embodiment is provided a PIGGYBAC® transposase having the amino acid sequence of SEQ ID NO: 4, SEQ ID NO: 6, SEQ ID NO: 8, SEQ ID NO: 10, SEQ ID NO: 12, SEQ ID NO: 14, or SEQ ID NO: 16. In another aspect the invention provides a PIGGYBAC® transposase having the amino acid sequence of SEQ ID NO: 4, SEQ ID NO: 6, or SEQ ID NO: 8. In another aspect the invention provides a PIGGYBAC® transposase having the amino acid sequence of SEQ ID NO: 12, SEQ ID NO: 14, or SEQ ID NO: 16. In another aspect the invention provides a PIGGYBAC® transposase having the amino acid sequence of SEQ ID NO: 10 or 12. In another aspect the invention provides a PIGGYBAC® transposase having the amino acid sequence of SEQ ID NO:4. In another aspect the invention provides a PIGGYBAC® transposase having the amino acid sequence of SEQ ID NO:6. In another aspect the invention provides a PIGGYBAC® transposase having the amino acid sequence of SEQ ID NO:8. In another aspect the invention provides a PIGGYBAC® transposase having the amino acid sequence of SEQ ID NO:10. In another aspect the invention provides a PIGGYBAC® transposase having the amino acid sequence of SEQ ID NO: 12. In another aspect the invention provides a PIGGYBAC® transposase having the amino acid sequence of SEQ ID NO: 14. In another aspect the invention provides a PIGGYBAC® transposase having the amino acid sequence of SEQ ID NO: 16.

In one embodiment, the invention provides engineering a nucleic acid molecule encoding a PIGGYBAC" transposase to increase stability in a cell and co-transfecting the cell with a vector comprising the engineered nucleic acid molecule encoding the engineered PIGGYBAC® transposase and a vector comprising the nucleic acid molecule encoding a protein of interest flanked by at least the 5' and 3' inverted repeat elements of a PIGGYBAC® transposon, wherein the titer of the recombinant protein of interest expressed by the cell transfected with the engineered PIGGYBAC® transposase is improved compared to the titer of the recombinant protein of interest expressed by a cell transfected with a wild type PIGGYBAC® transposase or no PIGGYBAC® transposase.

Also provided is a host cell transfected with a vector including a nucleic acid encoding a protein of interest, when cultured under appropriate conditions, expresses the protein of interest. The expressed protein may be subsequently collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

In one embodiment, the invention provides a recombinant protein of interest expressed by a cell transfected with a vector comprising an engineered nucleic acid molecule encoding a PIGGYBAC® transposase as described herein. In one embodiment, the invention provides a cell transfected with a vector comprising the engineered nucleic acid molecule encoding a PIGGYBAC® transposase as described herein, the vector further comprising a nucleic acid sequence encoding a protein of interest flanked by at least the 5' and 3' inverted repeat elements of a PIGGYBAC® transposon. In one embodiment, the invention provides a recombinant protein of interest expressed by a cell co-transfected with a vector comprising an engineered nucleic acid molecule encoding a PIGGYBAC® transposase as described herein and a vector comprising a nucleic acid molecule encoding a protein of interest flanked by at least the 5' and 3' inverted repeat elements of a PIGGYBAC® transposon.

In one embodiment, the invention provides a pharmaceutical composition comprising a recombinant protein of interest expressed by a cell host transfected with a vector comprising an engineered nucleic acid molecule encoding a PIGGYBAC® transposase as described herein. In one embodiment, the invention provides a host cell transfected with a vector comprising the engineered nucleic acid molecule encoding a PIGGYBAC® transposase as described herein, the vector further comprising a nucleic acid sequence encoding a protein of interest flanked by at least the 5' and 3' inverted repeat elements of a PIGGYBAC® transposon. In one embodiment, the invention provides a pharmaceutical composition comprising a recombinant protein of interest expressed by a host cell co-transfected with a vector comprising an engineered nucleic acid molecule encoding a PIGGYBAC® transposase as described herein and a vector comprising a nucleic acid molecule encoding a protein of interest flanked by at least the 5' and 3' inverted repeat elements of a PIGGYBAC® transposon.

By "culture" or "culturing" is meant the growth and propagation of cells outside of a multicellular organism or tissue. Suitable culture conditions for mammalian cells are known in the art. Cell culture media and tissue culture media are interchangeably used to refer to media suitable for growth of a host cell during in vitro cell culture. Typically, cell culture media contains a buffer, salts, energy source, amino acids, vitamins and trace essential elements. Any media capable of supporting growth of the appropriate host cell in culture can be used. Cell culture media, which may be further supplemented with other components to maximize cell growth, cell viability, and/or recombinant protein production in a particular cultured host cell, are commercially available and include RPMI-1640 Medium, RPMI-1641 Medium, Dulbecco's Modified Eagle's Medium (DMEM), Minimum Essential Medium Eagle, F-12K Medium, Ham's F12 Medium, Iscove's Modified Dulbecco's Medium, McCoy's 5A Medium, Leibovitz's L-15 Medium, and serum-free media such as EX-CELL™ 300 Series, among others, which can be obtained from the American Type Culture Collection or SAFC Biosciences, as well as other vendors. Cell culture media can be serum-free, protein-free, growth factor-free, and/or peptone-free media. Cell culture may also be enriched by the addition of nutrients and used at greater than its usual, recommended concentrations.

Various media formulations can be used during the life of the culture, for example, to facilitate the transition from one stage (e.g., the growth stage or phase) to another (e.g., the production stage or phase) and/or to optimize conditions during cell culture (e.g. concentrated media provided during perfusion culture). A growth medium formulation can be used to promote cell growth and minimize protein expression. A production medium formulation can be used to promote production of the protein of interest and maintenance of the cells, with a minimal of new cell growth). A feed media, typically a media containing more concentrated components such as nutrients and amino acids, which are consumed during the course of the production phase of the cell culture may be used to supplement and maintain an active culture, particularly a culture operated in fed batch, semi-perfusion, or perfusion mode. Such a concentrated feed medium can contain most of the components of the cell culture medium at, for example, about 5×, 6×, 7×, 8×, 9×, 10×, 12×, 14×, 16×, 20×, 30×, 50×, 100×, 200×, 400×, 600×, 800×, or even about 1000× of their normal amount.

A growth phase may occur at a higher temperature than a production phase. For example, a growth phase may occur at a first temperature from about 35° C. to about 38° C., and a production phase may occur at a second temperature from about 29° C. to about 37° C., optionally from about 30° C. to about 36° C. or from about 30° C. to about 34° C. Chemical inducers of protein production, such as, for example, caffeine, butyrate, and hexamethylene bisacetamide (HMBA), may be added at the same time as, before, and/or after a temperature shift, or in place of a temperature shift. If inducers are added after a temperature shift, they can be added from one hour to five days after the temperature shift, optionally from one to two days after the temperature shift.

Host cells may be cultured in suspension or in an adherent form, attached to a solid substrate. Cell cultures can be established in fluidized bed bioreactors, hollow fiber bioreactors, roller bottles, shake flasks, or stirred tank bioreactors, with or without microcarriers Cell cultures can be operated in a batch, fed batch, continuous, semi-continuous, or perfusion mode. Mammalian cells, such as CHO cells, may be cultured in bioreactors at a small scale of less than 100 ml to less than 1000 mls, a more medium range scale with a capacity to over 2,000 liters and larger scale where capacity can exceed 20,000 liters. Medium and large-scale cell cultures, such as for clinical and/or commercial scale biomanufacturing of protein therapeutics, may be maintained for weeks and even months, while the cells produce the desired protein(s).

The resulting expressed recombinant protein can then be harvested from the cell culture media. Methods for harvesting protein from suspension cells are known in the art and include, but are not limited to, acid precipitation, accelerated sedimentation such as flocculation, separation using gravity, centrifugation, acoustic wave separation, filtration, including membrane filtration using ultrafilters, microfilters, tangential flow filters, alternative tangential flow filters, depth filters, and alluvial filters. Recombinant proteins expressed by prokaryotes are retrieved from inclusion bodies in the cytoplasm by processes incorporating redox folding processes known in the art.

The harvested protein can then be purified, or partially purified, away from any impurities, such as remaining cell culture media, cell extracts, undesired components, host cell proteins, improperly expressed proteins and the like, using one or more unit operations. The term "unit operation" refers to a functional step that is performed as part of the process of purifying a recombinant protein of interest. For example, a unit operation can include steps such as, but not limited to, capturing, purifying, polishing, viral inactivating, virus filtering, concentrating and/or formulating the recombinant protein of interest. Unit operations can be designed to achieve a single objective or multiple objectives, such as capture and virus inactivating steps. Unit operations can also include holding or storing steps between processing steps.

A capture unit operation may include capture chromatography that makes use of resins and/or membranes containing agents that will bind to the recombinant protein of interest, for example affinity chromatography, size exclusion chromatography, ion exchange chromatography, hydrophobic interaction chromatography (HIC), immobilized metal affinity chromatography (IMAC), and the like. Such materials are known in the art and are commercially available. Affinity chromatography, for example can make use of antibody- or antibody fragment-binding capture mechanisms, such as Protein A, Protein G, Protein A/G, Protein L-binding. The recombinant protein of interest can be tagged with a polyhistidine tag and subsequently purified from IMAC using imidazole or an epitope, such a FLAG® and subsequently purified by using a specific antibody directed to such epitope.

Unit operations comprising inactivating, reducing and/or eliminating viral contaminants may include processes that manipulate the environment and/or filtration. One method for achieving virus inactivation is incubation at low pH (e.g., pH<4) or other solution conditions, such as temperature or chemical composition, for achieving viral inactivation. Low pH virus inactivation can be followed with a neutralization unit operation that readjusts the viral inactivated solution to a pH more compatible with the requirements of the following unit operations. It may also be followed by filtration, such as depth filtration, to remove any resulting turbidity or precipitation. Viral filtration can be performed using micro- or nano-filters, such as those available from Asahi Kasei (Plavona®) and EDM Millipore (VPro®).

A polishing unit operation may make use of various chromatography methods for the purification of the protein of interest and clearance of contaminants and impurities such as DNA, host cell proteins: removal of product-specific impurities, variant products and aggregates, virus adsorption, and the like. The polish chromatography unit operation makes use of resins and/or membranes containing agents that can be used in either a "flow-through mode" (where the protein of interest is contained in the eluent and the contaminants and impurities are bound to the chromatography medium) or "bind and elute mode", where the protein of interest is bound to the chromatography medium and eluted after the contaminants and impurities have flowed through or been washed off the chromatography medium. Examples of such chromatography methods include ion exchange chromatography (IEX), such as anion exchange chromatography (AEX) and cation exchange chromatography (CEX); hydrophobic interaction chromatography (HIC); mixed modal or multimodal chromatography (MM), hydroxyapatite chromatography (HA); reverse phase chromatography and gel filtration, to name a few.

Product concentration and buffer exchange of the protein of interest into a desired formulation buffer for bulk storage of the drug substance can be accomplished by ultrafiltration and diafiltration.

Critical attributes and performance parameters can be measured to better inform decisions regarding performance of each step during manufacture. These critical attributes and parameters can be monitored real-time, near real-time, and/or after the fact. Key critical parameters such as media components that are consumed (such as glucose), levels of metabolic by-products (such as lactate and ammonia) that accumulate, as well as those related to cell maintenance and survival, such as dissolved oxygen content can be measured. Critical attributes such as specific productivity, viable cell density, pH, osmolality, appearance, color, aggregation, percent yield and titer may be monitored during and after the process. Monitoring and measurements can be done using known techniques and commercially available equipment.

Titer may be measured using methods known in the art. For example, titer may be measured by reverse-phase HPLC analysis using affinity chromatography where Protein A is immobilized on a column support. At neutral pH, antibody molecules bind to the Protein A through the Fc region while host-cell proteins, conditioned media components and buffer are eluted from the column in the flow-through. Captured antibodies are eluted at acidic pH and detected by UV absorbance at 280 nm. A calibration curve may be derived from a universal antibody standard and the corresponding peak areas using linear regression analysis. Concentrations of the antibody in the test samples are then calculated from the calibration curve and the ratio of the extinction coefficients from the Universal antibody standard and the antibody tested.

Other methods include, but are not limited to, ELISA; HTRF (Homogeneous Time Resolved Fluorescence) (Cisbio US, Bedford, MA); and the Berkley Lights Beacon platform (Emeryville. CA).

Also provided are pharmaceutical compositions comprising a recombinant protein of interest expressed by a cell host transfected with a vector comprising an engineered nucleic acid molecule encoding a PIGGYBAC® transposase. Such pharmaceutical compositions include a protein of interest or cells expressing a protein of interest, such as an immune cell expressing CARs and TCRs, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione: adjuvants (e.g., aluminum hydroxide); and preservatives.

The pharmaceutical compositions (solutions, suspensions or the like), may include one or more of the following: sterile diluents such as water for injection, saline solution, preferably physiological saline, Ringer's solution, isotonic sodium chloride, fixed oils such as synthetic mono- or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid: buffers such as acetates, citrates or phosphates and agents for the adjustment of tonicity such as sodium chloride or dextrose. The parenteral preparation can be enclosed in ampoules, disposable syringes or multiple dose vials made of glass or plastic.

In one embodiment the invention provides a method for improving the titer of a recombinant protein of interest expressed by a host cell comprising engineering the nucleic acid molecule encoding a PIGGYBAC® transposase to increase stability in the host cell, co-transfecting a host cell with the engineered nucleic acid molecule encoding the PIGGYBAC® transposase and with a vector comprising the nucleic acid sequence encoding the protein of interest flanked by at least the 5' and 3' inverted repeat elements of a PIGGYBAC® transposon, and culturing the cells to express the recombinant protein of interest, wherein the titer of the recombinant protein of interest expressed by the host cell transfected with the engineered PIGGYBAC® transposase is improved compared to the titer of the recombinant protein of interest expressed by a host cell transfected with a wild type PIGGYBAC® transposase or no PIGGYBAC® transposase. In a related embodiment the host cell is transfected with a first vector comprising the engineered nucleic acid molecule encoding the PIGGYBAC® transposase and a second vector comprising a nucleic acid sequence encoding the protein of interest flanked by at least the 5' and 3' inverted repeat elements of a PIGGYBAC® transposon. In a related embodiment the host cell is transfected with a single vector comprising the engineered nucleic acid molecule encoding the PIGGYBAC® transposase and a nucleic acid sequence encoding the protein of interest flanked by at least the 5' and 3' inverted repeat elements of a PIGGY-BAC® transposon. In one embodiment is provides an engineered nucleic acid molecule encoding a PIGGYBAC® transposase as described herein. In one embodiment is provided a PIGGYBAC® transposase encoded by the nucleic acid sequence of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, or SEQ ID NO: 18. In another aspect the invention provides a PIGGYBAC® transposase encoded by the nucleic acid sequence of SEQ ID NO: 3, SEQ ID NO: 5, or SEQ ID NO: 7. In another aspect the invention provides a PIGGYBAC® transposase encoded by the nucleic acid sequence of SEQ ID NO: 11, SEQ ID NO: 13, or SEQ ID NO: 15. In another aspect the invention provides a PIGGYBAC® transposase encoded by the nucleic acid sequence of SEQ ID NO: 9, or SEQ ID NO: 11. In another aspect the invention provides a PIGGYBAC® transposase encoded by the nucleic acid sequence of SEQ ID NO: 17, or SEQ ID NO: 18. In another aspect the invention provides a PIGGYBAC® transposase encoded by the nucleic acid sequence of SEQ ID NO: 3. In another aspect the invention provides a PIGGYBAC® transposase encoded by the nucleic acid sequence of SEQ ID NO: 5. In another aspect the invention provides a PIGGYBAC® transposase encoded by the nucleic acid sequence of SEQ ID NO: 7. In another aspect the invention provides a PIGGYBAC® transposase encoded by the nucleic acid sequence of SEQ ID NO: 9. In another aspect the invention provides a PIGGYBAC® transposase encoded by the nucleic acid sequence of SEQ ID NO: 11. In another aspect the invention provides a PIGGY-BAC® transposase encoded by the nucleic acid sequence of SEQ ID NO: 13. In another aspect the invention provides a PIGGYBAC® transposase encoded by the nucleic acid sequence of SEQ ID NO: 15. In another aspect the invention provides a PIGGYBAC® transposase encoded by the nucleic acid sequence of SEQ ID NO: 17. In another aspect the invention provides a PIGGYBAC® transposase encoded by the nucleic acid sequence of SEQ ID NO: 18.

In one embodiment is provided a PIGGYBAC® transposase comprising an amino acid substitution at one or more of the positions 147, 176, 221, 247, 429, 533, and 573 of SEQ ID NO: 2. In a related embodiment the PIGGYBAC® transposase comprises an amino acid substitution of leucine for the isoleucine at one or more of the positions 147, 176, 221, and 247 of SEQ ID NO:2. In a related embodiment the PIGGYBAC® transposase comprises an amino acid substitution of threonine for serine at one or more of the positions 429, 533, and 573 of SEQ ID NO:2. In a related embodiment the PIGGYBAC® transposase comprises an amino acid substitution of leucine for the isoleucine at one or more of the positions 147, 176, 221, and 247 and/or an amino acid substitution of threonine for serine at one or more of the positions 429, 533, and 573 of SEQ ID NO:2. In a related embodiment the PIGGYBAC® transposase comprises at least one of the following amino acid substitutions, a leucine for the isoleucine at position 147 of SEQ ID NO:2, a leucine for the isoleucine at position 247 of SEQ ID NO:2, and a threonine for the serine at position 533 of SEQ ID NO:2. In a related embodiment the PIGGYBAC® transposase comprises at least two of the following amino acid substitutions, a leucine for the isoleucine at position 147 of SEQ ID NO:2, a leucine for the isoleucine at position 247 of SEQ ID NO:2, and a threonine for the serine at position 533 of SEQ ID NO:2. In another related embodiment the PIGGYBAC® transposase comprises a leucine for isoleucine substitution at position 147 of SEQ ID NO:2, a leucine for isoleucine substitution at position 247 of SEQ ID NO:2, and a threonine for serine substitution at position 533 of SEQ ID NO:2. In one embodiment is provided a PIGGYBAC® transposase having the amino acid sequence of SEQ ID NO: 4, SEQ ID NO: 6, SEQ ID NO: 8, SEQ ID NO: 10, SEQ ID NO: 12, SEQ ID NO: 14, or SEQ ID NO: 16. In another aspect the invention provides a PIGGYBAC® transposase having the amino acid sequence of SEQ ID NO: 4, SEQ ID NO: 6, or SEQ ID NO: 8. In another aspect the invention provides a PIGGYBAC® transposase having the amino acid sequence of SEQ ID NO: 12, SEQ ID NO: 14, or SEQ ID NO: 16. In another aspect the invention provides a PIGGYBAC® transposase having the amino acid sequence of SEQ ID NO: 10 or 12. In another aspect the invention provides a PIGGYBAC® transposase having the amino acid sequence of SEQ ID NO:4. In another aspect the invention provides a PIGGYBAC® transposase having the amino acid sequence of SEQ ID NO:6. In another aspect the invention provides a PIGGYBAC® transposase having the amino acid sequence of SEQ ID NO:8. In another aspect the invention provides a PIGGYBAC® transposase having the amino acid sequence of SEQ ID NO:10. In another aspect the invention provides a PIGGYBAC® transposase having the amino acid sequence of SEQ ID NO: 12. In another aspect the invention provides a PIGGYBAC® transposase having the amino acid sequence of SEQ ID NO: 14. In another aspect the invention provides a PIGGYBAC® transposase having the amino acid sequence of SEQ ID NO: 16.

In one embodiment, the invention provides a method for increasing recombinant protein production in a mammalian cell culture expressing a recombinant protein comprising establishing a cell culture in a bioreactor using a host cell that has been co-transfected with a nucleic acid molecule engineered to increase stability in the host cell, and a vector comprising the nucleic acid molecule encoding the protein of interest flanked by at least the inverted repeat elements of a PIGGYBAC® transposon; and expressing the recombinant protein of interest: wherein the titer of the recombinant protein of interest expressed by the host cell transfected with the engineered PIGGYBAC® transposase is improved compared to the titer of the recombinant protein of interest expressed by the host cell transfected with a wild type PIGGYBAC® transposase or no PIGGYBAC® transposase. In a related embodiment, the host cell is transfected with a first vector comprising the engineered nucleic acid molecule encoding the PIGGYBAC® transposase and a second vector comprising a nucleic acid sequence encoding the protein of interest flanked by at least the 5' and 3' inverted repeat elements of a PIGGYBAC® transposon. In a related embodiment, the host cell is transfected with a single vector comprising the engineered nucleic acid molecule encoding the PIGGYBAC® transposase and a nucleic acid sequence encoding the protein of interest flanked by at least the 5' and 3' inverted repeat elements of a PIGGYBAC® transposon. In one embodiment is provides an engineered nucleic acid molecule encoding a PIGGYBAC® transposase as described herein. In one embodiment is provided a PIGGYBAC® transposase encoded by the nucleic acid sequence of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, or SEQ ID NO: 18. In another aspect the invention provides a PIGGYBAC® transposase encoded by the nucleic acid sequence of SEQ ID NO: 3, SEQ ID NO: 5, or SEQ ID NO: 7. In another aspect the invention provides a PIGGYBAC® transposase encoded by the nucleic acid sequence of SEQ ID NO: 11, SEQ ID NO: 13, or SEQ ID NO: 15. In another aspect the invention provides a PIGGYBAC® transposase encoded by the nucleic acid sequence of SEQ ID NO: 9, or SEQ ID NO: 11. In another aspect the invention provides a PIGGYBAC® transposase encoded by the nucleic acid sequence of SEQ ID NO: 17, or SEQ ID NO:18. In another aspect the invention provides a PIGGYBAC® transposase encoded by the nucleic acid sequence of SEQ ID NO: 3. In another aspect the invention provides a PIGGYBAC® transposase encoded by the nucleic acid sequence of SEQ ID NO: 5. In another aspect the invention provides a PIGGYBAC® transposase encoded by the nucleic acid sequence of SEQ ID NO: 7. In another aspect the invention provides a PIGGYBAC® transposase encoded by the nucleic acid sequence of SEQ ID NO: 9. In another aspect the invention provides a PIGGYBAC® transposase encoded by the nucleic acid sequence of SEQ ID NO: 11. In another aspect the invention provides a PIGGYBAC® transposase encoded by the nucleic acid sequence of SEQ ID NO: 13. In another aspect the invention provides a PIGGYBAC® transposase encoded by the nucleic acid sequence of SEQ ID NO: 15. In another aspect the invention provides a PIGGYBAC® transposase encoded by the nucleic acid sequence of SEQ ID NO: 17. In another aspect the invention provides a PIGGYBAC® transposase encoded by the nucleic acid sequence of SEQ ID NO:18.

In one embodiment is provided a PIGGYBAC® transposase comprising an amino acid substitution at one or more of the positions 147, 176, 221, 247, 429, 533, and 573 of SEQ ID NO: 2. In a related embodiment the PIGGYBAC® transposase comprises an amino acid substitution of leucine for the isoleucine at one or more of the positions 147, 176, 221, and 247 of SEQ ID NO:2. In a related embodiment the PIGGYBAC® transposase comprises an amino acid substitution of threonine for serine at one or more of the positions 429, 533, and 573 of SEQ ID NO:2. In a related embodiment the PIGGYBAC® transposase comprises an amino acid substitution of leucine for the isoleucine at one or more of the positions 147, 176, 221, and 247 and/or an amino acid substitution of threonine for serine at one or more of the positions 429, 533, and 573 of SEQ ID NO:2. In a related embodiment the PIGGYBAC® transposase comprises at least one of the following amino acid substitutions, a leucine for the isoleucine at position 147 of SEQ ID NO:2, a leucine for the isoleucine at position 247 of SEQ ID NO:2, and a threonine for the serine at position 533 of SEQ ID NO:2. In a related embodiment the PIGGYBAC® transposase comprises at least two of the following amino acid substitutions, a leucine for the isoleucine at position 147 of SEQ ID NO:2, a leucine for the isoleucine at position 247 of SEQ ID NO:2, and a threonine for the serine at position 533 of SEQ ID NO:2. In another related embodiment the PIGGYBAC® transposase comprises a leucine for isoleucine substitution at position 147 of SEQ ID NO:2, a leucine for isoleucine substitution at position 247 of SEQ ID NO:2, and a threonine for serine substitution at position 533 of SEQ ID NO:2. In one embodiment is provided a PIGGYBAC® transposase having the amino acid sequence of SEQ ID NO: 4, SEQ ID NO: 6, SEQ ID NO: 8, SEQ ID NO: 10, SEQ ID NO: 12, SEQ ID NO: 14, or SEQ ID NO: 16. In another aspect the invention provides a PIGGYBAC® transposase having the amino acid sequence of SEQ ID NO: 4, SEQ ID NO: 6, or SEQ ID NO: 8. In another aspect the invention provides a PIGGYBAC® transposase having the amino acid sequence of SEQ ID NO: 12, SEQ ID NO: 14, or SEQ ID NO: 16. In another aspect the invention provides a PIGGYBAC® transposase having the amino acid sequence of SEQ ID NO: 10 or 12. In another aspect the invention provides a PIGGYBAC® transposase having the amino acid sequence of SEQ ID NO:4. In another aspect the invention provides a PIGGYBAC® transposase having the amino acid sequence of SEQ ID NO:6. In another aspect the invention provides a PIGGYBAC® transposase having the amino acid sequence of SEQ ID NO:8. In another aspect the invention provides a PIGGYBAC® transposase having the amino acid sequence of SEQ ID NO:10. In another aspect the invention provides a PIGGYBAC® transposase having the amino acid sequence of SEQ ID NO: 12. In another aspect the invention provides a PIGGYBAC® transposase having the amino acid sequence of SEQ ID NO: 14. In another aspect the invention provides a PIGGYBAC® transposase having the amino acid sequence of SEQ ID NO: 16.

In one embodiment the invention provides a method for producing an isolated, purified, recombinant protein of interest comprising establishing a cell culture in a bioreactor with a host cell expressing a recombinant protein of interest, wherein the cell line has been co-transfected with a nucleic acid sequence encoding a PIGGYBAC® transposase engineered to increase stability in the host cell and a vector comprising the nucleic acid sequence encoding the protein of interest flanked by at least the 5' and 3' inverted repeat elements of a PIGGYBAC® transposon: culturing the cells to express the recombinant protein of interest: harvesting the recombinant protein of interest, processing the recombinant protein of interest through one or more unit operations, and obtaining an isolated, purified, recombinant protein of interest. In a related embodiment the host cell is transfected with a first vector comprising the engineered nucleic acid molecule encoding the PIGGYBAC® transposase and a second vector comprising a nucleic acid sequence encoding the protein of interest flanked by at least the 5' and 3' inverted repeat elements of a PIGGYBAC® transposon. In a related embodiment the host cell is transfected with a single vector comprising the engineered nucleic acid molecule encoding the PIGGYBAC® transposase and a nucleic acid sequence encoding the protein of interest flanked by at least the 5' and 3' inverted repeat elements of a PIGGYBAC® transposon. In a related embodiment at least one unit operation is a capture chromatography step selected from affinity chromatography, ion exchange chromatography, anion exchange chromatography, cation exchange chromatography, multimodal chromatography, hydrophobic interaction chromatography, and hydroxyapatite chromatography. In another embodiment at least one unit operation is a polish chromatography step selected from ion exchange chromatography, anion exchange chromatography, cation exchange chromatography, multi-modal chromatography, hydrophobic interaction chromatography, and hydroxyapatite chromatography. In another embodiment at least one unit operation is selected from virus inactivation, virus filtration, depth filtration, and UF/DF. In a related embodiment the titer of the recombinant protein of interest expressed by the host cell transfected with the engineered PIGGYBAC® transposase is improved compared to the titer of the recombinant protein of interest expressed by the host cell transfected with a wild type PIGGYBAC® transposase or no PIGGYBAC® transposase. In another embodiment is provided an isolated, purified, recombinant protein of interest produced by the method. In another embodiment is provided pharmaceutical composition comprising the isolated protein of interest. In one embodiment is provides an engineered nucleic acid molecule encoding a PIGGYBAC® transposase as described herein. In one embodiment is provided a PIGGYBAC® transposase encoded by the nucleic acid sequence of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, or SEQ ID NO:18. In another aspect the invention provides a PIGGYBAC® transposase encoded by the nucleic acid sequence of SEQ ID NO: 3, SEQ ID NO:

5, or SEQ ID NO: 7. In another aspect the invention provides a PIGGYBAC® transposase encoded by the nucleic acid sequence of SEQ ID NO: 11, SEQ ID NO: 13, or SEQ ID NO: 15. In another aspect the invention provides a PIGGYBAC® transposase encoded by the nucleic acid sequence of SEQ ID NO: 9, or SEQ ID NO: 11. In another aspect the invention provides a PIGGYBAC® transposase encoded by the nucleic acid sequence of SEQ ID NO: 17, or SEQ ID NO: 18. In another aspect the invention provides a PIGGYBAC® transposase encoded by the nucleic acid sequence of SEQ ID NO: 3. In another aspect the invention provides a PIGGYBAC® transposase encoded by the nucleic acid sequence of SEQ ID NO: 5. In another aspect the invention provides a PIGGYBAC® transposase encoded by the nucleic acid sequence of SEQ ID NO: 7. In another aspect the invention provides a PIGGYBAC® transposase encoded by the nucleic acid sequence of SEQ ID NO: 9. In another aspect the invention provides a PIGGYBAC® transposase encoded by the nucleic acid sequence of SEQ ID NO: 11. In another aspect the invention provides a PIGGYBAC® transposase encoded by the nucleic acid sequence of SEQ ID NO: 13. In another aspect the invention provides a PIGGYBAC® transposase encoded by the nucleic acid sequence of SEQ ID NO: 15. In another aspect the invention provides a PIGGYBAC® transposase encoded by the nucleic acid sequence of SEQ ID NO: 17. In another aspect the invention provides a PIGGYBAC® transposase encoded by the nucleic acid sequence of SEQ ID NO: 18.

In one embodiment is provided a PIGGYBAC® transposase comprising an amino acid substitution at one or more of the positions 147, 176, 221, 247, 429, 533, and 573 of SEQ ID NO: 2. In a related embodiment the PIGGYBAC® transposase comprises an amino acid substitution of leucine for the isoleucine at one or more of the positions 147, 176, 221, and 247 of SEQ ID NO:2. In a related embodiment the PIGGYBAC® transposase comprises an amino acid substitution of threonine for serine at one or more of the positions 429, 533, and 573 of SEQ ID NO:2. In a related embodiment the PIGGYBAC® transposase comprises an amino acid substitution of leucine for the isoleucine at one or more of the positions 147, 176, 221, and 247 and/or an amino acid substitution of threonine for serine at one or more of the positions 429, 533, and 573 of SEQ ID NO:2. In a related embodiment the PIGGYBAC® transposase comprises at least one of the following amino acid substitutions, a leucine for the isoleucine at position 147 of SEQ ID NO:2, a leucine for the isoleucine at position 247 of SEQ ID NO:2, and a threonine for the serine at position 533 of SEQ ID NO:2. In a related embodiment the PIGGYBAC® transposase comprises at least two of the following amino acid substitutions, a leucine for the isoleucine at position 147 of SEQ ID NO:2, a leucine for the isoleucine at position 247 of SEQ ID NO:2, and a threonine for the serine at position 533 of SEQ ID NO:2. In another related embodiment the PIGGYBAC® transposase comprises a leucine for isoleucine substitution at position 147 of SEQ ID NO:2, a leucine for isoleucine substitution at position 247 of SEQ ID NO:2, and a threonine for serine substitution at position 533 of SEQ ID NO:2. In one embodiment is provided a PIGGYBAC® transposase having the amino acid sequence of SEQ ID NO: 4, SEQ ID NO: 6, SEQ ID NO: 8, SEQ ID NO: 10, SEQ ID NO: 12, SEQ ID NO: 14, or SEQ ID NO: 16. In another aspect the invention provides a PIGGYBAC® transposase having the amino acid sequence of SEQ ID NO: 4, SEQ ID NO: 6, or SEQ ID NO: 8. In another aspect the invention provides a PIGGYBAC® transposase having the amino acid sequence of SEQ ID NO: 12, SEQ ID NO: 14, or SEQ ID NO: 16. In another aspect the invention provides a PIGGYBAC® transposase having the amino acid sequence of SEQ ID NO: 10 or 12. In another aspect the invention provides a PIGGYBAC® transposase having the amino acid sequence of SEQ ID NO:4. In another aspect the invention provides a PIGGYBAC® transposase having the amino acid sequence of SEQ ID NO:6. In another aspect the invention provides a PIGGYBAC® transposase having the amino acid sequence of SEQ ID NO:8. In another aspect the invention provides a PIGGYBAC® transposase having the amino acid sequence of SEQ ID NO:10. In another aspect the invention provides a PIGGYBAC® transposase having the amino acid sequence of SEQ ID NO: 12. In another aspect the invention provides a PIGGYBAC® transposase having the amino acid sequence of SEQ ID NO: 14. In another aspect the invention provides a PIGGYBAC® transposase having the amino acid sequence of SEQ ID NO: 16.

In one embodiment the invention provides a kit for transfecting a cell comprising a vector comprising a nucleic acid sequence encoding a PIGGYBAC® transposase engineered to increase stability in the host cell and a vector comprising at least the minimal inverted repeat elements of a PIGGYBAC® transposon into which the nucleic acid sequence encoding a protein of interest is inserted. In one embodiment is provides an engineered nucleic acid molecule encoding a PIGGYBAC® transposase as described herein. In one embodiment is provided a PIGGYBAC® transposase encoded by the nucleic acid sequence of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, or SEQ ID NO:18. In another aspect the invention provides a PIGGYBAC® transposase encoded by the nucleic acid sequence of SEQ ID NO: 3, SEQ ID NO: 5, or SEQ ID NO: 7. In another aspect the invention provides a PIGGYBAC® transposase encoded by the nucleic acid sequence of SEQ ID NO: 11, SEQ ID NO: 13, or SEQ ID NO: 15. In another aspect the invention provides a PIGGYBAC" transposase encoded by the nucleic acid sequence of SEQ ID NO: 9, or SEQ ID NO: 11. In another aspect the invention provides a PIGGYBAC® transposase encoded by the nucleic acid sequence of SEQ ID NO: 17, or SEQ ID NO: 18. In another aspect the invention provides a PIGGYBAC® transposase encoded by the nucleic acid sequence of SEQ ID NO: 3. In another aspect the invention provides a PIGGYBAC® transposase encoded by the nucleic acid sequence of SEQ ID NO: 5. In another aspect the invention provides a PIGGYBAC® transposase encoded by the nucleic acid sequence of SEQ ID NO: 7. In another aspect the invention provides a PIGGYBAC® transposase encoded by the nucleic acid sequence of SEQ ID NO: 9. In another aspect the invention provides a PIGGYBAC® transposase encoded by the nucleic acid sequence of SEQ ID NO: 11. In another aspect the invention provides a PIGGYBAC® transposase encoded by the nucleic acid sequence of SEQ ID NO: 13. In another aspect the invention provides a PIGGYBAC® transposase encoded by the nucleic acid sequence of SEQ ID NO: 15. In another aspect the invention provides a PIGGYBAC® transposase encoded by the nucleic acid sequence of SEQ ID NO: 17. In another aspect the invention provides a PIGGYBAC® transposase encoded by the nucleic acid sequence of SEQ ID NO: 18.

In one embodiment is provided a PIGGYBAC® transposase comprising an amino acid substitution at one or more of the positions 147, 176, 221, 247, 429, 533, and 573 of SEQ ID NO: 2. In a related embodiment the PIGGYBAC® transposase comprises an amino acid substitution of leucine for the isoleucine at one or more of the positions 147, 176, 221, and 247 of SEQ ID NO:2. In a related embodiment the PIGGYBAC® transposase comprises an amino acid substitution of threonine for serine at one or more of the positions 429, 533, and 573 of SEQ ID NO:2. In a related embodiment the PIGGYBAC® transposase comprises an amino acid substitution of leucine for the isoleucine at one or more of the positions 147, 176, 221, and 247 and/or an amino acid substitution of threonine for serine at one or more of the positions 429, 533, and 573 of SEQ ID NO:2. In a related embodiment the PIGGYBAC® transposase comprises at least one of the following amino acid substitutions, a leucine for the isoleucine at position 147 of SEQ ID NO:2, a leucine for the isoleucine at position 247 of SEQ ID NO:2, and a threonine for the serine at position 533 of SEQ ID NO:2. In a related embodiment the PIGGYBAC® transposase comprises at least two of the following amino acid substitutions, a leucine for the isoleucine at position 147 of SEQ ID NO:2, a leucine for the isoleucine at position 247 of SEQ ID NO:2, and a threonine for the serine at position 533 of SEQ ID NO:2. In another related embodiment the PIGGYBAC® transposase comprises a leucine for isoleucine substitution at position 147 of SEQ ID NO:2, a leucine for isoleucine substitution at position 247 of SEQ ID NO:2, and a threonine for serine substitution at position 533 of SEQ ID NO:2. In one embodiment is provided a PIGGYBAC® transposase having the amino acid sequence of SEQ ID NO: 4, SEQ ID NO: 6, SEQ ID NO: 8, SEQ ID NO: 10, SEQ ID NO: 12, SEQ ID NO: 14, or SEQ ID NO: 16. In another aspect the invention provides a PIGGYBAC® transposase having the amino acid sequence of SEQ ID NO: 4, SEQ ID NO: 6, or SEQ ID NO: 8. In another aspect the invention provides a PIGGYBAC® transposase having the amino acid sequence of SEQ ID NO: 12, SEQ ID NO: 14, or SEQ ID NO: 16. In another aspect the invention provides a PIGGYBAC® transposase having the amino acid sequence of SEQ ID NO: 10 or 12. In another aspect the invention provides a PIGGYBAC® transposase having the amino acid sequence of SEQ ID NO:4. In another aspect the invention provides a PIGGYBAC® transposase having the amino acid sequence of SEQ ID NO:6. In another aspect the invention provides a PIGGYBAC® transposase having the amino acid sequence of SEQ ID NO:8. In another aspect the invention provides a PIGGYBAC® transposase having the amino acid sequence of SEQ ID NO:10. In another aspect the invention provides a PIGGYBAC® transposase having the amino acid sequence of SEQ ID NO: 12. In another aspect the invention provides a PIGGYBAC® transposase having the amino acid sequence of SEQ ID NO: 14. In another aspect the invention provides a PIGGYBAC® transposase having the amino acid sequence of SEQ ID NO: 16.

The PIGGYBAC® transposases described herein can be used as part of a PIGGYBAC® transposon system for gene transfer: producing cell lines: applications related to for genetic engineering, such as for genetically modifying cells, generating genome modifications: use in germline or somatic mutagenesis: use in mediating gene transfer: characterizing genes: determining gene function: oncogene screening: gene therapy: generation of pluripotent stem cells; and non-human transgenic animals (see for example US 2013/0209426: US 2010/0311116: Vanden Driessche et al., Blood 114 (8): 1461-1468, 2009; Yusa K, et al., Nat. Methods. 6 (5):363-369, 2009; Wilson et al., Mol. Ther. 15 (1):139-145, 2007; Landrette et al., PLOS ONE 6(10): 1-12, 2011: Nakanishi et al., Molecular Therapy 18 (4): 707-714, 2010): Zhao et al., Transl Lung Cancer Res., 5 (1): 120-125, 2016: Wilson et al., Molecular Therapy 15(1): 139-145, 2007).

The PIGGYBAC® transposases described herein can be used in genome editing. The PIGGYBAC® transposases described herein can be used as part of a PIGGYBAC® transposon/transposase system that is beneficial in that it offers an efficient non-viral delivery for integration into primary cell types or stem cells. The PIGGYBAC® transposases described herein can be used to enable non-viral delivery of genes encoding chimeric antigen receptors (CARs), T cell receptor (TCR) alpha and beta chains, as well as other genes encoding proteins such as cytokines, checkpoint inhibitors and other proteins to engineer cells. Multiple genes can be delivered in a single genetic construct. The advantage over viral transduction is that larger gene cargos can be accommodated, and the transposase increases the efficiency of the integration in non-viral transfection. Such a system can also be used in combination with other non-viral genome editing technologies, such as zinc finger nucleases (ZFNs), transcription activator-like effector nucleases (TALEN), clustered regularly interspaced short palindromic repeats-(CRISPR-) associated protein 9 (Cas9), integrases such as PhiC3 phase integrase, transcription activator-like effectors (TALES), sequence specific recombinases, and other transposon/transposase systems, such as Sleeping Beauty, to enable transduction in a wide variety of cells (US 2015/0031132; WO2018/098671: Ivics et al., Cell 91 (4): 501-510, 1997: Boch et al., Science 326 (5959): 1509-1512, 2009: Christian et al., Genetics 186 (2): 757-761, 2010: Wilber et al., Stem Cells Int: Vol: 2011: Article number 717069, 2011: Yusa et al., Nature 478, 20 October, 391-396, 2011: Silva et al., Curr Gene Ther 11 (1): 11-27, 2011: Cong et al., Science 339 (6121): 819-823, 2013: Mali et al., Science 339 (6121): 823-826, 2013. Li et al., Molecular Therapy: Nucleic Acids Vol. 8 September, 64-76, 2017; and Ishida et al., nature/Scientific Reports 8, Article Number 310, 2018).

The PIGGYBAC® transposases described herein can be used as part of a PIGGYBAC® transposon system to stably and non-virally, transfect cells with gene constructs encoding CARs, TCRs and/or other proteins. Native T cells can be (i) removed from a patient (subject) or donor, (ii) genetically engineered, using a PIGGYBAC® transposon/transposase system comprising PIGGYBAC® transposases described herein, to express one or more chimeric antigen receptors, T cell receptors, and/or other proteins that bind to at least one antigen of interest, (iii) expanded by cell culture into a larger population of engineered T cells, and (iv) reintroduced into the patient. After the engineered T cells are reintroduced into the patient, they mediate an immune response against cells expressing the antigen. See e.g., U.S. Pat. Nos. 7,741,465 and 6,319,494; US Patent Publication No. 2017/0355957: Nakazawa et al., J. Immunotherapy 32 (8): 826-836; 2009; Nakazawa et al., Molecular Therapy 19 (12): 2133-2143, 2011; Eshhar et al. Cancer Immunol Immunotherapy (1997) 45:131-136: Finney et al., Journal of Immunology. 161: 2791-2797, 1998: Krause et al., J. Exp. Med., 188 (4): 619-626, 1998; This immune response includes secretion of IL-2 and other cytokines by T cells, the clonal expansion of T cells recognizing the antigen, and T cell-mediated specific killing of target-positive cells. See Hombach et al., Journal of Immun. 167:6123-6131 (2001).

Immune cells may be obtained from a subject. In some embodiments, immune cells comprise T cells. T cells can be obtained from a number of sources, including peripheral blood mononuclear cells (PBMCs), bone marrow, lymph nodes tissue, cord blood, thymus tissue, tissue from a site of infection, ascites, pleural effusion, spleen tissue, and tumors. In certain embodiments, T cells can be obtained from a unit of blood collected from the subject using any number of techniques known to the skilled person, such as FICOLL™ separation. Cells may preferably be obtained from the circulating blood of an individual by apheresis. The apheresis product typically contains lymphocytes, including T cells, monocytes, granulocytes, B cells, other nucleated white blood cells, red blood cells, and platelets. In certain embodiments, the cells collected by apheresis may be washed to remove the plasma fraction and placed in an appropriate buffer or media for subsequent processing. The cells may be washed with PBS. As will be appreciated, a washing step may be used, such as by using a semiautomated flowthrough centrifuge, for example the Cobe™ 2991 cell processor, the Baxter CytoMate™, or the like. After washing, the cells may be resuspended in a variety of biocompatible buffers, or other saline solution with or without buffer. In certain embodiments, the undesired components of the apheresis sample may be removed.

In certain embodiments, T cells are isolated from PBMCs by lysing the red blood cells and depleting the monocytes, for example, using centrifugation through a PERCOLL™ gradient. A specific subpopulation of T cells, such as CD28$^+$, CD4$^+$, CD8$^+$, CD45RA$^+$, and CD45RO$^+$ T cells can be further isolated by positive or negative selection techniques known in the art. For example, enrichment of a T cell population by negative selection can be accomplished with a combination of antibodies directed to surface markers unique to the negatively selected cells. One method for use herein is cell sorting and/or selection via negative magnetic immunoadherence or flow cytometry that uses a cocktail of monoclonal antibodies directed to cell surface markers present on the cells negatively selected. For example, to enrich for CD4$^+$ cells by negative selection, a monoclonal antibody cocktail typically includes antibodies to CD14, CD20, CD11b, CD16, HLA-DR, and CD8. Flow cytometry and cell sorting may also be used to isolate cell populations of interest for use in the present invention.

PBMCs may be used directly for genetic modification with the genetic constructs (such as CARs or TCRs) using methods as described herein. In certain embodiments, after isolating the PBMCs, T lymphocytes can be further isolated and both cytotoxic and helper T lymphocytes can be sorted into naive, memory, and effector T cell subpopulations either before or after genetic modification and/or expansion.

In some embodiments, CD8$^+$ cells are further sorted into naive, central memory, and effector cells by identifying cell surface antigens that are associated with each of these types of CD8$^+$ cells. In some embodiments, the expression of phenotypic markers of central memory T cells include CD45RO, CD62L, CCR7, CD28, CD3, and CD127 and are negative for granzyme B. In some embodiments, central memory T cells are CD45RO$^+$, CD62L$^+$, CD8$^+$ T cells. In some embodiments, effector T cells are negative for CD62L, CCR7, CD28, and CD127, and positive for granzyme B and perforin. In certain embodiments, CD4$^+$ T cells are further sorted into subpopulations. For example, CD4$^+$ T helper cells can be sorted into naive, central memory, and effector cells by identifying cell populations that have cell surface antigens.

The immune cells, such as T cells, can be genetically modified following isolation using one or more vectors comprising one or more nucleotide sequences encoding one or more CARs and the PIGGYBAC® transposases described herein as part of a PIGGYBAC® transposon/transposase system. Non-viral, genetically modified immune cells can be obtained by transfecting cells with a vector comprising an engineered nucleic acid molecule encoding a PIGGYBAC® transposase as described herein and at least one nucleic acid sequence encoding at least one CAR, TCR, and/or other protein of interest flanked by at least the 5' and 3' inverted repeat elements of a PIGGYBAC® transposon. Genetically modified immune cells can also be obtained by co-transfecting immune cells with a first vector comprising an engineered nucleic acid molecule encoding a PIGGY-BAC® transposase as described herein and with a second vector comprising at least one nucleic acid sequence encoding at least one CAR, TCR, and/or other protein of interest flanked by at least the 5' and 3' inverted repeat elements of a PIGGYBAC® transposon. The vectors can be introduced to the host cell using any suitable methods known in the art, such as by electroporation or nucleofection. In a further embodiment, a mixture of different expression vectors can be used in genetically modifying a donor population of immune effector cells wherein each vector encodes a different CAR, TCR or other protein of interest. The resulting transformed immune effector cells form a mixed population of engineered cells, with a proportion of the engineered cells expressing more than one different CAR, TCR and/or other protein of interest.

Also included are suicide genes that allow for the selective elimination of the modified cells upon prodrug administration, by encoding for enzymes leading to functional active toxic products that favor the activation of apoptosis or inhibit cell proliferation, to minimize adverse events. An inducible "on" or "accelerator" switch may also be included. Suitable techniques include use of inducible caspase-9 (U.S. Published Application 2011/0286980) or a thymidine kinase, before, after or at the same time, as the cells are transfected with the CAR or TCR construct. Additional methods for introducing suicide genes and/or "on" switches include TALENS, zinc fingers, RNAi, siRNA, shRNA, antisense technology, and other techniques known in the art.

The immune cells may be activated and expanded (or differentiated in the case of progenitors) in vitro prior to being genetically modified. Methods for activating and expanding T cells are known in the art and are described, for example, in U.S. Pat. No. 6,905,874: U.S. Pat. No. 6,867,041: U.S. Pat. No. 6,797,514; and PCT WO2012/079000. Generally, such methods include contacting PBMC or isolated T cells with a stimulatory agent and costimulatory agent, such as anti-CD3 and anti-CD28 antibodies, generally attached to a bead or other surface, in a culture medium with appropriate cytokines, such as IL-2. Anti-CD3 and anti-CD28 antibodies attached to the same bead serve as a "surrogate" antigen presenting cell (APC). One example is The Dynabeads® system, a CD3/CD28 activator/stimulator system for physiological activation of human T cells.

In other embodiments, the T cells may be activated and stimulated to proliferate with feeder cells and appropriate antibodies and cytokines using methods such as those described in U.S. Pat. No. 6,040,177: U.S. Pat. No. 5,827,642; and WO2012129514, the contents of which are hereby incorporated by reference in their entirety.

PBMCs can further include other cytotoxic lymphocytes such as NK cells, NKT cells or hematopoietic stem cells. An expression vector carrying the coding sequence of a chimeric receptor as disclosed herein can be introduced into a population of human donor T cells, NK cells, NKT cells, monocytes, or hematopoietic stem cells.

Standard procedures are used for cryopreservation of cells expressing the CAR or TCT for storage and/or preparation for use in a human subject. This involves cryopreserving the immune cells such that the cells remain viable upon thawing. A fraction of the immune cells expressing the CARs can be cryopreserved by methods known in the art to provide a permanent source of such cells for the future treatment of patients afflicted with a malignancy. When needed, the cryopreserved transformed immune cells can be thawed, grown and expanded for more such cells.

As used herein, "cryopreserve" refers to the preservation of cells by cooling to sub-zero temperatures, such as (typically) 77 Kelvin or −196° C. Cryoprotective agents are often used at sub-zero temperatures to prevent the cells being preserved from damage due to freezing at low temperatures or warming to room temperature. Cryopreservative agents and optimal cooling rates can protect against cell injury and are known in the art. Cryoprotective agents include, but are not limited to, dimethyl sulfoxide (DMSO) (Lovelock & Bishop, Nature (1959); 183: 1394-1395: Ashwood-Smith, Nature (1961); 190: 1204-1205), glycerol, polyvinylpyrrolidine (Rinfret, Ann. N.Y. Acad. Sci. (1960); 85: 576), and polyethylene glycol (Sloviter & Ravdin, Nature (1962); 196: 48).

The cells are then formulated for reintroduction to the subject. The cells are formulated by first harvesting them from their culture medium, and then washing and concentrating the cells in a medium and container system suitable for administration (a "pharmaceutically acceptable" carrier) in a treatment-effective amount. Suitable infusion media can be any isotonic medium formulation, typically normal saline, Normosol™ R (Abbott) or Plasma-Lyte™ A (Baxter), but also 5% dextrose in water or Ringer's lactate can be utilized. The infusion medium can be supplemented with human serum albumin.

Desired treatment amounts of cells in the composition is generally at least 2 cells (for example, at least 1 CD8$^+$ central memory T cell and at least 1 CD4$^+$ helper T cell subset) or is more typically greater than $10^2$ cells, and up to $10^6$, up to and including $10^8$ or $10^9$ cells and can be more than $10^{10}$ cells. The number of cells will depend upon the desired use for which the composition is intended, and the type of cells included therein. The cells may be autologous, allogeneic, or heterologous to the patient undergoing therapy.

The CAR, TCR, and/or other protein of interest expressing cell populations may be administered either alone, or as a pharmaceutical composition in combination with diluents and/or with other components such as IL-2 or other cytokines or cell populations.

Methods are provided for using the engineered cells for treating conditions, diseases or disorders. Such conditions, diseases or disorders including cancers, tumors, solid tumors, hematologic disorders, leukemia, lymphomas, viral infections, inflammatory disease or disorders, and/or auto-immune disease or disorders. In some embodiments, the invention relates to creating a T cell-mediated immune response in a subject, comprising administering an effective amount of the engineered immune cells of the present application to the subject. In some embodiments, the T cell-mediated immune response is directed against a target cell or cells. In some embodiments, the engineered immune cell comprises a genetic construct expressing one or more chimeric antigen receptors (CARs), T cell receptors (TCRs) and/or other proteins of interest. In some embodiments, the target cell is a tumor cell. In some respects, the invention comprises a method for treating or preventing a malignancy, said method comprising administering to a subject in need thereof an effective amount of at least one isolated antigen binding molecule described herein. In some embodiments, the invention comprises a method for treating or preventing a malignancy, said method comprising administering to a subject in need thereof an effective amount of at least one immune cell, wherein the immune cell comprises a genetic construct encoding at least one chimeric antigen receptor, T cell receptor, and/or isolated antigen binding molecule as described herein. In some aspects, the invention comprises a method for treating or preventing inflammatory and/or autoimmune disorders. The invention also provides using the methods in support of transplantation procedures, such cell therapy against mismatched HLA molecules on the transplanted tissue/organ. In some embodiments the target cell is a pancreatic islet.

In one embodiment the invention provides a method of generating non-viral genetically modified cells, comprising (a) establishing a vector comprising at least one nucleic acid sequence encoding the least one protein of interest flanked by at least 5' and 3' inverted repeat elements of a PIGGY-BAC® transposase; (b) isolating native immune cells from a donor or subject; (b) co-transfecting the cells with a the engineered nucleic acid molecule encoding the PIGGY-BAC® transposase and with the vector comprising at least one nucleic acid sequence encoding at least one protein of interest flanked by at least the 5' and 3' inverted repeat elements of a PIGGYBAC® transposon; and (c) expanding the cells by cell culture into a larger population of non-viral, genetically modified cells. In one embodiment the cells are transfected with the vector comprising at least one nucleic acid sequence encoding at least one protein of interest flanked by at least the 5' and 3' inverted repeat elements of a PIGGYBAC® transposon, and a vector comprising a nucleic acid sequence encoding a PIGGYBAC® transposase engineered to increase stability in a cell. In one embodiment is provides an engineered nucleic acid molecule encoding a PIGGYBAC® transposase as described herein. In one embodiment the cells are transfected with a vector comprising at least one nucleic acid sequence encoding at least one protein of interest flanked by at least the 5' and 3' inverted repeat elements of a PIGGYBAC® transposon, and a nucleic acid sequence encoding a PIGGYBAC® transposase engineered to increase stability in a cell. In one embodiment is provides an engineered nucleic acid molecule encoding a PIGGYBAC® transposase as described herein. In one embodiment is provided a PIGGYBAC® transposase encoded by the nucleic acid sequence of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, or SEQ ID NO:18. In another aspect the invention provides a PIGGYBAC® transposase encoded by the nucleic acid sequence of SEQ ID NO: 3, SEQ ID NO: 5, or SEQ ID NO: 7. In another aspect the invention provides a PIGGYBAC® transposase encoded by the nucleic acid sequence of SEQ ID NO: 11, SEQ ID NO: 13, or SEQ ID NO: 15. In another aspect the invention provides a PIGGYBAC® transposase encoded by the nucleic acid sequence of SEQ ID NO: 9, or SEQ ID NO: 11. In another aspect the invention provides a PIGGYBAC® transposase encoded by the nucleic acid sequence of SEQ ID NO: 17, or SEQ ID NO: 18. In another aspect the invention provides a PIGGYBAC® transposase encoded by the nucleic acid sequence of SEQ ID NO: 3. In another aspect the invention provides a PIGGYBAC® transposase encoded by the nucleic acid sequence of SEQ ID NO: 5. In another aspect the invention provides a PIGGYBAC® transposase encoded by the nucleic acid sequence of SEQ ID NO: 7. In another aspect the invention provides a PIGGY-BAC® transposase encoded by the nucleic acid sequence of SEQ ID NO: 9. In another aspect the invention provides a PIGGYBAC® transposase encoded by the nucleic acid sequence of SEQ ID NO: 11. In another aspect the invention provides a PIGGYBAC® transposase encoded by the nucleic acid sequence of SEQ ID NO: 13. In another aspect the invention provides a PIGGYBAC® transposase encoded by the nucleic acid sequence of SEQ ID NO: 15. In another aspect the invention provides a PIGGYBAC® transposase encoded by the nucleic acid sequence of SEQ ID NO: 17. In another aspect the invention provides a PIGGYBAC® transposase encoded by the nucleic acid sequence of SEQ ID NO: 18.

In one embodiment is provided a PIGGYBAC® transposase comprising an amino acid substitution at one or more of the positions 147, 176, 221, 247, 429, 533, and 573 of SEQ ID NO: 2. In a related embodiment the PIGGYBAC® transposase comprises an amino acid substitution of leucine for the isoleucine at one or more of the positions 147, 176, 221, and 247 of SEQ ID NO:2. In a related embodiment the piggy Bac transposase comprises an amino acid substitution of threonine for serine at one or more of the positions 429, 533, and 573 of SEQ ID NO: 2. In a related embodiment the PIGGYBAC® transposase comprises an amino acid substitution of leucine for the isoleucine at one or more of the positions 147, 176, 221, and 247 and/or an amino acid substitution of threonine for serine at one or more of the positions 429, 533, and 573 of SEQ ID NO:2. In a related embodiment the PIGGYBAC® transposase comprises at least one of the following amino acid substitutions, a leucine for the isoleucine at position 147 of SEQ ID NO:2, a leucine for the isoleucine at position 247 of SEQ ID NO:2, and a threonine for the serine at position 533 of SEQ ID NO:2. In a related embodiment the PIGGYBAC® transposase comprises at least two of the following amino acid substitutions, a leucine for the isoleucine at position 147 of SEQ ID NO:2, a leucine for the isoleucine at position 247 of SEQ ID NO:2, and a threonine for the serine at position 533 of SEQ ID NO:2. In another related embodiment the PIGGYBAC® transposase comprises a leucine for isoleucine substitution at position 147 of SEQ ID NO:2, a leucine for isoleucine substitution at position 247 of SEQ ID NO:2, and a threonine for serine substitution at position 533 of SEQ ID NO:2. In one embodiment is provided a PIGGYBAC® transposase having the amino acid sequence of SEQ ID NO: 4, SEQ ID NO: 6, SEQ ID NO: 8, SEQ ID NO: 10, SEQ ID NO: 12, SEQ ID NO: 14, or SEQ ID NO: 16. In another aspect the invention provides a PIGGYBAC® transposase having the amino acid sequence of SEQ ID NO: 4, SEQ ID NO: 6, or SEQ ID NO: 8. In another aspect the invention provides a PIGGYBAC® transposase having the amino acid sequence of SEQ ID NO: 12, SEQ ID NO: 14, or SEQ ID NO: 16. In another aspect the invention provides a PIGGYBAC® transposase having the amino acid sequence of SEQ ID NO: 10 or 12. In another aspect the invention provides a PIGGY-BAC® transposase having the amino acid sequence of SEQ ID NO:4. In another aspect the invention provides a PIG-GYBAC® transposase having the amino acid sequence of SEQ ID NO:6. In another aspect the invention provides a PIGGYBAC® transposase having the amino acid sequence of SEQ ID NO:8. In another aspect the invention provides a PIGGYBAC® transposase having the amino acid sequence of SEQ ID NO:10. In another aspect the invention provides a PIGGYBAC® transposase having the amino acid sequence of SEQ ID NO: 12. In another aspect the invention provides a PIGGYBAC® transposase having the amino acid sequence of SEQ ID NO: 14. In another aspect the invention provides a PIGGYBAC® transposase having the amino acid sequence of SEQ ID NO: 16.

In one embodiment the invention provides a method of treating a subject with a non-viral genetically modified cell, comprising (a) engineering the nucleic acid molecule encoding a PIGGYBAC® transposase to increase stability in a cell and inserting into a vector: (b) isolating native immune cells from a subject or donor: (c) co-transfecting the cells with the engineered nucleic acid molecule encoding the PIGGY-BAC® transposase and with a vector comprising at least one nucleic acid sequence encoding at least one protein of interest flanked by at least the 5' and 3' inverted repeat elements of a PIGGYBAC® transposon: (d) expanding the cells by cell culture into a larger population of genetically modified cells: (e) isolating the transformed cells from the cell culture to obtain a cell population comprising the genetically modified cells; and (f) reintroducing the non-viral, genetically modified cells into the subject. In one embodiment is provided a PIGGYBAC® transposase encoded by the nucleic acid sequence of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, or SEQ ID NO: 18. In another aspect the invention provides a PIGGYBAC® transposase encoded by the nucleic acid sequence of SEQ ID NO: 3, SEQ ID NO: 5, or SEQ ID NO: 7. In another aspect the invention provides a PIGGYBAC® transposase encoded by the nucleic acid sequence of SEQ ID NO: 11, SEQ ID NO: 13, or SEQ ID NO: 15. In another aspect the invention provides a PIGGYBAC® transposase encoded by the nucleic acid sequence of SEQ ID NO: 9, or SEQ ID NO: 11. In another aspect the invention provides a PIGGYBAC® transposase encoded by the nucleic acid sequence of SEQ ID NO: 17, or SEQ ID NO:18. In another aspect the invention provides a PIGGYBAC® transposase encoded by the nucleic acid sequence of SEQ ID NO: 3. In another aspect the invention provides a PIGGYBAC® transposase encoded by the nucleic acid sequence of SEQ ID NO: 5. In another aspect the invention provides a PIGGYBAC® transposase encoded by the nucleic acid sequence of SEQ ID NO: 7. In another aspect the invention provides a PIGGY-BAC® transposase encoded by the nucleic acid sequence of SEQ ID NO: 9. In another aspect the invention provides a PIGGYBAC® transposase encoded by the nucleic acid sequence of SEQ ID NO: 11. In another aspect the invention provides a PIGGYBAC® transposase encoded by the nucleic acid sequence of SEQ ID NO: 13. In another aspect the invention provides a PIGGYBAC® transposase encoded by the nucleic acid sequence of SEQ ID NO: 15. In another aspect the invention provides a PIGGYBAC® transposase encoded by the nucleic acid sequence of SEQ ID NO: 17. In another aspect the invention provides a PIGGYBAC® transposase encoded by the nucleic acid sequence of SEQ ID NO:18.

In one embodiment is provided a PIGGYBAC® transposase comprising an amino acid substitution at one or more of the positions 147, 176, 221, 247, 429, 533, and 573 of SEQ ID NO: 2. In a related embodiment the PIGGYBAC® transposase comprises an amino acid substitution of leucine for the isoleucine at one or more of the positions 147, 176, 221, and 247 of SEQ ID NO:2. In a related embodiment the PIGGYBAC® transposase comprises an amino acid substitution of threonine for serine at one or more of the positions 429, 533, and 573 of SEQ ID NO:2. In a related embodiment the PIGGYBAC® transposase comprises an amino acid substitution of leucine for the isoleucine at one or more of the positions 147, 176, 221, and 247 and/or an amino acid substitution of threonine for serine at one or more of the positions 429, 533, and 573 of SEQ ID NO:2. In a related embodiment the PIGGYBAC® transposase comprises at least one of the following amino acid substitutions, a leucine for the isoleucine at position 147 of SEQ ID NO:2, a leucine for the isoleucine at position 247 of SEQ ID NO:2, and a threonine for the serine at position 533 of SEQ ID NO:2. In a related embodiment the PIGGYBAC® transposase comprises at least two of the following amino acid substitutions, a leucine for the isoleucine at position 147 of SEQ ID NO:2, a leucine for the isoleucine at position 247 of SEQ ID NO:2, and a threonine for the serine at position 533 of SEQ ID NO:2. In another related embodiment the PIGGYBAC® transposase comprises a leucine for isoleucine substitution at position 147 of SEQ ID NO:2, a leucine for isoleucine substitution at position 247 of SEQ ID NO:2, and a threonine for serine substitution at position 533 of SEQ ID NO:2. In one embodiment is provided a PIGGYBAC® transposase having the amino acid sequence of SEQ ID NO: 4, SEQ ID NO: 6, SEQ ID NO: 8, SEQ ID NO: 10, SEQ ID NO: 12, SEQ ID NO: 14, or SEQ ID NO: 16. In another aspect the invention provides a PIGGYBAC® transposase having the amino acid sequence of SEQ ID NO: 4, SEQ ID NO: 6, or SEQ ID NO: 8. In another aspect the invention provides a PIGGYBAC® transposase having the amino acid sequence of SEQ ID NO: 12, SEQ ID NO: 14, or SEQ ID NO: 16. In another aspect the invention provides a PIGGYBAC® transposase having the amino acid sequence of SEQ ID NO: 10 or 12. In another aspect the invention provides a PIGGY-BAC® transposase having the amino acid sequence of SEQ ID NO:4. In another aspect the invention provides a PIG-GYBAC® transposase having the amino acid sequence of SEQ ID NO:6. In another aspect the invention provides a PIGGYBAC® transposase having the amino acid sequence of SEQ ID NO:8. In another aspect the invention provides a PIGGYBAC® transposase having the amino acid sequence of SEQ ID NO:10. In another aspect the invention provides a PIGGYBAC® transposase having the amino acid sequence of SEQ ID NO: 12. In another aspect the invention provides a PIGGYBAC® transposase having the amino acid sequence of SEQ ID NO: 14. In another aspect the invention provides a PIGGYBAC® transposase having the amino acid sequence of SEQ ID NO: 16.

In a related embodiment the native immune cell is a mononuclear cell. In a related embodiment the native immune cell is a T cell. In another embodiment the protein of interest is an antigen receptor, a T cell receptor, or a chimeric antigen receptor. In another embodiment the cell is also transfected with a nucleic acid molecule encoding a suicide gene, an inducible on or accelerator switch, or both. In one embodiment is provides an engineered nucleic acid molecule encoding a PIGGYBAC® transposase as described herein.

In an embodiment, the native immune cells are transfected with a vector comprising an engineered nucleic acid molecule encoding the PIGGYBAC® transposase and a vector comprising a least one nucleic acid sequence encoding at least one protein of interest flanked by at least the 5' and the 3' inverted repeat elements of PIGGYBAC® transposase.

In an embodiment, the native immune cells are transfected with a single vector comprising an engineered nucleic acid molecule encoding the PIGGYBAC® transposase and at least one nucleic acid sequence encoding at least one protein of interest flanked by at least the 5' and the 3' inverted repeat elements of PIGGYBAC® transposase.

In one embodiment the vector includes bi-cistronic or multi-cistronic constructs that encode multiple proteins of interest.

The invention also provides non-viral genetically modified cells, cell populations, or cell cultures made according to methods described herein. Also provides is a formulation comprising the genetically modified cells or cell populations made by methods described herein.

Also provided is a method of treating or preventing a disease or disorder in a donor or subject in need thereof comprising administering to the donor or subject an effective amount of the genetically modified cells or cell populations made be methods described herein. In another embodiment is provides a pharmaceutical composition comprising the isolated, purified, protein of interest made according to the methods described herein.

While the terminology used in this application is standard within the art, definitions of certain terms are provided herein to assure clarity and definiteness to the meaning of the claims. Units, prefixes, and symbols may be denoted in their SI accepted form. Numeric ranges recited herein are inclusive of the numbers defining the range and include and are supportive of each integer within the defined range. The methods and techniques described herein are generally performed according to conventional methods well known in the art and as described in various general and more specific references that are cited and discussed throughout the present specification unless otherwise indicated. See, e.g., Sambrook et al. Molecular Cloning: A Laboratory Manual, 3rd ed., Cold Spring Harbor Laboratory Press, Cold Spring Harbor, N.Y. (2001) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990). All documents, or portions of documents, cited in this application, including but not limited to patents, patent applications, articles, books, and treatises, are hereby expressly incorporated by reference. What is described in an aspect or embodiment of the invention can be combined with other aspects and/or embodiments of the invention.

The present invention is not to be limited in scope by the specific embodiments described herein that are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

EXAMPLES

Example 1 Identification and Testing of Mutations

Figure 1:
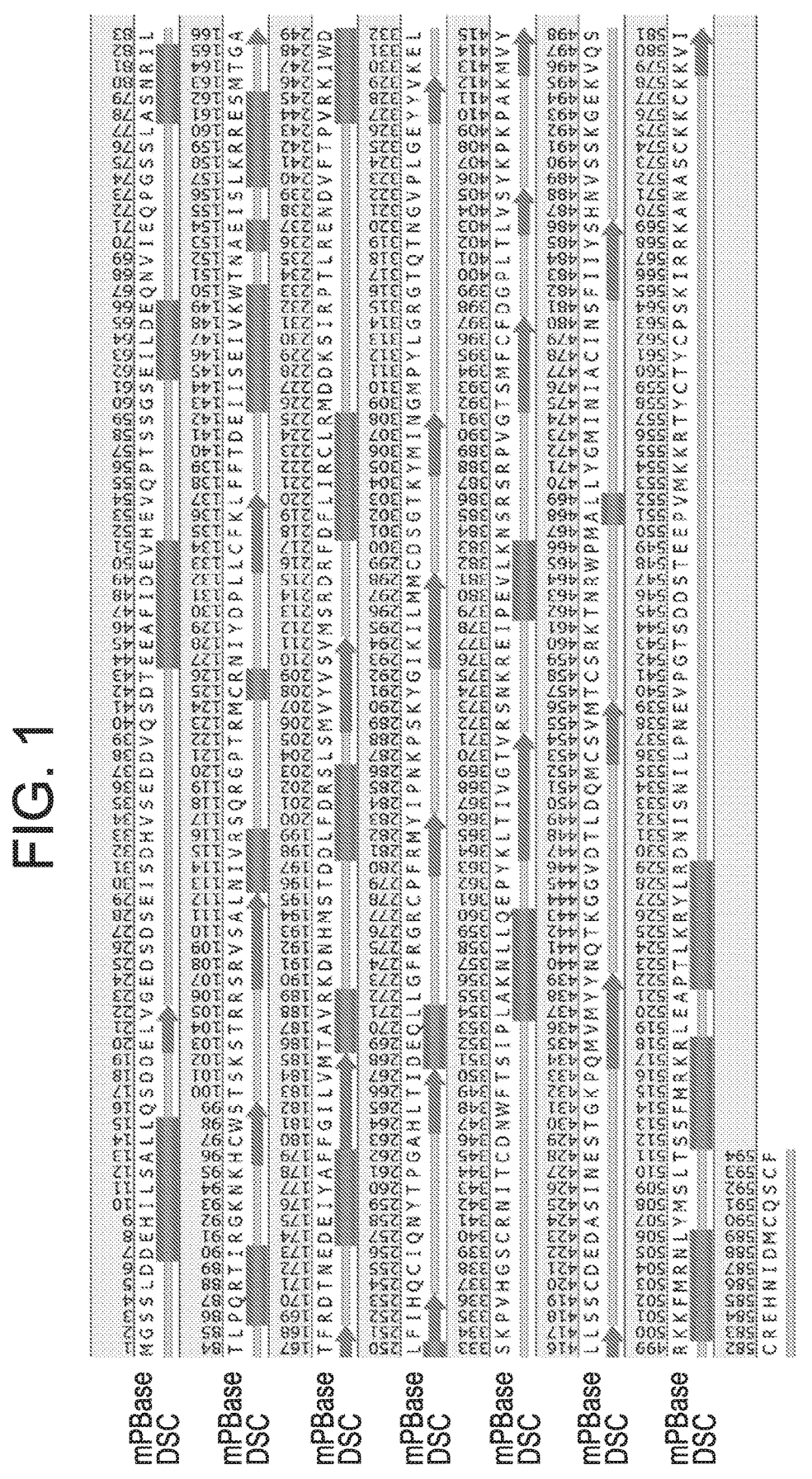

The structure of PIGGYBAC® transposase and other related transposases is not yet known. We predicted the secondary structure motifs the wild type *Trichoplusia ni* PIGGYBAC® transposase (SEQ ID NO: 2) using an in silico method termed DSC (King, R D et al., Protein Sci. 5(11): 2298-2310, 1996). See FIG. 1. We found that the PIGGYBAC® transposase is a mostly alpha helical protein. We devised mutations that might stabilize alpha helices which may improve the overall stability of the transposase and which may in turn have a positive impact on expression of the transposase. We identified I147, I176, I221, I247 as residues that could potentially be mutated to improve the stability of alpha helices of a PIGGYBAC® transposase.

We also identified putative N-linked glycosylation sites (i.e. NXS/T motif) in the transposase sequence. Since, in general, NXT motif undergoes more complete glycosylation compared to the NXS motif, we hypothesized that mutation of NXS motif to NXT motif might improve the overall glycosylation on PIGGYBAC® which in turn might improve the stability the transposase. Ser to Thr mutations in the following N-linked glycosylation sites were devised, N427ES, N531IS and N571AS. The N531IS site is present in a hydrophobic stretch and hence might confer the largest stability improvement upon improved glycosylation. It is currently unknown if PIGGYBAC® transposase is glycosylated or if that is required for activation.

A total of eight plasmids were generated which included a nucleic acid sequence encoding the wild type PIGGY-BAC® transposase and seven transposases with nucleic acid sequences encoding single, double or triple mutations (see Table 3). The cloned transposase plasmids shared the same DNA codons except for the mutated sequences. The transposase plasmids the were transformed into a cell line and colonies picked, scaled up and sequence confirmed.

TABLE 3

| SEQ ID NO | | |
|---|---|---|
| DNA | Protein | Mutation |
| 1 | 2 | WT Trichoplusia ni PIGGYBAC ® transposase |
| 3 | 4 | I147L isoleucine to leucine |
| 5 | 6 | I247L isoleucine to leucine |
| 7 | 8 | S533T serine to threonine |
| 9 | 10 | LLT (I247L I147L S533T) |
| 11 | 12 | ILT (I247 I147L S533T) |
| 13 | 14 | LIT (I247L I147 S533T) |
| 15 | 16 | LLS (I247L I147L S533) |

Four proteins of interest were tested, two monoclonal antibodies (AB1 and AB2), one fusion protein, and one bispecific T cell engager. Each gene encoding a protein of interest was cloned into a separate plasmid comprising at least the 5' and 3' inverted repeat elements of a PIGGY-BAC® transposon. These four plasmids were scaled up and sequence confirmed.

The circular mutated transposase plasmids were co-transfected along with one of the circular plasmids containing the gene encoding one of the four proteins, into glutamine synthase knock out CHO cells using electroporation. The ratio of transposase to protein of interest plasmid was 1:4. The cells were allowed to recover in media supplemented with glutamine for three days at 36° C. and 5% $CO_2$ before changing to selective media without glutamine. The cells were passaged every 3 to 4 days in selective media at 36° C. and 5% $CO_2$ until they recovered to >90% viability.

A fed batch production in 24 deep well plates was done to assess expression of the expressed protein from the stable cell lines. The cultures were seeded at $1 \times 10^6$ cells/mL in a basal production medium without glutamine, and additional nutrients were fed on days 3, 6, and 8. The cultures were harvested on day 10 and supernatants were analyzed for titer.

Titer was measured by affinity UPLC chromatography where Protein A was immobilized on a column support at a target load of 20 μg. At neutral pH, the protein in the test sample bound to the Protein A through the Fc region while host-cell proteins, conditioned media components and buffer was eluted from the column in the flow-through. Captured protein was eluted at acidic pH 1.9 1×DPBS and detected by UV absorbance at 280 nm. A calibration curve was derived from a universal antibody standard and the corresponding peak areas using linear regression analysis. Concentration of the protein in the test samples were then calculated from the calibration curve and the ratio of the extinction coefficients from the Universal antibody standard and test sample.

The use of the mutated transposases showed improved or similar titer to the WT transposase or controls lacking a transposase for the monoclonal antibodies and fusion proteins tested. Bispecific T cell engagers in general have lower titers than monoclonal antibodies and did not generally express at high levels when used in this system as well. It is possible for this particular molecule, that the expression bottleneck is not associated with transcription or gene integration site, but rather a protein secretion bottleneck. Other bispecific T cell engagers may have different results if they do not have the same challenges in expression, so it is likely that using a different scaffold with bispecific T cell engager molecules could result in better titers.

Example 2 Expression of Double and Triple Transposase Mutants in GS KO Host Cells with Addition of MSX Glutamine synthase knock out CHO cells (GSKO cells) were transfected using electroporation (Bio-Rad Laboratories, Hercules, CA), with circular plasmids encoding 1) the double mutant, "ILT" DNA PIGGYBAC® transposase (ITR, SEQ ID NO: 11), 2) the triple mutant, "LLT", DNA PIGGYBAC® transposase (LLT, SEQ ID NO: 9), and 3) no PIGGYBAC® transposase (none), all in combination with a circular plasmid containing the gene of interest and 5' and 3' inverted repeat elements of the *Trichoplusia ni* PIGGY-BAC® transposon). Three genes of interest were tested, a bi-specific T cell engager heteroFc, an IgG-scFv, and a monoclonal antibody (mAb).

Methionine sulfoximine (MSX) (EDM Millipore, Burlington, MA), 25 μM, was added 3 days post transfection (25), after recovery of the initial pool to >90% viability (0-25), or not at all (0). Addition of methionine sulfoximine (MSX), an inhibitor of glutamine synthetase, is used to increase the expression of a gene of interest in GSKO CHO cell lines.

Once the MSX-treated cells recovered they were subjected to a small scale fed batch production in 24 deep well plates or spin tubes to assess expression of the expressed protein from the stable cell lines. The cultures were seeded at $1\times10^6$ cells/mL in a basal production medium without glutamine, and additional nutrients were fed on days 3, 6, and 8. The cultures were harvested on day 10 and supernatants were analyzed for titer as described in Example 1.

Those pools transfected with a mutant transposase (ILT or LLT) showed an increase in expression as compared to those transposase pools that received no MSX treatment (0 μM MSX). For the pools where no transposase was added (none), expression did not increase with the addition of MSX.

The transposon imparts a semi-targeted mechanism of transfection that targets open chromatin which are areas of active transcription in the genome. When the transposon is integrated in combination with the transposase, the full vector sequence between the 5' and 3' inverted repeat elements of the transposon is integrated. Transfection of the transposon without the transposase results in random integration into the chromosome, and as a result, the full vector sequence between the 5' and 3' inverted repeat elements of the transposon may not be integrated into an active site. In addition, without the transposase, full integration is not guaranteed, which may lead to a disconnect between the gene of interest and the selection marker (in this case, glutamine synthase), and as such MSX would not impact expression of the gene of interest.

Figure 2:
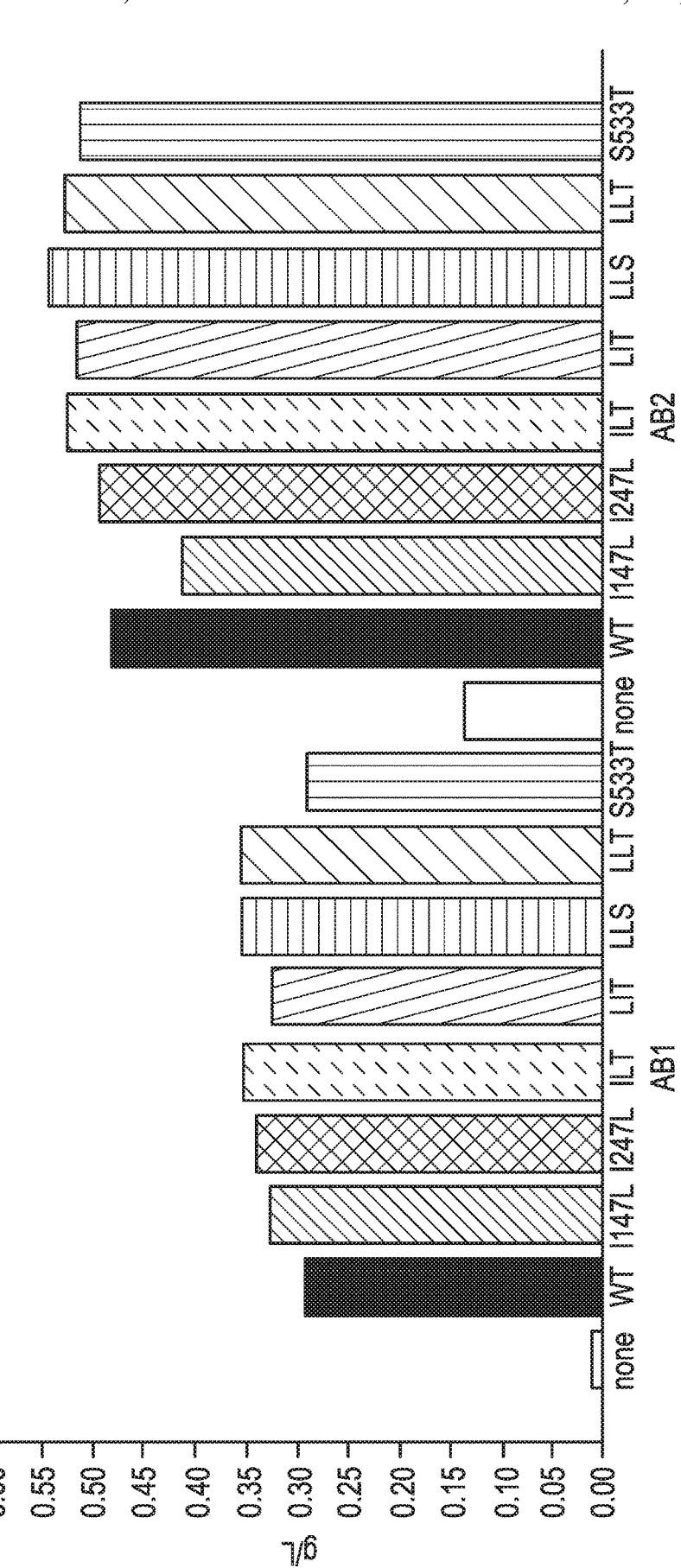
FIG. 2: Improved or comparable titer for engineered PIGGYBAC® transposase cell lines as compared to WT PIGGYBAC® transposase or no PIGGYBAC® transposase controls for monoclonal antibodies AB1 and AB2.
Figure 3:
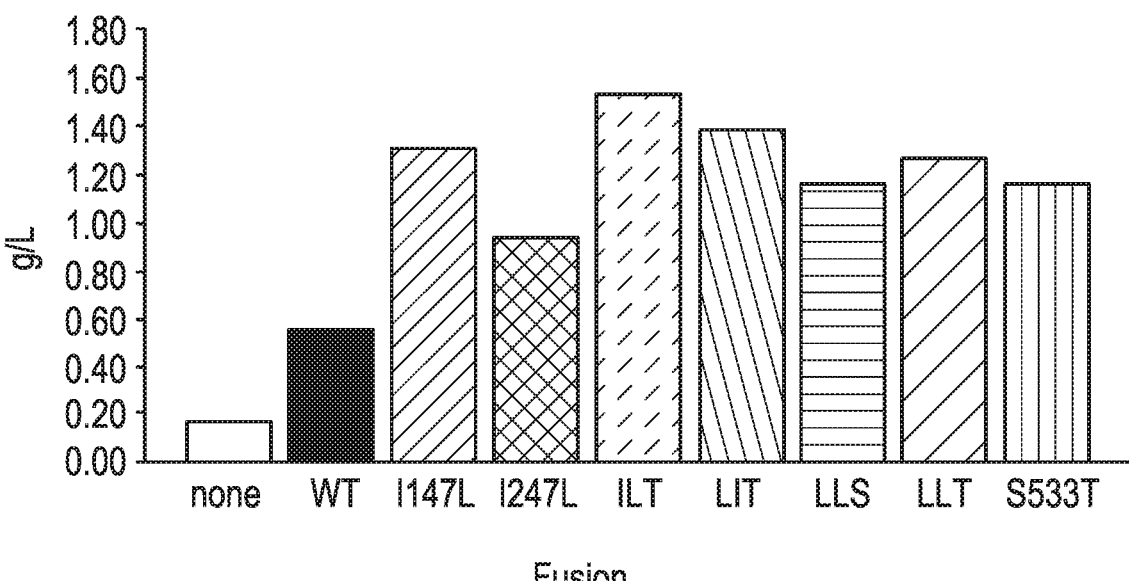
FIG. 3: Improved titer for an engineered PIGGYBAC® transposase cell line as compared to compared to WT PIGGYBAC® transposase or no PIGGYBAC® transposase controls for a cell line expressing a fusion protein.
Figure 4:
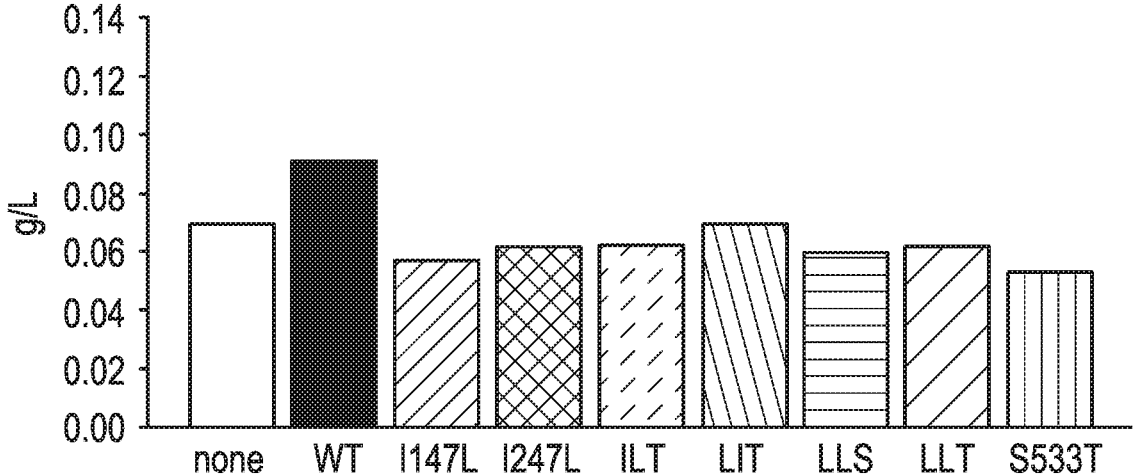
FIG. 4: Comparable titer for engineered PIGGYBAC® transposase cell lines as compared to WT PIGGYBAC® transposase or no PIGGYBAC® transposase controls for a bispecific T cell engagers molecule.
Figure 5:
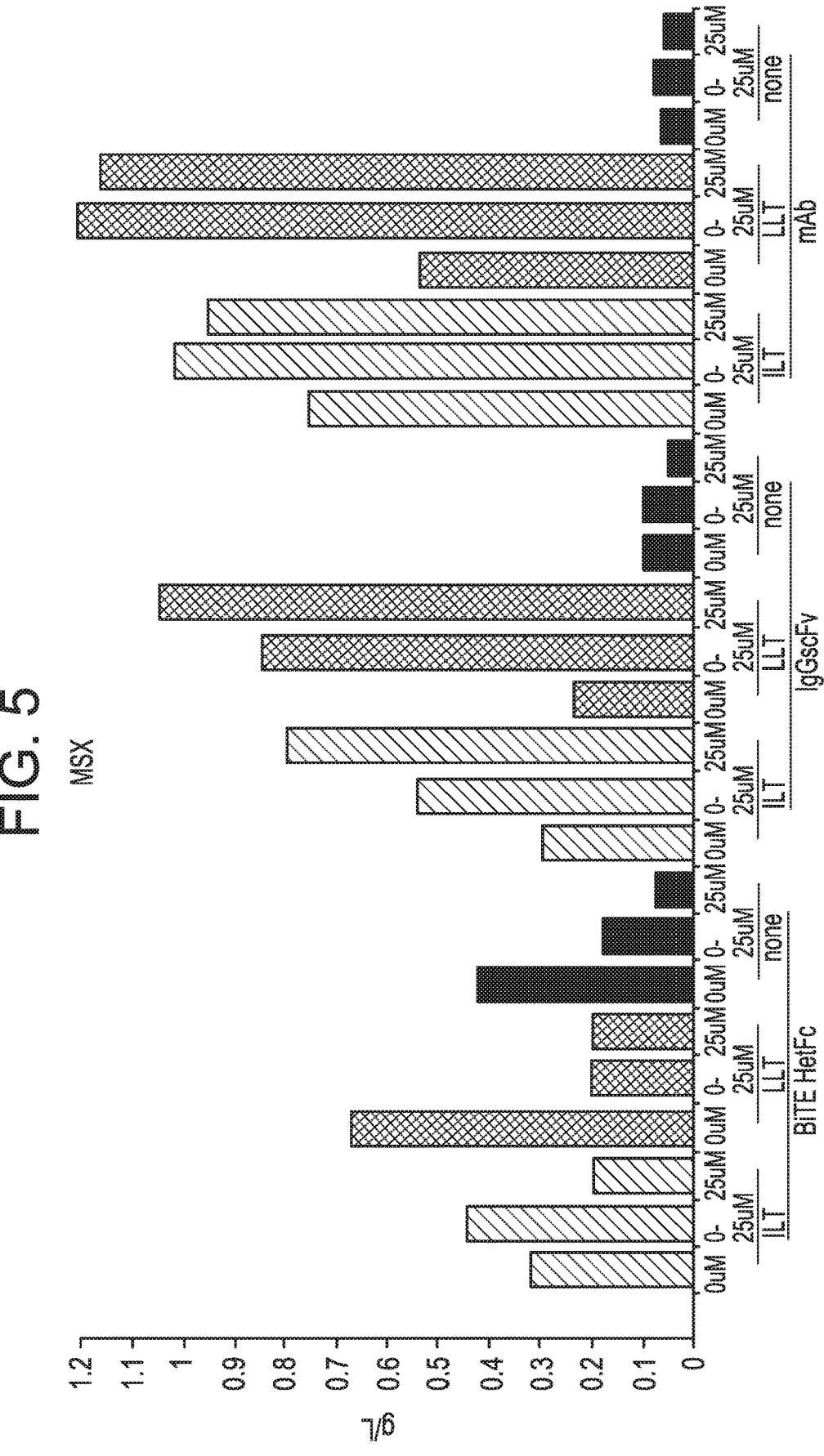
FIG. 5: Pools transfected with a PIGGYBAC® transposase double "ILT" or triple mutant "LLT" transposase showed an increase in expression as compared to those transposase pools that received no MSX treatment (0 μM MSX). For the pools where no transposase was added (none), expression did not increase with the addition of MSX. A BiTE® HeteroFc, an IgGscFV and a mAb were tested. MSX added at transfection (25) or after recovery of initial DNA transposase transfected pool (0-25).

In the context of the vector system tested, the engineered transposase has the added advantage of increasing both the expression with and without the addition of MSX as compared to the control with no transposase. (FIG. 5). Increased copy number from PIGGYBAC® may also contribute to improved selection with MSX.

Example 3 Transfection with DNA or mRNA PIGGYBAC® Transposases

The transposase that is used for integration of the gene of interest can be either DNA or mRNA-based. One concern with the use of a DNA transcribed transposase is the potential for the transposase gene to integrate into the genome which could result in active transcription/translation of the transposase in the transfected cell line. This could possibly lead to genomic instability due to transposase activity at potential cryptic transposase recognition sites. An alternative is to use mRNA for transfection since it does not integrate into the genome.

An unmodified mRNA transcript using wild-type bases, as well as a modified synthetic mRNA transcript having 25% substitution of pseudo-U and 5-Methyl-C Capped were prepared for the double mutant, "ILT", and the triple mutant, "LLT", PIGGYBAC® transposases.

Two sets of experiments were performed to evaluate mRNA translated-transposase from transfection. In the first experiment, mRNA transcripts for the PIGGYBAC® transposase double mutant (ILT, SEQ ID NO: 17), and the triple mutant (LLT, SEQ ID NO: 18), were tested. In the second experiment, a synthetic mRNA transcript for the double mutant "ILT" having 25% substitution of pseudo-U and 5-Methyl-C Capped was tested in addition to the mRNA transcript.

The mRNA and synthetic mRNA transcripts, along with a circular plasmid comprising the 5' and 3' inverted repeat elements of the *Trichoplusia ni* PIGGYBAC® transposon and a gene encoding a monoclonal antibody, were transfected into a GSKO cell line, using either an electroporation, or a lipid-based transfection method.

For the electroporation, equal weights of linearized transposase and transposon vector DNA were added to $2\times10^7$ cells suspended in media in a cuvette. The DNA cell mixture was electroporated using a BIO-RAD® electroporator (Bio-Rad Laboratories). The electroporated cells were then added to warm growth media and incubated at 37° C. and 5% $CO_2$ for 3 days, after which the cells were resuspended in selective media to establish stable pools. For the lipid transfection, the reagent used was LIPOFECTAMINE® LTX (Gibco/ThermoFisher, Waltham, MA). The day before transfection, cells were seeded in 1e6 cells/mL, shaking in suspension. On the day of transfection, cells were seeded in the transfection media into a 6 well plate. The Mab DNA/transposase/LIPOFECTAMINE® LTX complex was prepared and incubated. The complex then was added to the cells and incubated for 5-8 hours. After incubation, growth media was added, and the cells were allowed to recover for 2-3 days. Trypsin was used to dislodge the cells if there were sticking and the cells were centrifuged and resuspended in selective media to establish stable pools.

The mRNA transfections were compared to the control conditions, a GSKO cell line transfected with the corresponding DNA encoding a transposase. A circular plasmid comprising DNA encoding the double mutant (ILT, SEQ ID NO: 11) or the triple mutant (LLT, SEQ ID NO:9), along with a circular plasmid comprising the 5' and 3' inverted terminal repeat elements of a *Trichoplusia ni* PIGGYBAC® transposon comprising a monoclonal antibody, were transfected under the same conditions as the mRNA.

The amounts of mRNA and DNA transposase, the gene of interest, the ratio of the gene of interest DNA or RNA to transposase, and the number of cells transfected were varied to test for optimal conditions, Table 4.

TABLE 4

Conditions for electroporation and lipofection.

| Transposase | Mab DNA (µg) | Transposase DNA or mRNA (µg) | Ration Mab to transposase |
|---|---|---|---|
| Experiment 1 Electroporation 2e7 host cells | | | |
| DNA control | 20 | 5 | 4:1 |
| None | 20 | 0 | |
| mRNA | 20 | 5 | 4:1 |
| mRNA | 20 | 10 | 2:1 |
| mRNA | 20 | 20 | 1:1 |
| mRNA | 14 | 100 | 1:7 |
| mRNA | 28 | 200 | 1:7 |
| Experiment 2 LIPOFECTAMINE ® LXT 1.2e6 host cells | | | |
| DNA control | 2 | 0.5 | 4:1 |
| DNA control | 2 | 2 | 1:1 |
| DNA control | 4 | 4 | 1:1 |
| mRNA | 2 | 0.5 | 4:1 |
| mRNA | 2 | 2 | 1:1 |
| mRNA | 4 | 4 | 1:1 |
| Experiment 3 Electroporation 2e7 host cells | | | |
| DNA control | 30 | 15 | 2:1 |
| mRNA | 30 | 15 | 2:1 |
| Synthetic mRNA | 30 | 15 | 2:1 |

The transfected cells were allowed to recover in media supplemented with glutamine for three days at 36° C. and 5% $CO_2$ before changing to selective media without glutamine. They were passaged every 3 to 4 days in selective media at 36° C. and 5% $CO_2$ until they recovered to >90% viability and assayed for titer as described in Example 1.

Figure 6A:
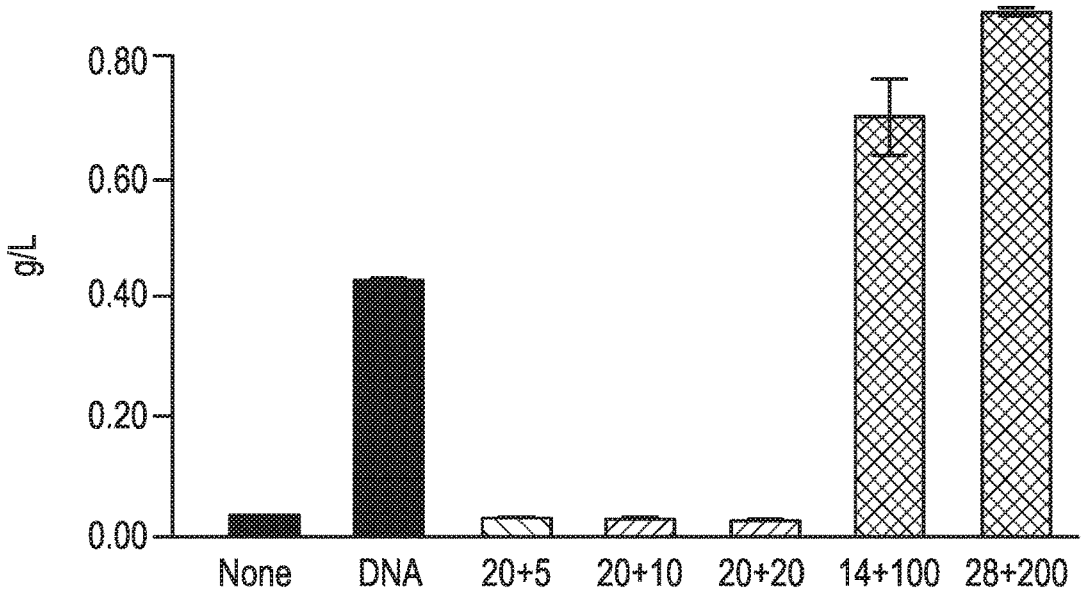
FIGS. 6A and B Pool expression levels associated with PIGGYBAC® transposase double mutant "ILT" DNA or mRNA transfected using electroporation or lipid-based methods.
Figure 6B:
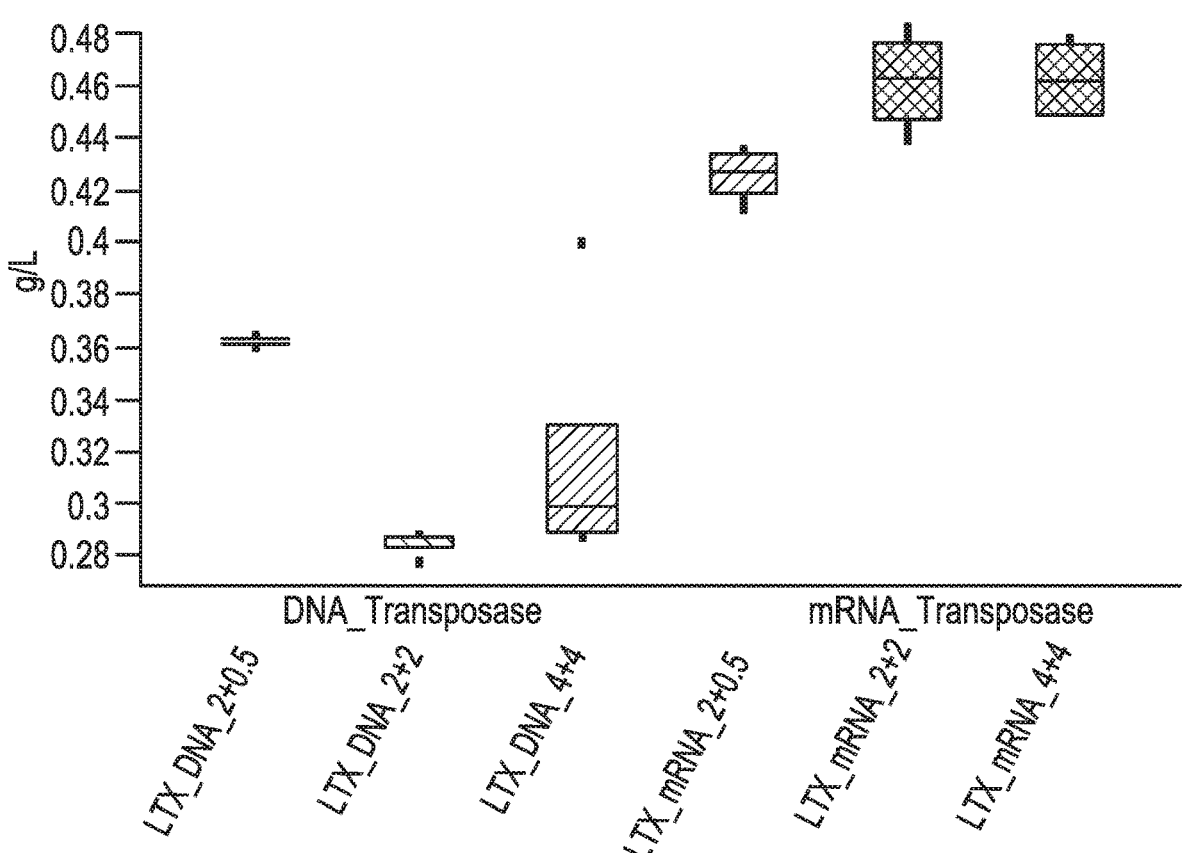

Transfections with mRNA achieved comparable expression levels to transfections using DNA for the PIGGYBAC® transposase double mutant, "ILT", using either an electroporation-based or a lipid-based transfection method. FIG. 6 shows the expression levels of the monoclonal antibody from cells transfected with double mutant, "ILT", transposase DNA or mRNA using the electroporation or lipid-based method. FIG. 6A shows the results from transfection using electroporation. Expression improved, compared to the DNA control, as the amount of mRNA was increased. The triple mutant "LLT" gave similar results, data not shown. FIG. 6B shows the results from transfection using the lipid-based method. Expression levels of the monoclonal antibody were better or at least comparable to the DNA control.

The results from the synthetic version of mRNA was compared to mRNA using electroporation. Both versions had higher expression than the control that was not transfected with a transposase (-).

FIG. 7 shows the expression levels of the monoclonal antibody in association with expression of the double mutant transposase "ILT" DNA and both mRNA transfected pools from electroporation. Synthetic mRNA and mRNA transfected pools had similar titers to the DNA-based transposase pools and higher titers than no transposase control pools.

Analysis of the Integration of the Transposase Gene at the Genome DNA Level.

Integration of the PIGGYBAC® transposase double mutant, "ILT" and the triple mutant "LLT" genes at the genomic DNA level were also analyzed. Oligo primers to the 5' and 3' ends of the transposase nucleotide sequence were used that amplified a ~1.7 kb fragment to check if the transposase was present. Genomic DNA was extracted using a Blood and Cell Culture DNA Maxi kit (Qiagen, Valencia, CA) from cell pellets collected at 1e7 cells from recovered cell lines transfected with the either the mRNA or DNA. Plasmid DNA was included as a positive control. The genomic DNA was quantified and checked for quality (≥1.8 was good quality) by the 260/280 absorbance ratio using a NANODROP® spectrophotometer (ThermoFisher, Waltham, MA). PCR amplification was performed using the Q5® High Fidelity Polymerase from New England Biolabs (Ipswich, MA) on a PROFLEX™ PCR system (Life Technologies, Carlsburg, CA). The reaction was run on an agarose gel for visualization.

Analysis of the Integration of the Transposase Gene at the cDNA Level

Integration of the PIGGYBAC® transposase double mutant, "ILT" gene at the transcript level was also analyzed. The oligo primers described above were again used to amplify a ~1.7 kb fragment to check if the transposase transcript was present in the cell. mRNA was extracted using a RNEASY® minikit (Qiagen) from cell pellets collected at 1e7 cells from recovered cell lines transfected with the addition of either mRNA or DNA transposase. Plasmid DNA was included as a control. The mRNA was quantified and checked for quality by the 260/280 absorbance ratio using a NANODROP® spectrophotometer. The transposase was checked on a transcript level using a SUPERSCRIPT™ III One-Step RT-PCR System with PLATINUM™ Taq High Fidelity DNA Polymerase (ThermoFisher) which performs cDNA synthesis and subsequent amplification of the target sequence (i.e. transposase) on a PROFLEX™ PCR system (Life Technologies) according to manufacturer's recommendations. The reaction was run on an agarose gel for visualization.

Figure 8B:
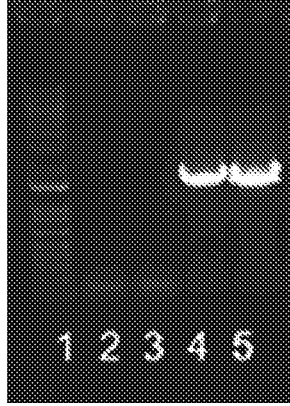

The DNA and mRNA transfected cell line pools were checked for integration both at the genomic and transcript level, FIG. 8. The presence of an ~1.7 kb band indicated the presence of the transposase in the genome of the cell line, FIG. 8A. All pool cell lines transfected with double mutant, "ILT", DNA transposase had integration at the transcript level, whereas those transfected with mRNA did not have integration at the genomic or transcript levels, FIG. 8B.

ddPCR Assay for Copy Number

To assay copy number, genomic DNA was extracted from $5 \times 10^6$ cells for each clone and pool using DNEASY® Blood and Tissue kit (Qiagen). Digital droplet PCR was performed using ddPCR SUPERMIX™ for Probes (no dUTP) kit (Bio-Rad), according to manufacturer's recommendations. Each reaction contained 1 unit of HindIII, 10 ng of template DNA, as well as 900 nm forward and reverse primers, and 250 nm of fluorescent probe designed towards the target double mutant "ILT" coding sequence and the endogenous CHO reference gene, Gcg. Droplets were generated using the AUTODG® system (Bio-Rad) and PCR amplification was performed on a PROFLEX™ PCR system (Life Technologies) with the thermal cycling conditions of 10 min at 95° C., followed by 40 cycles of 94° C. for 30 s and 60° C. for 1 min, then 98° C. for 10 min. Droplets were read on the QX200® Droplet Reader system (Bio-Rad), and copy number data analysis was performed using QUANTASOFT® software (Bio-Rad).

To determine if all clones within a pool had the transposase integrated, pools transfected with DNA transposase were single cell cloned and checked for integration at the genomic DNA (gDNA) level. The pool and the clones were also assayed for copy number of the transposase using ddPCR.

The pool had low copy number and contained clones that did not have integration of the transposase. Clones without transposase integration were identified by screening clones using a PCR based method, as described above. Clones with no transposase integrated were present in the pool population, FIG. 9.

Example 4 Generation of TCR-T Cells Using a PIGGYBAC® Transposase

The double mutated PIGGYBAC® transposase "ILT" was used to successfully modify primary T cells to express a T-cell receptor (TCR), FIG. 10A. PIGGYBAC®-generated TCR-T cells exhibited robust killing of target as well antigen-specific proliferation (FIGS. 10 B and 10 C).

Peripheral blood mononuclear cells (PBMCs) were first isolated from healthy donor leukopaks by FICOLL-PAQUE® (GE Healthcare, Chicago, IL) separation, and T cells subsequently isolated from PBMCs using EASYSEP® Human T cell Isolation Kit (Stemcell Technologies, Vancouver, Canada). T cells were then activated and two days post-activation, the T cells were co-electroporated with a plasmid comprising the 5' and 3' inverted terminal repeat elements of a PIGGYBAC® transposon comprising the genes encoding TCR-IRES-EGFP and the mRNA encoding the double mutant "ILT" transposase, (SEQ ID NO: 18), using the 4-D NUCLEOFECTOR® system (Lonza, Greenwood, SC). Cells were supplemented with IL2 cytokine every 2-3 days.

Determination of TCR Integration

On day 7 post-activation, T cells were evaluated for TCR expression and cell phenotype by surface staining of cells with dextramer antibody (Immudex, Copenhagen, Denmark) recognizing TCR, as well as CD3, CD4, and CD8 fluorophore-conjugated antibodies (Biolegend, San Diego, CA). Samples were analyzed for expression by running on BD® LSRII flow cytometer.

Functional Assays

T cells were counted and collected for functional assays on day 9-14 post activation.

Cell Lysis and Proliferation Assay

1E5 CELLTRACE® Violet (Thermo Fisher Scientific, Waltham, MA)-stained T cells were coincubated with 5e4 target cells in 150 μL media in a 96-well U-bottom plate for 5 days. Target cell lysis and T cell proliferation by were evaluated by CELLTRACE® Violet dilution were quantified by running samples on BD LSRFORTESSA® flow cytometer (Liberty Lake, WA).

---

What is claimed is:

1. A transposase comprising the sequence of SEQ ID NO: 2 with an amino acid substitution at one or more of the positions 147, 176, 221, 247, 429, 533, and 573 of SEQ ID NO: 2.

2. The transposase according to claim 1, comprising an amino acid substitution of leucine for the isoleucine at one or more of the positions 147, 176, 221, and 247 of SEQ ID NO:2.

3. The transposase according to claim 1, comprising an amino acid substitution of threonine for serine at one or more of the positions 429, 533, and 573 of SEQ ID NO:2.

4. The transposase according to claim 1, comprising an amino acid substitution of leucine for the isoleucine at one or more of the positions 147, 176, 221, and 247 and an amino acid substitution of threonine for serine at one or more of the positions 429, 533, and 573 of SEQ ID NO:2.

5. The transposase according to claim 4, comprising at least one of the following amino acid substitutions, a leucine for the isoleucine at position 147 of SEQ ID NO:2, a leucine for the isoleucine at position 247 of SEQ ID NO: 2, and a threonine for the serine at position 533 of SEQ ID NO:2.

6. The transposase according to claim 4, comprising at least two of the following amino acid substitutions, a leucine for the isoleucine at position 147 of SEQ ID NO:2, a leucine for the isoleucine at position 247 of SEQ ID NO: 2, and a threonine for the serine at position 533 of SEQ ID NO:2.

7. The transposase according to claim 4, comprising a leucine for isoleucine substitution at position 147 of SEQ ID NO:2, a leucine for isoleucine substitution at position 247 of SEQ ID NO:2, and a threonine for serine substitution at position 533 of SEQ ID NO:2.

8. A transposase comprising the amino acid sequence of SEQ ID NO: 4, SEQ ID NO: 6, SEQ ID NO: 8, SEQ ID NO: 10, SEQ ID NO: 12, SEQ ID NO: 14, or SEQ ID NO: 16.

9. An engineered nucleic acid molecule encoding a transposase comprising the sequence of SEQ ID NO: 2 with an amino acid substitution at one or more of the positions 147, 176, 221, 247, 429, 53, and 573 of SEQ ID NO: 2.

10. A vector comprising the nucleic acid molecule according to claim 9.

11. The vector according to claim 10, further comprising at least one nucleic acid sequence encoding at least one protein of interest flanked by at least the 5' and 3' inverted repeat elements of a transposon.

12. The vector according to claim 11, wherein the vector comprises one or more nucleic acid sequences encoding one or more proteins of interest.

13. A cell transfected with the vector according to claim 11.

14. An isolated cell transfected with a vector according to claim 10.

15. A cell co-transfected with the vector according to claim 10, and a vector comprising at least one nucleic acid molecule encoding at least one protein of interest flanked by at least the 5' and 3' inverted repeat elements of a transposon.

16. A transposase encoded by the nucleic acid sequence of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, or SEQ ID NO:18.

17. An isolated cell transfected with a transposase encoded by the nucleic acid sequence of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, or SEQ ID NO: 18.

18. The cell according to claim 17 or 14, wherein the cell is a host cell.

19. The cell according to claim 17 or 14, wherein the cell is a CHO cell.

20. The cell according to claim 17 or 14, wherein the cell is an immune cell.

21. An isolated cell co-transfected with an engineered nucleic acid molecule encoding the transposase according to claim 8, and a vector comprising at least one nucleic acid molecule encoding at least one protein of interest flanked by at least the 5' and 3' inverted repeat elements of a transposon.

22. A transposase comprising the amino acid sequence of SEQ ID NO: 12.

23. A vector comprising a nucleic acid sequence encoding a transposase comprising the amino acid sequence of SEQ ID NO: 12.

24. The vector of claim 23, further comprising at least one nucleic acid sequence encoding at least one protein of interest flanked by at least the 5' and 3' inverted repeat elements of a transposon.

25. A cell transfected with the vector according to claim 24.

26. An isolated cell co-transfected with the vector according to claim 23, and a vector comprising at least one nucleic acid molecule encoding at least one protein of interest flanked by at least the 5' and 3' inverted repeat elements of a transposon.

\* \* \* \* \*